(12) United States Patent
Forsbach et al.

(10) Patent No.: US 7,662,949 B2
(45) Date of Patent: Feb. 16, 2010

(54) IMMUNOSTIMULATORY OLIGORIBONUCLEOTIDES

(75) Inventors: Alexandra Forsbach, Ratingen (DE); Jörg Vollmer, Düsseldorf (DE); Grayson B. Lipford, Watertown, MA (US)

(73) Assignees: Coley Pharmaceutical GmbH, Langenfeld (DE); Coley Pharmaceutical Group, Inc., Wellesley, MA (US)

( * ) Notice: Subject to any disclaimer, the term of this patent is extended or adjusted under 35 U.S.C. 154(b) by 426 days.

(21) Appl. No.: 11/603,978

(22) Filed: Nov. 22, 2006

(65) Prior Publication Data
US 2007/0142315 A1    Jun. 21, 2007

Related U.S. Application Data

(60) Provisional application No. 60/739,529, filed on Nov. 25, 2005, provisional application No. 60/778,989, filed on Mar. 3, 2006.

(51) Int. Cl.
C07H 21/04 (2006.01)
C07H 21/02 (2006.01)
A61K 48/00 (2006.01)
A61K 39/00 (2006.01)

(52) U.S. Cl. .............. 536/24.5; 536/23.1; 536/24.2; 536/24.31; 536/24.33; 514/44; 424/184.1

(58) Field of Classification Search ............ None
See application file for complete search history.

(56) References Cited

U.S. PATENT DOCUMENTS

| | | | |
|---|---|---|---|
| 3,906,092 A | 9/1975 | Hilleman et al. |
| 5,488,039 A | 1/1996 | Masor et al. |
| 5,492,899 A | 2/1996 | Masor et al. |
| 5,602,109 A | 2/1997 | Masor et al. |
| 5,612,060 A | 3/1997 | Alexander |
| 5,663,153 A | 9/1997 | Hutcherson et al. |
| 5,700,590 A | 12/1997 | Masor et al. |
| 5,712,256 A | 1/1998 | Kulkarni et al. |
| 5,723,335 A | 3/1998 | Hutcherson et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,239,116 B1 | 5/2001 | Krieg et al. |
| 6,339,068 B1 | 1/2002 | Krieg et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,479,504 B1 | 11/2002 | Macfarlane et al. |
| 6,521,637 B2 | 2/2003 | Macfarlane |
| 6,653,292 B1 | 11/2003 | Krieg et al. |
| 6,727,230 B1 | 4/2004 | Hutcherson et al. |
| 6,821,957 B2 | 11/2004 | Krieg et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 7,223,741 B2 | 5/2007 | Krieg |
| 7,271,156 B2 | 9/2007 | Krieg et al. |
| 7,354,711 B2 | 4/2008 | Macfarlane |
| 2001/0044416 A1 | 11/2001 | McCluskie et al. |
| 2002/0091097 A1 | 7/2002 | Bratzler et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0198165 A1 | 12/2002 | Bratzler et al. |
| 2003/0026782 A1 | 2/2003 | Krieg |
| 2003/0026801 A1 | 2/2003 | Weiner et al. |
| 2003/0050263 A1 | 3/2003 | Krieg et al. |
| 2003/0050268 A1 | 3/2003 | Krieg et al. |
| 2003/0055014 A1 | 3/2003 | Bratzler |
| 2003/0091599 A1 | 5/2003 | Davis et al. |
| 2003/0100527 A1 | 5/2003 | Krieg et al. |
| 2003/0139364 A1 | 7/2003 | Krieg et al. |
| 2003/0148316 A1 | 8/2003 | Lipford et al. |

(Continued)

FOREIGN PATENT DOCUMENTS

EP    0 216 133 B1    7/1989

(Continued)

OTHER PUBLICATIONS

Heil et al., Species-specific recognition of single-stranded RNA via toll-like receptor 7 and 8. Science. Mar. 5, 2004;303(5663):1526-9.

(Continued)

*Primary Examiner*—Amy Bowman
(74) *Attorney, Agent, or Firm*—Paul M. Misiak

(57) ABSTRACT

The invention provides immunostimulatory compositions and use of those compounds in the preparation of medicaments for the treatment of disease as well as in vitro uses. In particular, the compositions of the invention include immunostimulatory oligoribonucleotides that incorporate a sequence-dependent immunostimulatory sequence motif. Specific modifications involving phosphate linkages, nucleotide analogs, adducts, and combinations thereof are provided. Compositions of the invention, which optionally can include an antigen, can be used alone or together with other treatments to stimulate or enhance an immune response. Also provided are compositions and methods useful for treating a subject having an infection, a cancer, an allergic condition, asthma, airway remodeling, or immunodeficiency. Immunostimulatory oligoribonucleotides of the invention are believed to stimulate Toll-like receptor 8 (TLR8).

14 Claims, 13 Drawing Sheets

U.S. PATENT DOCUMENTS

| | | |
|---|---|---|
| 2003/0148976 A1 | 8/2003 | Krieg et al. |
| 2003/0166001 A1 | 9/2003 | Lipford |
| 2003/0181406 A1 | 9/2003 | Schetter et al. |
| 2003/0191079 A1 | 10/2003 | Krieg et al. |
| 2003/0224010 A1 | 12/2003 | Davis et al. |
| 2003/0232074 A1 | 12/2003 | Lipford et al. |
| 2003/0232856 A1 | 12/2003 | Macfarlane |
| 2004/0009949 A1 | 1/2004 | Krieg |
| 2004/0030118 A1 | 2/2004 | Wagner et al. |
| 2004/0053880 A1 | 3/2004 | Krieg |
| 2004/0067902 A9 | 4/2004 | Bratzler et al. |
| 2004/0067905 A1 | 4/2004 | Krieg |
| 2004/0087534 A1 | 5/2004 | Krieg et al. |
| 2004/0087538 A1 | 5/2004 | Krieg et al. |
| 2004/0092472 A1 | 5/2004 | Krieg |
| 2004/0106568 A1 | 6/2004 | Krieg et al. |
| 2004/0131628 A1 | 7/2004 | Bratzler et al. |
| 2004/0132685 A1 | 7/2004 | Krieg et al. |
| 2004/0142469 A1 | 7/2004 | Krieg et al. |
| 2004/0143112 A1 | 7/2004 | Krieg et al. |
| 2004/0147468 A1 | 7/2004 | Krieg et al. |
| 2004/0152649 A1 | 8/2004 | Krieg |
| 2004/0152656 A1 | 8/2004 | Krieg et al. |
| 2004/0152657 A1 | 8/2004 | Krieg et al. |
| 2004/0162258 A1 | 8/2004 | Krieg et al. |
| 2004/0162262 A1 | 8/2004 | Krieg et al. |
| 2004/0167089 A1 | 8/2004 | Krieg et al. |
| 2004/0171150 A1 | 9/2004 | Krieg et al. |
| 2004/0171571 A1 | 9/2004 | Krieg et al. |
| 2004/0181045 A1 | 9/2004 | Krieg et al. |
| 2004/0198680 A1 | 10/2004 | Krieg |
| 2004/0198688 A1 | 10/2004 | Krieg et al. |
| 2004/0229835 A1 | 11/2004 | Krieg et al. |
| 2004/0234512 A1 | 11/2004 | Wagner et al. |
| 2004/0235770 A1 | 11/2004 | Davis et al. |
| 2004/0235774 A1 | 11/2004 | Bratzler et al. |
| 2004/0235777 A1 | 11/2004 | Wagner et al. |
| 2004/0235778 A1 | 11/2004 | Wagner et al. |
| 2004/0247662 A1 | 12/2004 | Dow et al. |
| 2004/0266719 A1 | 12/2004 | McCluskie et al. |
| 2005/0004061 A1 | 1/2005 | Krieg et al. |
| 2005/0004062 A1 | 1/2005 | Krieg et al. |
| 2005/0009774 A1 | 1/2005 | Krieg et al. |
| 2005/0013812 A1 | 1/2005 | Dow et al. |
| 2005/0032734 A1 | 2/2005 | Krieg et al. |
| 2005/0032736 A1 | 2/2005 | Krieg et al. |
| 2005/0037403 A1 | 2/2005 | Krieg et al. |
| 2005/0037985 A1 | 2/2005 | Krieg et al. |
| 2005/0043529 A1 | 2/2005 | Davis et al. |
| 2005/0049215 A1 | 3/2005 | Krieg et al. |
| 2005/0049216 A1 | 3/2005 | Krieg et al. |
| 2005/0054601 A1 | 3/2005 | Wagner et al. |
| 2005/0054602 A1 | 3/2005 | Krieg et al. |
| 2005/0059619 A1 | 3/2005 | Krieg et al. |
| 2005/0059625 A1 | 3/2005 | Krieg et al. |
| 2005/0070491 A1 | 3/2005 | Krieg et al. |
| 2005/0075302 A1 | 4/2005 | Hutcherson et al. |
| 2005/0100983 A1 | 5/2005 | Bauer et al. |
| 2005/0101554 A1 | 5/2005 | Krieg et al. |
| 2005/0101557 A1 | 5/2005 | Krieg et al. |
| 2005/0119273 A1 | 6/2005 | Lipford et al. |
| 2005/0123523 A1 | 6/2005 | Krieg et al. |
| 2005/0130911 A1 | 6/2005 | Uhlmann et al. |
| 2005/0148537 A1 | 7/2005 | Krieg et al. |
| 2005/0169888 A1 | 8/2005 | Hartmann et al. |
| 2005/0171047 A1 | 8/2005 | Krieg et al. |
| 2005/0181422 A1 | 8/2005 | Bauer et al. |
| 2005/0182017 A1 | 8/2005 | Krieg |
| 2005/0197314 A1 | 9/2005 | Krieg et al. |
| 2005/0215501 A1 | 9/2005 | Lipford et al. |
| 2005/0233995 A1 | 10/2005 | Krieg et al. |
| 2005/0233999 A1 | 10/2005 | Krieg et al. |
| 2005/0239732 A1 | 10/2005 | Krieg et al. |
| 2005/0239733 A1 | 10/2005 | Jurk et al. |
| 2005/0239734 A1 | 10/2005 | Uhlmann et al. |
| 2005/0244379 A1 | 11/2005 | Krieg et al. |
| 2005/0244380 A1 | 11/2005 | Krieg et al. |
| 2005/0245477 A1 | 11/2005 | Krieg et al. |
| 2005/0250716 A1 | 11/2005 | Schmidt et al. |
| 2005/0250726 A1 | 11/2005 | Krieg et al. |
| 2005/0256073 A1 | 11/2005 | Lipford et al. |
| 2005/0267064 A1 | 12/2005 | Krieg et al. |
| 2005/0277604 A1 | 12/2005 | Krieg et al. |
| 2005/0277609 A1 | 12/2005 | Krieg et al. |
| 2006/0003955 A1 | 1/2006 | Krieg et al. |
| 2006/0003962 A1 | 1/2006 | Ahluwalia et al. |
| 2006/0019916 A1 | 1/2006 | Krieg et al. |
| 2006/0019923 A1 | 1/2006 | Davis et al. |
| 2006/0058251 A1 | 3/2006 | Krieg et al. |
| 2006/0089326 A1 | 4/2006 | Krieg et al. |
| 2006/0094683 A1 | 5/2006 | Krieg et al. |
| 2006/0140875 A1 | 6/2006 | Krieg et al. |
| 2006/0154890 A1 | 7/2006 | Bratzler et al. |
| 2006/0172966 A1 | 8/2006 | Lipford et al. |
| 2006/0188913 A1 | 8/2006 | Krieg et al. |
| 2006/0211639 A1 | 9/2006 | Bratzler et al. |
| 2006/0211644 A1 | 9/2006 | Krieg et al. |
| 2006/0229271 A1 | 10/2006 | Krieg et al. |
| 2006/0241076 A1 | 10/2006 | Uhlmann et al. |
| 2006/0246035 A1 | 11/2006 | Ahluwalia et al. |
| 2006/0286070 A1 | 12/2006 | Hartmann et al. |
| 2006/0287263 A1 | 12/2006 | Davis et al. |
| 2007/0009482 A9 | 1/2007 | Krieg et al. |
| 2007/0010470 A9 | 1/2007 | Krieg et al. |
| 2007/0037767 A1 | 2/2007 | Bratzler et al. |
| 2007/0065467 A1 | 3/2007 | Krieg et al. |
| 2007/0066553 A1 | 3/2007 | Krieg et al. |
| 2007/0066554 A1 | 3/2007 | Krieg et al. |
| 2007/0078104 A1 | 4/2007 | Krieg et al. |
| 2007/0129320 A9 | 6/2007 | Davis et al. |
| 2007/0142315 A1 | 6/2007 | Forsbach et al. |
| 2007/0184465 A1 | 8/2007 | Wagner et al. |
| 2007/0202128 A1 | 8/2007 | Krieg et al. |
| 2007/0224210 A1 | 9/2007 | Krieg et al. |
| 2007/0232622 A1 | 10/2007 | Lipford et al. |
| 2008/0009455 A9 | 1/2008 | Krieg et al. |
| 2008/0026011 A1 | 1/2008 | Krieg et al. |
| 2008/0031936 A1 | 2/2008 | Krieg et al. |
| 2008/0045473 A1 | 2/2008 | Uhlmann et al. |
| 2008/0113929 A1 | 5/2008 | Lipford et al. |

FOREIGN PATENT DOCUMENTS

| | | |
|---|---|---|
| EP | 0 286 224 B1 | 11/1992 |
| WO | WO 99/37151 A1 | 7/1999 |
| WO | WO 99/56755 A1 | 11/1999 |
| WO | WO 00/06588 A1 | 2/2000 |
| WO | WO 00/14217 A2 | 3/2000 |
| WO | WO 00/67023 A1 | 11/2000 |
| WO | WO 01/36641 A2 | 5/2001 |
| WO | WO 01/45750 A1 | 6/2001 |
| WO | WO 01/93902 A2 | 12/2001 |
| WO | WO 03/086280 A2 | 10/2003 |
| WO | WO 2004/007743 A2 | 1/2004 |
| WO | WO 2004/026888 A2 | 4/2004 |
| WO | WO 2004/094671 A2 | 11/2004 |
| WO | WO 2005/097993 A2 | 10/2005 |
| WO | WO 2006/020768 A2 | 2/2006 |
| WO | WO 2006/063252 A2 | 6/2006 |
| WO | WO 2006/092607 A1 | 9/2006 |
| WO | WO 2007/031319 A1 | 3/2007 |
| WO | WO 2007/031322 A1 | 3/2007 |
| WO | WO 2007/042554 A2 | 4/2007 |
| WO | WO 2008/030455 A2 | 3/2008 |

| | | |
|---|---|---|
| WO | WO 2008/033432 A2 | 3/2008 |
| WO | WO 2008/039538 A2 | 4/2008 |

OTHER PUBLICATIONS

Press Release, Jan. 2007, "Coley Pharmaceutical Group Updates Hepatitis C Drug Development Strategy".

Press Release, Jun. 2007, "Coley Pharmaceutical Group Announces Pfizer's Discontinuation of Clinical Trials for PF-3512676 Combined with Cytotoxic Chemotherapy in Advanced Non Small Cell Lung Cancer".

Agrawal et al., Role of Toll-like receptors in antisense and siRNA [corrected]. Nat Biotechnol. Dec. 2004;22(12):1533-7.

Alexopoulou et al., Recognition of double-stranded RNA and activation of NF-kappaB by Toll-like receptor 3. Nature. Oct. 18, 2001;413(6857):732-8.

Beignon et al., Endocytosis of HIV-1 activates plasmacytoid dendritic cells via Toll-like receptor-viral RNA interactions. J Clin Invest. Nov. 2005;115(11):3265-75.

Boczkowski et al., Dendritic cells pulsed with RNA are potent antigen-presenting cells in vitro and in vivo. J Exp Med. Aug. 1, 1996;184(2):465-72.

Cella et al., Maturation, activation, and protection of dendritic cells induced by double-stranded RNA. J Exp Med. Mar. 1, 1999;189(5):821-9.

Diamantstein et al., Specific binding of poly(I)-poly(C) to the membrane of murine B lymphocyte subsets. Eur J Immunol. Dec. 1978;8(12):896-9.

Diebold et al., Innate antiviral responses by means of TLR7-mediated recognition of single-stranded RNA. Science. Mar. 5, 2004;303(5663):1529-31.

Elliott et al., Probing the TRAP-RNA interaction with nucleoside analogs. RNA. Oct. 1999;5(10):1277-89.

Ewel et al., Polyinosinic-polycytidylic acid complexed with poly-L-lysine and carboxymethylcellulose in combination with interleukin 2 in patients with cancer: clinical and immunological effects. Cancer Res. Jun. 1, 1992;52(11):3005-10.

Fanslow et al., Effect of nucleotide restriction and supplementation on resistance to experimental murine candidiasis. JPEN J Parenter Enteral Nutr. Jan.-Feb. 1988;12(1):49-52. Abstract Only.

Ghisolfi-Neito et al., Nucleolin is a sequence-specific RNA-binding protein: characterization of targets on pre-ribosomal RNA. J Mol Biol. Jul. 5, 1996;260(1):34-53.

Goodman, Cellular and biochemical studies of substituted guanine ribonucleoside immunostimulants. Immunopharmacology. Jan.-Feb. 1991;21(I):51-68.

Hadden, Immunostimulants. Trends Pharmacol Sci. May 1993;14(5):169-74.

Hannon, RNA interference. Nature. Jul. 11, 2002;418(6894):244-51.

Heidel et al., Administration in non-human primates of escalating intravenous doses of targeted nanoparticles containing ribonucleotide reductase subunit M2 siRNA. Proc Natl Acad Sci U S A. Apr. 3, 2007;104(14):5715-21. Epub Mar. 22, 2007.

Johnson, Non-specific resistance against microbial infections induced by polyribonucleotide complexes. In: Immunopharmacology of infection diseases: Vaccine adjuvants and modulators of non-specific resistance. 1987: 291-301.

Jyonouchi et al., Immunomodulating actions of nucleotides: enhancement of immunoglobulin production by human cord blood lymphocytes. Pediatr Res. Nov. 1993;34(5):565-71.

Kariko et al., Suppression of RNA recognition by Toll-like receptors: the impact of nucleoside modification and the evolutionary origin of RNA. Immunity. Aug. 2005;23(2):165-75.

Khan et al., Polyadenylic-polyuridylic acid enhances the natural cell-mediated cytotoxicity in patients with breast cancer undergoing mastectomy. Surgery. Sep. 1995;118(3):531-8.

Lacour, Clinical trials using polyadenylic-polyuridylic acid as an adjuvant to surgery in treating different human tumors. J Biol Response Mod. Oct. 1985;4(5):538-43.

Löseke et al., In vitro-generated viral double-stranded RNA in contrast to polyinosinic:polycytidylic acid induces interferon-alpha in human plasmacytoid dendritic cells. Scand J Immunol. Apr. 2006;63(4):264-74.

Lund et al., Recognition of single-stranded RNA viruses by Toll-like receptor 7. Proc Natl Acad Sci U S A. Apr. 13, 2004;101(15):5598-603.

Michelson et al. Poly(A).poly(U) as adjuvant in cancer treatment distribution and pharmacokinetics in rabbits. Proc Soc Exp Biol Med. Jun. 1985;179(2):180-6.

Mitchell et al., RNA transfected dendritic cells as cancer vaccines. Curr Opin Mol Ther, Apr. 2000;2(2):176-81.

Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.

Park et al. Adjuvant effect of polyadenylic.polyuridylic acid on antibody production of recombinant hepatitis B surface antigen in mice. Int J Immunopharmacol. Jun. 1995;17(6):513-6.

Peng et al., Toll-like receptor 8-mediated reversal of CD4+ regulatory T cell function. Science. Aug. 26, 2005;309(5739):1380-4.

Scheel et al., Immunostimulating capacities of stabilized RNA molecules. Eur J Immunol. Feb. 2004;34(2):537-47.

Sen et al., The critical DNA flanking sequences of a CpG oligodeoxynucleotide, but not the 6 base CpG motif, can be replaced with RNA without quantitative or qualitative changes in Toll-like receptor 9-mediated activity. Cell Immunol. Nov.-Dec. 2004;232(1-2):64-74.

Sioud, Single-stranded small interfering RNA are more immunostimulatory than their double-stranded counterparts: a central role for 2'-hydroxyl uridines in immune responses. Eur J Immunol. May 2006;36(5):1222-30.

Sioud et al., Innate sensing of self and non-self RNAs by Toll-like receptors. Trends Mol Med. Apr. 2006;12(4):167-76.

Stull et al., Antigene, ribozyme and aptamer nucleic acid drugs: progress and prospects. Pharm Res. Apr. 1995;12(4):465-83.

Sugiyama et al., CpG RNA: identification of novel single-stranded RNA that stimulates human CD14+CD11c+ monocytes. J Immunol. Feb. 15, 2005;174(4):2273-9.

Talmadge et al., Immunomodulatory effects in mice of polyinosinic-polycytidylic acid complexed with poly-L-lysine and carboxymethylcellulose. Cancer Res. Mar. 1985;45(3):1058-65.

Thompson et al., Lymphokine-activated killer (LAK) cells. V. 8-Mercaptoguanosine as an IL-2-sparing agent in LAK generation. J Immunol. Nov. 15, 1990;145(10):3524-31.

Tursz et al., Poly A-poly U: An updated review. In: Immunotherapeutic Prospects of Infectious Diseases. 1990:263-72.

Vollmer et al., Modulation of CpG oligodeoxynucleotide-mediated immune stimulation by locked nucleic acid (LNA). Oligonucleotides. 2004 Spring;14(1):23-31.

Whitmore et al., Synergistic activation of innate immunity by double-stranded RNA and CpG DNA promotes enhanced antitumor activity. Cancer Res. Aug. 15, 2004;64(16):5850-60.

Wiltrout et al., Immunomodulation of natural killer activity by polyribonucleotides. J Biol Response Mod. Oct. 1985;4(5):512-7.

Srinivasan et al., "Continuum Solvent Studies of the Stability of RNA Hairpin Loops and Helices", Journal of Biomolecular Structure & Dynamics, 16(3):671-682, 1998.

Schroeder and Turner, "Factors Affecting the Thermodynamic Stability of Small Asymmetric Internal Loops in RNA", Biochemistry, 39(31):9257-9274, 2000.

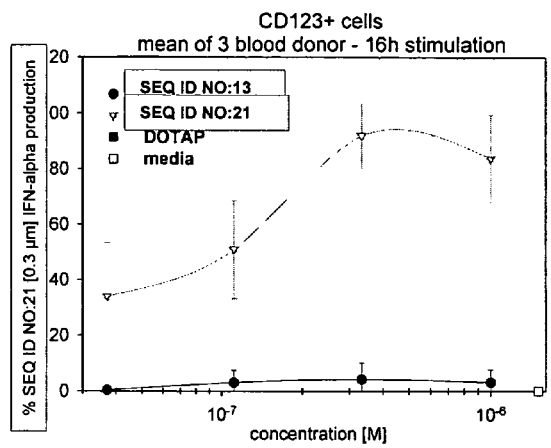
Figure 6a
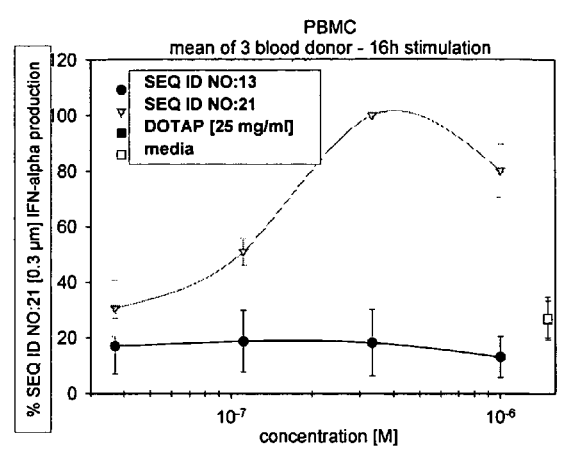
Figure 6b
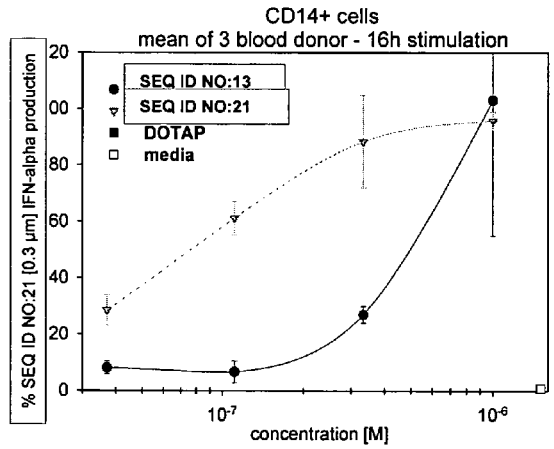
Figure 6c
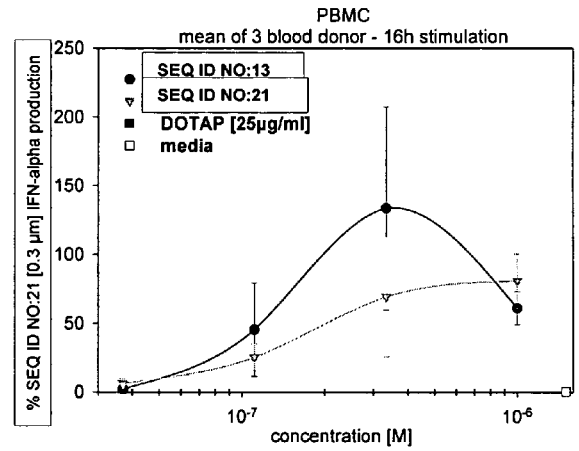
Figure 6d
Figure 6

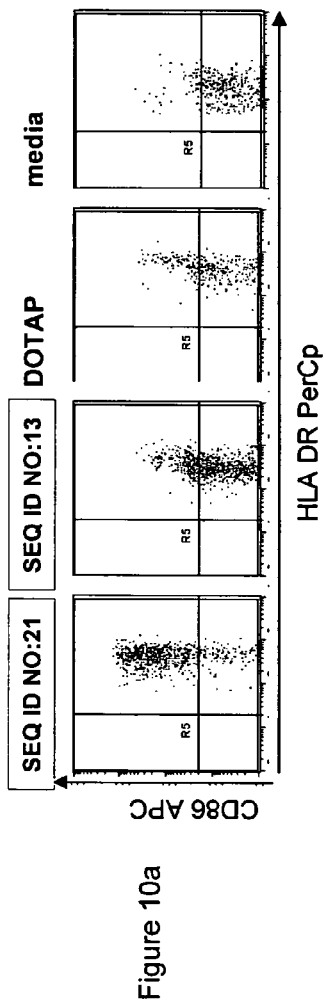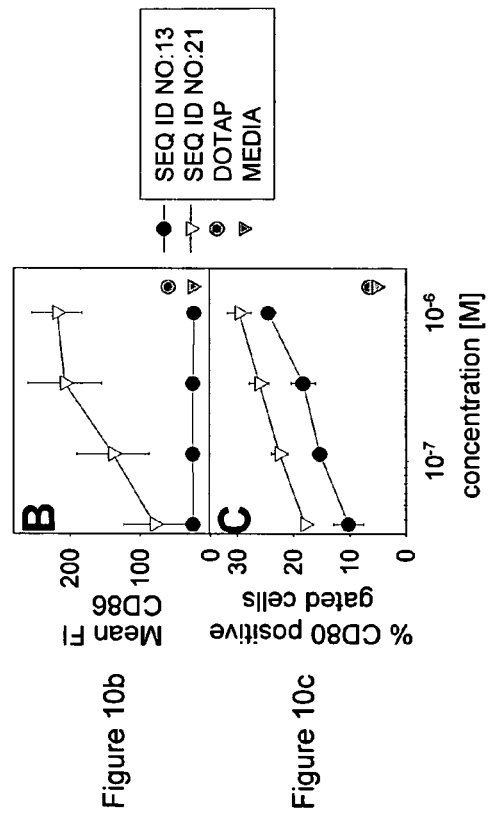
Figure 10a
Figure 10b
Figure 10c
Figure 10

Figure 11a
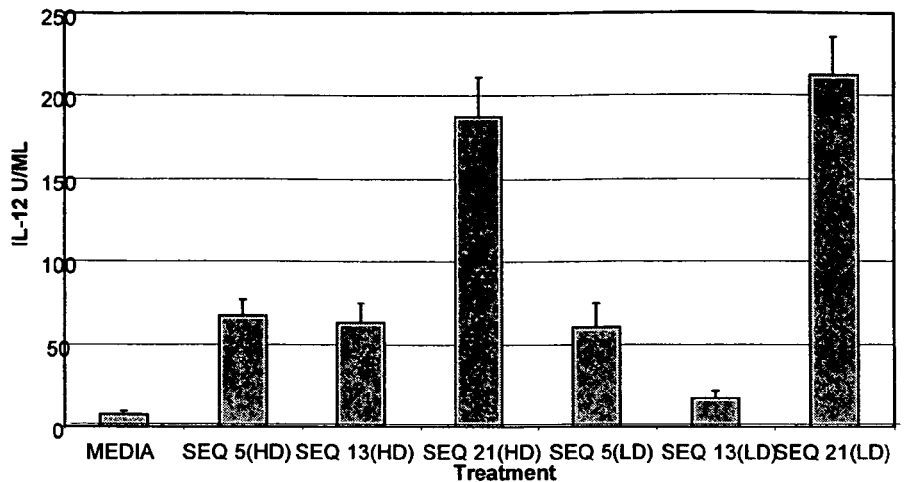
Figure 11b
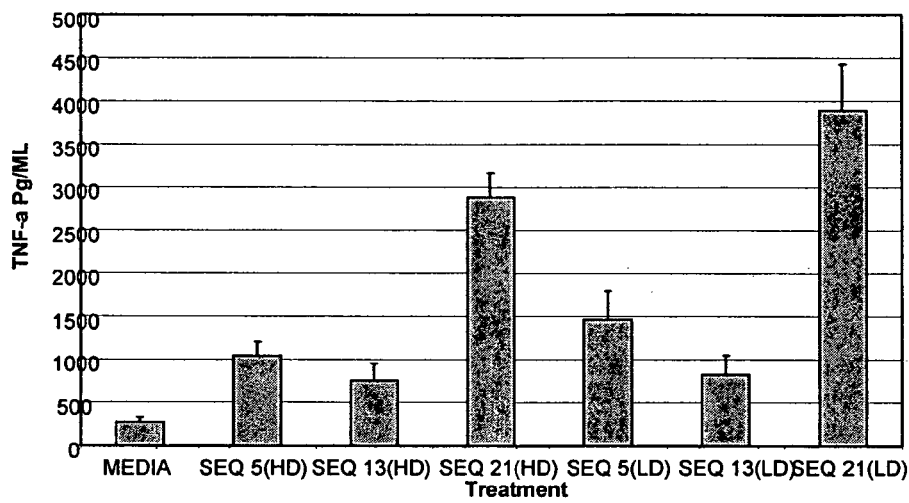
Figure 11c
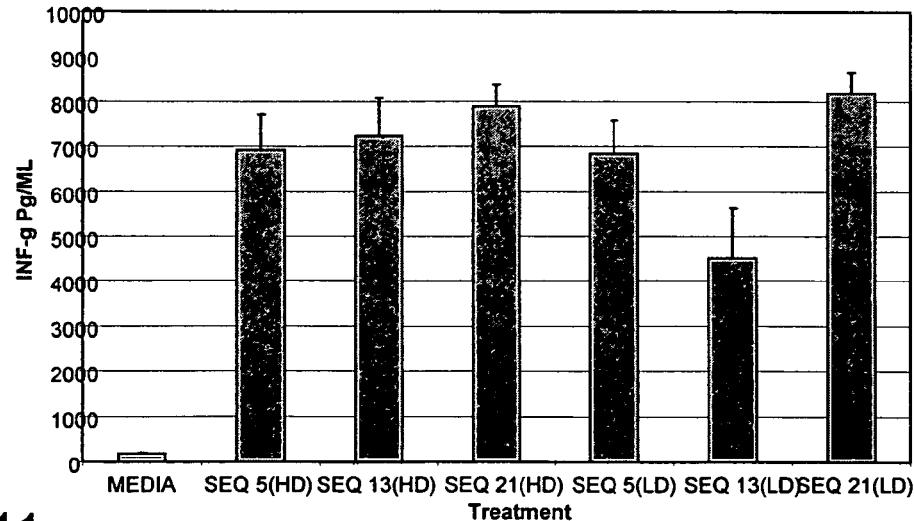
Figure 11

SEQUENCE LISTING

<160> NUMBER OF SEQ ID NOS: 91

<210> SEQ ID NO 1
<211> LENGTH: 8
<212> TYPE: RNA
<213> ORGANISM: Artificial sequence
<220> FEATURE:
<223> OTHER INFORMATION: Synthetic oligonucleotide

<400> SEQUENCE: 1 guaggcac                                                                 8

<210> SEQ ID NO 2
<211> LENGTH: 8
<212> TYPE: RNA
<213> ORGANISM: Artificial sequence
<220> FEATURE:
<223> OTHER INFORMATION: Synthetic oligonucleotide

<400> SEQUENCE: 2 uuaggcac                                                                 8

<210> SEQ ID NO 3
<211> LENGTH: 8
<212> TYPE: RNA
<213> ORGANISM: Artificial sequence
<220> FEATURE:
<223> OTHER INFORMATION: Synthetic oligonucleotide

<400> SEQUENCE: 3 cuaggcac                                                                 8

<210> SEQ ID NO 4
<211> LENGTH: 8
<212> TYPE: RNA
<213> ORGANISM: Artificial sequence
<220> FEATURE:
<223> OTHER INFORMATION: Synthetic oligonucleotide

<400> SEQUENCE: 4 auaggcac                                                                 8

<210> SEQ ID NO 5
<211> LENGTH: 18
<212> TYPE: RNA
<213> ORGANISM: Artificial sequence
<220> FEATURE:
<223> OTHER INFORMATION: Synthetic oligonucleotide

<400> SEQUENCE: 5
ccgucuguug ugugacuc                                                     18

<210> SEQ ID NO 6
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 6
uguuuuuucu cuuguuuggu                                                   20

<210> SEQ ID NO 7
<211> LENGTH: 18

```
<212> TYPE: DNA
<213> ORGANISM: Artificial sequence
<220> FEATURE:
<223> OTHER INFORMATION: Synthetic oligonucleotide, combined DNA/RNA
<220> FEATURE:
<221> NAME/KEY: misc_feature
<222> LOCATION: (1)..(5)
<223> OTHER INFORMATION: wherein n is any deoxyribonucleotide
<220> FEATURE:
<221> NAME/KEY: misc_feature
<222> LOCATION: (6)..(6)
<223> OTHER INFORMATION: wherein n is any ribonucleotide
<220> FEATURE:
<221> NAME/KEY: misc_feature
<222> LOCATION: (8)..(8)
<223> OTHER INFORMATION: wherein n is uracil
<220> FEATURE:
<221> NAME/KEY: misc_feature
<222> LOCATION: (10)..(10)
<223> OTHER INFORMATION: wherein n is uracil
<220> FEATURE:
<221> NAME/KEY: misc_feature
<222> LOCATION: (11)..(12)
<223> OTHER INFORMATION: wherein n is any ribonucleotide
<220> FEATURE:
<221> NAME/KEY: misc_feature
<222> LOCATION: (13)..(18)
<223> OTHER INFORMATION: wherein n is any deoxyribonucleotide

<400> SEQUENCE: 7
nnnnnnanan nnnnnnnn                                                  18

<210> SEQ ID NO 8
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 8
aaacaacaaa cacacaaacc                                                20

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide, combined DNA/RNA
<220> FEATURE:
<221> NAME/KEY: misc_feature
<222> LOCATION: (1)..(5)
<223> OTHER INFORMATION: wherein n is any deoxyribonucleotide
<220> FEATURE:
<221> NAME/KEY: misc_feature
<222> LOCATION: (7)..(7)
<223> OTHER INFORMATION: wherein n is uracil
<220> FEATURE:
<221> NAME/KEY: misc_feature
<222> LOCATION: (9)..(9)
<223> OTHER INFORMATION: wherein n is uracil
<220> FEATURE:
<221> NAME/KEY: misc_feature
<222> LOCATION: (11)..(11)
<223> OTHER INFORMATION: wherein n is uracil
<220> FEATURE:
<221> NAME/KEY: misc_feature
<222> LOCATION: (13)..(13)
<223> OTHER INFORMATION: wherein n is uracil
<220> FEATURE:
<221> NAME/KEY: misc_feature
<222> LOCATION: (14)..(19)
<223> OTHER INFORMATION: wherein n is any deoxyribonucleotide

<400> SEQUENCE: 9
```

| | |
|---|---|
| nnnnnanana nannnnnnn | 19 |

<210> SEQ ID NO 10
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 10

| | |
|---|---|
| gccaccgagc cgaaggcacc | 20 |

<210> SEQ ID NO 11
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 11

| | |
|---|---|
| gccaccgagc cgaauauacc | 20 |

<210> SEQ ID NO 12
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 12

| | |
|---|---|
| auauauauau auauauauau | 20 |

<210> SEQ ID NO 13
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 13

| | |
|---|---|
| uuauuauuau uauuauuauu | 20 |

<210> SEQ ID NO 14
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 14

| | |
|---|---|
| uuuauuuauu uauuuauuua | 20 |

<210> SEQ ID NO 15
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 15

| | |
|---|---|
| uuuuauuuua uuuuauuuua | 20 |

<210> SEQ ID NO 16
<211> LENGTH: 20
<212> TYPE: RNA
<213> ORGANISM: Artificial sequence

```
<220> FEATURE:
<223> OTHER INFORMATION: Synthetic oligonucleotide

<400> SEQUENCE: 16
aauaauaaua auaauaauaa                                              20

<210> SEQ ID NO 17
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 17
aaauaaauaa auaaauaaau                                              20

<210> SEQ ID NO 18
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 18
aaaauaaaau aaaauaaaau                                              20

<210> SEQ ID NO 19
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 19
cucucucucu cucucucucu                                              20

<210> SEQ ID NO 20
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 20
gugugugugu gugugugugu                                              20

<210> SEQ ID NO 21
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 21
uuguuguugu uguuguuguu                                              20

<210> SEQ ID NO 22
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 22
uuuguuuguu uguuuguuug                                              20
```

```
<210> SEQ ID NO 23
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 23
uuuuguuuug uuuuguuuug                                                    20

<210> SEQ ID NO 24
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 24
cuacuacuac uacuacuacu                                                    20

<210> SEQ ID NO 25
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 25
guaguaguag uaguaguagu                                                    20

<210> SEQ ID NO 26
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 26
gucgucgucg ucgucgucgu                                                    20

<210> SEQ ID NO 27
<211> LENGTH: 20
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: wherein n is inosine
<220> FEATURE:
<221> NAME/KEY: misc_feature
<222> LOCATION: (4)..(4)
<223> OTHER INFORMATION: wherein n is inosine
<220> FEATURE:
<221> NAME/KEY: misc_feature
<222> LOCATION: (7)..(7)
<223> OTHER INFORMATION: wherein n is inosine
<220> FEATURE:
<221> NAME/KEY: misc_feature
<222> LOCATION: (10)..(10)
<223> OTHER INFORMATION: wherein n is inosine
<220> FEATURE:
<221> NAME/KEY: misc_feature
<222> LOCATION: (13)..(13)
<223> OTHER INFORMATION: wherein n is inosine
<220> FEATURE:
<221> NAME/KEY: misc_feature
<222> LOCATION: (16)..(16)
<223> OTHER INFORMATION: wherein n is inosine
```

```
<220> FEATURE:
<221> NAME/KEY: misc_feature
<222> LOCATION: (19)..(19)
<223> OTHER INFORMATION: wherein n is inosine

<400> SEQUENCE: 27
nuanuanuan uanuanuanu                                               20

<210> SEQ ID NO 28
<211> LENGTH: 20
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(3)
<223> OTHER INFORMATION: wherein n is inosine
<220> FEATURE:
<221> NAME/KEY: misc_feature
<222> LOCATION: (6)..(6)
<223> OTHER INFORMATION: wherein n is inosine
<220> FEATURE:
<221> NAME/KEY: misc_feature
<222> LOCATION: (9)..(9)
<223> OTHER INFORMATION: wherein n is inosine
<220> FEATURE:
<221> NAME/KEY: misc_feature
<222> LOCATION: (12)..(12)
<223> OTHER INFORMATION: wherein n is inosine
<220> FEATURE:
<221> NAME/KEY: misc_feature
<222> LOCATION: (15)..(15)
<223> OTHER INFORMATION: wherein n is inosine
<220> FEATURE:
<221> NAME/KEY: misc_feature
<222> LOCATION: (18)..(18)
<223> OTHER INFORMATION: wherein n is inosine

<400> SEQUENCE: 28
uunuunuunu unuunuunuu                                               20

<210> SEQ ID NO 29
<211> LENGTH: 7
<212> TYPE: RNA
<213> ORGANISM: Artificial sequence
<220> FEATURE:
<223> OTHER INFORMATION: Synthetic oligonucleotide

<400> SEQUENCE: 29 uuguugu                                                              7

<210> SEQ ID NO 30
<211> LENGTH: 7
<212> TYPE: RNA
<213> ORGANISM: Artificial sequence
<220> FEATURE:
<223> OTHER INFORMATION: Synthetic oligonucleotide

<400> SEQUENCE: 30 uuauuau                                                              7

<210> SEQ ID NO 31
<211> LENGTH: 7
<212> TYPE: RNA
<213> ORGANISM: Artificial sequence
<220> FEATURE:
<223> OTHER INFORMATION: Synthetic oligonucleotide

<400> SEQUENCE: 31
``` ugugugu                                                                7

<210> SEQ ID NO 32
<211> LENGTH: 7
<212> TYPE: RNA
<213> ORGANISM: Artificial sequence
<220> FEATURE:
<223> OTHER INFORMATION: Synthetic oligonucleotide

<400> SEQUENCE: 32 ucucucu                                                                7

<210> SEQ ID NO 33
<211> LENGTH: 7
<212> TYPE: RNA
<213> ORGANISM: Artificial sequence
<220> FEATURE:
<223> OTHER INFORMATION: Synthetic oligonucleotide

<400> SEQUENCE: 33 uauauau                                                                7

<210> SEQ ID NO 34
<211> LENGTH: 7
<212> TYPE: RNA
<213> ORGANISM: Artificial sequence
<220> FEATURE:
<223> OTHER INFORMATION: Synthetic oligonucleotide

<400> SEQUENCE: 34 guaguag                                                                7

<210> SEQ ID NO 35
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 35
ccgagccgcc gccccc                                                     16

<210> SEQ ID NO 36
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 36
ccgagccgca uauccc                                                     16

<210> SEQ ID NO 37
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 37
ccgagccgcu auccc                                                      16

<210> SEQ ID NO 38
<211> LENGTH: 16
<212> TYPE: RNA
<213> ORGANISM: Artificial sequence

```
<220> FEATURE:
<223> OTHER INFORMATION: Synthetic oligonucleotide

<400> SEQUENCE: 38
ccgagccaua uauccc                                                16

<210> SEQ ID NO 39
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 39
ccgagccaua uauauc                                                16

<210> SEQ ID NO 40
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 40
ccgagccgaa uaaccc                                                16

<210> SEQ ID NO 41
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 41
ccgagccgca uaaccc                                                16

<210> SEQ ID NO 42
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 42
ccgagccgaa uacccc                                                16

<210> SEQ ID NO 43
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 43
ccgagccgcc uaaccc                                                16

<210> SEQ ID NO 44
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 44
ccgagccgaa uccccc                                                16
```

<210> SEQ ID NO 45
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 45
ccgagccgca uacccc                                                          16

<210> SEQ ID NO 46
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 46
ccgagccgca ucccc                                                           16

<210> SEQ ID NO 47
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 47
ccgagccgcc uaccc                                                           16

<210> SEQ ID NO 48
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 48
ccgagccgca uuaccc                                                          16

<210> SEQ ID NO 49
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 49
ccgagccgcu uaccc                                                           16

<210> SEQ ID NO 50
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 50
ccgagccgca auccc                                                           16

<210> SEQ ID NO 51
<211> LENGTH: 16
<212> TYPE: RNA
<213> ORGANISM: Artificial sequence
<220> FEATURE:
<223> OTHER INFORMATION: Synthetic oligonucleotide

```
<400> SEQUENCE: 51
ccgagccgcu auccc                                          16

<210> SEQ ID NO 52
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 52
ccgagccgca auccc                                          16

<210> SEQ ID NO 53
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 53
ccgagccgcu uaccc                                          16

<210> SEQ ID NO 54
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 54
ccgagccgca uuccc                                          16

<210> SEQ ID NO 55
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 55
ccgagccgcu auccc                                          16

<210> SEQ ID NO 56
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 56
ccgagccgaa ggcacc                                         16

<210> SEQ ID NO 57
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 57
ccgagccgac uuuacc                                         16

<210> SEQ ID NO 58
```

```
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 58
ccgagccgag uuuacc                                                        16

<210> SEQ ID NO 59
<211> LENGTH: 16
<212> TYPE: RNA
<213> ORGANISM: Artificial sequence
<220> FEATURE:
<223> OTHER INFORMATION: Synthetic oligonucleotide;
<220> FEATURE:
<221> NAME/KEY: misc_feature
<222> LOCATION: (10)..(10)
<223> OTHER INFORMATION: wherein n is thymine ribonucleotide

<400> SEQUENCE: 59
ccgagccgan uuuacc                                                        16

<210> SEQ ID NO 60
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 60
ccgagccgaa uuuacc                                                        16

<210> SEQ ID NO 61
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 61
ccgagccgac uguacc                                                        16

<210> SEQ ID NO 62
<211> LENGTH: 16
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: wherein n is thymine ribonucleotide

<400> SEQUENCE: 62
ccgagccgan uguacc                                                        16

<210> SEQ ID NO 63
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 63
ccgagccgaa uguacc                                                        16
```

```
<210> SEQ ID NO 64
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 64
ccgagccgau cuuacc                                                  16

<210> SEQ ID NO 65
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 65
ccgagccgau auuacc                                                  16

<210> SEQ ID NO 66
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 66
ccgagccgau guuacc                                                  16

<210> SEQ ID NO 67
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 67
ccgagccgag uucacc                                                  16

<210> SEQ ID NO 68
<211> LENGTH: 16
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: wherein n is thymine ribonucleotide

<400> SEQUENCE: 68
ccgagccgan uucacc                                                  16

<210> SEQ ID NO 69
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 69
ccgagccgau cucacc                                                  16

<210> SEQ ID NO 70
<211> LENGTH: 16
<212> TYPE: RNA
```

```
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (11)..(11)
<223> OTHER INFORMATION: wherein n is thymine ribonucleotide
<220> FEATURE:
<221> NAME/KEY: misc_feature
<222> LOCATION: (13)..(13)
<223> OTHER INFORMATION: wherein n is thymine ribonucleotide

<400> SEQUENCE: 70
ccgagccgau nunacc                                                      16

<210> SEQ ID NO 71
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 71
ccgagccgau uucacc                                                      16

<210> SEQ ID NO 72
<211> LENGTH: 16
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: wherein n is thymine ribonucleotide

<400> SEQUENCE: 72
ccgagccgau uunacc                                                      16

<210> SEQ ID NO 73
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 73
ccgagccgau uuaacc                                                      16

<210> SEQ ID NO 74
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 74
ccgagccgau ugcacc                                                      16

<210> SEQ ID NO 75
<211> LENGTH: 16
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (13)..(13)
<223> OTHER INFORMATION: wherein n is thymine ribonucleotide
```

```
<400> SEQUENCE: 75
ccgagccgau ucnacc                                              16

<210> SEQ ID NO 76
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 76
ccgagccgau ugaacc                                              16

<210> SEQ ID NO 77
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 77
ccgagccgag uucacc                                              16

<210> SEQ ID NO 78
<211> LENGTH: 16
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: wherein n is thymine ribonucleotide

<400> SEQUENCE: 78
ccgagccgan uucacc                                              16

<210> SEQ ID NO 79
<211> LENGTH: 16
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: wherein n is thymine ribonucleotide

<400> SEQUENCE: 79
ccgagccgan uucacc                                              16

<210> SEQ ID NO 80
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 80
ccgagccgaa uucacc                                              16

<210> SEQ ID NO 81
<211> LENGTH: 16
<212> TYPE: RNA
<213> ORGANISM: Artificial sequence
<220> FEATURE:
```

-continued

<223> OTHER INFORMATION: Synthetic oligonucleotide

<400> SEQUENCE: 81
ccgagccgag cucacc                                                       16

<210> SEQ ID NO 82
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 82
ccgagccgaa gguacc                                                       16

<210> SEQ ID NO 83
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 83
ccgagccgaa ggugcc                                                       16

<210> SEQ ID NO 84
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 84
ccgagccgaa gcuccc                                                       16

<210> SEQ ID NO 85
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 85
ccgagccgaa gauacc                                                       16

<210> SEQ ID NO 86
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 86
ccgagccgaa ggnccc                                                       16

<210> SEQ ID NO 87
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 87
ccgagccgaa gcuacc                                                       16

```
<210> SEQ ID NO 88
<211> LENGTH: 16
<212> TYPE: RNA
<213> ORGANISM: Artificial sequence
<220> FEATURE:
<223> OTHER INFORMATION: Synthetic oligonucleotide

<400> SEQUENCE: 88
ccgagccgaa gcugcc                                                      16

<210> SEQ ID NO 89
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 89
acccaucuau uauauaacuc                                                  20

<210> SEQ ID NO 90
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 90
tcgtcgtttt cggcggccgc cg                                               22

<210> SEQ ID NO 91
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 91
tcgtcgtttt tcggtcgttt t                                                21
```

US 7,662,949 B2

IMMUNOSTIMULATORY OLIGORIBONUCLEOTIDES

RELATED APPLICATION

This application claims priority under 35 USC §119 to U.S. Provisional Application No. 60/739,529, filed Nov. 25, 2005 and U.S. Provisional Application No. 60/778,989, filed Mar. 3, 2006, the entire contents of which are hereby incorporated by reference.

FIELD OF THE INVENTION

The invention relates generally to the field of immunology, and more particularly to immunostimulatory molecules. More specifically the invention relates to ribonucleic acid (RNA) molecules, including oligoribonucleotides, with immunostimulatory activity.

BACKGROUND OF THE INVENTION

Toll-like receptors (TLRs) are a family of highly conserved pattern recognition receptor (PRR) polypeptides that recognize pathogen-associated molecular patterns (PAMPs) and play a critical role in innate immunity in mammals. Currently at least ten family members, designated TLR1-TLR10, have been identified. The cytoplasmic domains of the various TLRs are characterized by a Toll-interleukin 1 receptor (TIR) domain. Medzhitov R et al. (1998) *Mol Cell* 2:253-8. Recognition of microbial invasion by TLRs triggers activation of a signaling cascade that is evolutionarily conserved in *Drosophila* and mammals. The TIR domain-containing adapter protein MyD88 has been reported to associate with TLRs and to recruit interleukin 1 receptor-associated kinase (IRAK) and tumor necrosis factor (TNF) receptor-associated factor 6 (TRAF6) to the TLRs. The MyD88-dependent signaling pathway is believed to lead to activation of NF-κB transcription factors and c-Jun $NH_2$ terminal kinase (Jnk) mitogen-activated protein kinases (MAPKs), critical steps in immune activation and production of inflammatory cytokines. For reviews, see Aderem A et al. (2000) *Nature* 406:782-87, and Akira S et al. (2004) *Nat Rev Immunol* 4:499-511.

A number of specific TLR ligands have been identified. Ligands for TLR2 include peptidoglycan and lipopeptides. Yoshimura A et al. (1999) *J Immunol* 163:1-5; Yoshimura A et al. (1999) *J Immunol* 163:1-5; Aliprantis A O et al. (1999) *Science* 285:736-9. Lipopolysaccharide (LPS) is a ligand for TLR4. Poltorak A et al. (1998) *Science* 282:2085-8; Hoshino K et al. (1999) *J Immunol* 162:3749-52. Bacterial flagellin is a ligand for TLR5. Hayashi F et al. (2001) *Nature* 410:1099-1103. Peptidoglycan has been reported to be a ligand not only for TLR2 but also for TLR6. Ozinsky A et al. (2000) *Proc Natl Acad Sci USA* 97:13766-71; Takeuchi O et al. (2001) *Int Immunol* 13:933-40. Recently certain low molecular weight synthetic compounds, the imidazoquinolines imiquimod (R-837) and resiquimod (R-848), were reported to be ligands of TLR7 and TLR8. Hemmi H et al. (2002) *Nat Immunol* 3:196-200; Jurk M et al. (2002) *Nat Immunol* 3:499.

Beginning with the recent discovery that unmethylated bacterial DNA and synthetic analogs thereof (CpG DNA) are ligands for TLR9 (Hemmi H et al. (2000) *Nature* 408:740-5; Bauer S et al. (2001) *Proc Natl Acad Sci USA* 98, 9237-42), it has been reported that ligands for certain TLRs include certain nucleic acid molecules. Recently it has been reported that certain types of RNA are immunostimulatory in a sequence-independent or sequence-dependent manner. Further, it has been reported that these various immunostimulatory RNAs stimulate TLR3, TLR7, or TLR8.

SUMMARY OF THE INVENTION

The invention relates generally to immunostimulatory oligoribonucleotides (ORN) that contain certain immunostimulatory RNA motifs, as well as to related immunostimulatory compositions containing such immunostimulatory ORN, and methods for the use of such immunostimulatory ORN and compositions. The immunostimulatory ORN of the invention are useful in any setting or application that calls for stimulating or augmenting an immune response. As disclosed below, the immunostimulatory ORN of the invention are of particular use in the preparation of pharmaceutical compositions, including adjuvants, vaccines, and other medicaments, for use in treating a variety of conditions, including infection, cancer, allergy, and asthma. The invention in certain aspects thus relates to immunostimulatory compositions that include immunostimulatory ORN of the invention, as well as methods of their use. Also as disclosed below, the immunostimulatory ORN and immunostimulatory compositions of the invention are of particular use in methods for activating an immune cell, vaccinating a subject, treating a subject having an immune system deficiency, treating a subject having an infection, treating a subject having autoimmune disease, treating a subject having cancer, treating a subject having an allergic condition, treating a subject having asthma, airway remodeling, promoting epitope spreading, and antibody-dependent cellular cytotoxicity (ADCC).

As disclosed in greater detail below, the immunostimulatory ORN of the invention are characterized by their inclusion of at least one sequence-dependent immunostimulatory RNA motif. The sequence-dependent immunostimulatory RNA motif generally is a short RNA sequence, although in certain embodiments the motif can also include a modification such as a modified internucleotide phosphate linkage, a modified nucleobase, a modified sugar, a nucleotide analog, or any combination thereof. As described in detail below, in one embodiment the immunostimulatory RNA motif occurs in the context of a longer immunostimulatory ORN of the invention. Also the immunostimulatory RNA motif may occur in the context of a chimeric DNA:RNA nucleic acid molecule.

The sequence-dependent immunostimulatory RNA motifs and immunostimulatory ORN incorporating such motifs are disclosed to be agonists for TLR8. More particularly, at least certain of the sequence-dependent immunostimulatory RNA motifs, immunostimulatory ORN, and immunostimulatory chimeric DNA:RNA nucleic acid molecules are disclosed to be agonists of TLR8 but not agonists of TLR7.

The immunostimulatory RNA motif according to some aspects of the invention is $N-U-R_1-R_2$.

N is a ribonucleotide and N does not include a U. In some embodiments N is Adenosine or Cytosine (C) or derivatives thereof.

U is Uracil or a derivative thereof.

R is a ribonucleotide wherein at least one of $R_1$ and $R_2$ is Adenosine (A) or Cytosine or derivatives thereof. R is not U unless $N-U-R_1-R_2$ includes at least two A.

The ORN of the invention includes at least one and in some embodiments more than one (i.e., 2, 3, or 4) immunostimulatory motifs, $N-U-R_1-R_2$. The ORN does not include a TLR7/8 motif. The ORN is preferably 4-100 in length and optionally includes at least one backbone modification.

$N-U-R_1-R_2$ may in some embodiments include at least 3 As or at least 2 Cs. Optionally, $N-U-R_1-R_2$ includes at least one G or C.

In some embodiments the ORN is not ACCCAUCUA-UUAUAUAACUC (SEQ ID NO:89).

In other embodiments the ORN motif is separated from a 5' ribonucleotide by a non-nucleotide linker. In yet other embodiments the ORN motif is separated from a 3' ribonucleotide by a non-nucleotide linker. Optionally, the ORN motif is separated from a 5' and 3' ribonucleotide by a non-nucleotide linker.

The ORN may further comprise a pharmaceutically acceptable carrier which optionally is a lipid carrier such as N-[1-(2,3-Dioleoyloxy)propyl]-N,N,Ntrimethylammonium-methyl-sulfate (DOTAP). In other embodiments the ORN is not complexed to DOTAP.

The ORN may be single stranded or double stranded.

In other embodiments the ORN includes at least one AU. In yet other embodiments the ORN includes at least one CU.

In some embodiments the ORN is one of the following:

```
A*U*A*G*G*C*A*C,                            (SEQ ID NO: 4)

G*C*C*A*C*C*G*A*G*C*C*G*A*A*U*A*U*          (SEQ ID NO: 11)
A*C*C,

A*U*A*U*A*U*A*U*A*U*A*U*A*U*A*              (SEQ ID NO: 12)
U*A*U,

U*U*A*U*U*A*U*U*A*U*U*A*U*U*A*U*U*          (SEQ ID NO: 13)
A*U*U,

A*A*U*A*A*U*A*A*U*A*A*U*A*A*U*A*            (SEQ ID NO: 16)
U*A*A,

A*A*A*U*A*A*A*U*A*A*A*U*A*A*A*U*A*          (SEQ ID NO: 17)
A*A*U,

A*A*A*A*U*A*A*A*A*U*A*A*A*A*U*A*            (SEQ ID NO: 18)
A*A*U,

C*U*A*C*U*A*C*U*A*C*U*A*C*U*A*C*U*          (SEQ ID NO: 24)
A*C*U,

U*U*A*U*U*A*U,                              (SEQ ID NO: 30)

U*A*U*A*U*A*U,                              (SEQ ID NO: 33)

C*C*G*A*G*C*C*G*C*A*U*U*A*C*C,              (SEQ ID NO: 48)

C*C*G*A*G*C*C*G*A*U*U*G*A*A*C*C,            (SEQ ID NO: 76)

C*C*G*A*G*C*C*G*A*A*U*A*C*C*C*C,            (SEQ ID NO: 42)

C*C*G*A*G*C*C*A*U*A*U*A*U*A*U*C,            (SEQ ID NO: 39)

C*C*G*A*G*C*C*G*A*U*A*U*U*A*C*C,            (SEQ ID NO: 65)

C*C*G*A*G*C*C*G*A*A*U*C*C*C*C,              (SEQ ID NO: 44)

C*C*G*A*G*C*C*G*C*C*U*A*C*C*C*C,            (SEQ ID NO: 47)

C*C*G*A*G*C*C*A*U*A*U*A*U*C*C*C,            (SEQ ID NO: 38)

C*C*G*A*G*C*C*G*C*U*A*U*A*C*C*C,            (SEQ ID NO: 37)

C*C*G*A*G*C*C*G*A*A*U*A*A*C*C*C,            (SEQ ID NO: 40)

C*C*G*A*G*C*C*G*C*U*A*U*C*C*C*C,            (SEQ ID NO: 55)

C*C*G*A*G*C*C*G*A*A*G*G*U*A*C*C,            (SEQ ID NO: 82)

C*C*G*A*G*C*C*G*A*A*G*A*U*A*C*C,            (SEQ ID NO: 85)

C*C*G*A*G*C*C*G*A*A*U*G*U*A*C*C,            (SEQ ID NO: 63)

C*C*G*A*G*C*C*G*C*C*U*A*A*C*C*C,            (SEQ ID NO: 43)

C*C*G*A*G*C*C*G*C*A*U*A*U*C*C*C,            (SEQ ID NO: 36)

C*C*G*A*G*C*C*G*A*A*G*C*U*A*C*C,            (SEQ ID NO: 87)

C*C*G*A*G*C*C*G*C*A*U*A*C*C*C*C,            (SEQ ID NO: 45)

C*C*G*A*G*C*C*G*C*A*U*A*A*C*C*C,            (SEQ ID NO: 41)

C*C*G*A*G*C*C*G*A*A*G*G*U*G*C*C,            (SEQ ID NO: 83)

C*C*G*A*G*C*C*G*C*A*U*C*C*C*C*C,            (SEQ ID NO: 46)

C*C*G*A*G*C*C*G*A*A*G*C*U*G*C*C,            (SEQ ID NO: 88)

C*C*G*A*G*C*C*G*C*C*G*C*C*C*C*C,            (SEQ ID NO: 35)

C*C*G*A*G*C*C*G*A*A*G*C*U*C*C*C,            (SEQ ID NO: 84)
or

C*C*G*A*G*C*C*G*A*A*G*G*C*A*C*C.            (SEQ ID NO: 56)
```

The ORN specifically excludes TLR7/8 motifs. A TLR7/8 motif may include for example a ribonucleotide sequence selected from (i)   5'-C/U-U-G/U-U-3', (ii)  5'-R-U-R-G-Y-3', (iii) 5'-G-U-U-G-B-3', (iv)  5'-G-U-G-U-G/U-3', and (v)   5'-G/C-U-A/C-G-G-C-A-C-3', wherein C/U is cytosine (C) or uracil (U), G/U is guanine (G) or U, R is purine, Y is pyrimidine, B is U, G, or C, G/C is G or C, and A/C is adenine (A) or C.

In various embodiments 5'-C/U-U-G/U-U-3' is CUGU, CUUU, UUGU, or UUUU.

In various embodiments 5'-R-U-R-G-Y-3' is GUAGU, GUAGC, GUGGU, GUGGC, AUAGU, AUAGC, AUGGU, or AUGGC. In one embodiment the base sequence is GUAGUGU.

In various embodiments 5'-G-U-U-G-B-3' is GUUGU, GUUGG, or GUUGC.

In various embodiments 5'-G-U-G-U-G/U-3' is GUGUG or GUGUU. In one embodiment the base sequence is GUGU-UUAC.

In various embodiments 5'-G/C-U-A/C-G-G-C-A-C-3' is GUAGGCAC, GUCGGCAC, CUAGGCAC, or CUCG-GCAC.

In one aspect the invention provides an immunostimulatory composition including an immunostimulatory ORN of the invention and an adjuvant. In various embodiments the adjuvant is an adjuvant that creates a depot effect, an immune-stimulating adjuvant, or an adjuvant that creates a depot effect and stimulates the immune system. In one embodiment the immunostimulatory composition according to this aspect of the invention is a conjugate of the immunostimulatory ORN and the adjuvant. In one embodiment according to this aspect of the invention the immunostimulatory ORN is covalently linked to the adjuvant. In other embodiments they are not conjugated. In one embodiment the adjuvant is an agonist of TLR9. In one embodiment the adjuvant is an immunostimulatory CpG nucleic acid.

The compositions of the invention can optionally include an antigen. Thus in one aspect the invention provides a vaccine, wherein the vaccine includes an immunostimulatory ORN of the invention and an antigen. In one aspect the invention provides a vaccine that includes a conjugate of an immunostimulatory ORN of the invention and an antigen. In one embodiment the conjugate according to this aspect of the invention includes the immunostimulatory ORN covalently linked to the antigen. In other embodiments they are not conjugated. In various embodiments the antigen can be an antigen per se. The antigen can be any antigen, including a cancer antigen, a microbial antigen, or an allergen.

In one aspect the invention provides an immunostimulatory composition including a conjugate of an immunostimulatory ORN of the invention and a lipophilic moiety. In one embodiment the immunostimulatory ORN is covalently linked to the lipophilic moiety. In one embodiment the lipophilic moiety is selected from the group consisting of cholesteryl, palmityl, and fatty acyl. In one embodiment the lipophilic moiety is a derivative of cholesterol, e.g., cholesteryl.

In one embodiment the immunostimulatory ORN includes at least one deoxyribonucleotide. The at least one deoxyribonucleotide generally can occur anywhere outside of the immunostimulatory RNA motif. In various embodiments the at least one deoxyribonucleotide is 1, 2, 3, 4, 5, 6, 7, 8, 9, 10, 11, 12, 13, 14, 15, 16, 17, 18, 19, 20, 21, 22, 23, or 24 consecutive deoxyribonucleotides. Immunostimulatory ORN including nonconsecutive deoxyribonucleotides are also contemplated by the invention. In various embodiment the at least one deoxyribonucleotide is a 5' end, a 3' end, or both a 5' end and a 3' end of the immunostimulatory ORN. The at least one deoxyribonucleotide also corresponds to a DNA portion of a chimeric DNA:RNA molecule. In one embodiment a DNA component of the chimeric DNA:RNA molecule includes a CpG nucleic acid, i.e., a TLR9 agonist. In one embodiment the DNA and RNA portions of the chimeric DNA:RNA molecule are covalently linked through an internucleotide phosphate bond. In another embodiment the DNA and RNA portions of the chimeric DNA:RNA molecule are covalently linked through a linker, e.g., a non-nucleotidic linker.

In one aspect the invention provides an immunostimulatory composition that includes a covalently closed, partially single-stranded, dumbbell-shaped nucleic acid molecule, wherein at least one single-stranded portion of the molecule includes an immunostimulatory RNA motif of the invention.

In one aspect the invention provides a pharmaceutical composition including the composition of any of the foregoing aspects of the invention, in association with a delivery vehicle chosen from a cationic lipid, a liposome, a cochleate, a virosome, an immune-stimulating complex (ISCOM), a microparticle, a microsphere, a nanosphere, a unilamellar vesicle (LUV), a multilamellar vesicle, an oil-in-water emulsion, a water-in-oil emulsion, an emulsome, and a polycationic peptide, and, optionally, a pharmaceutically acceptable carrier. In one embodiment according to this aspect of the invention the pharmaceutical composition includes an antigen.

The ORN may be formulated in a nebulizer or an inhaler, such as a metered dose inhaler or a powder inhaler. In some embodiments the ORN further includes an additional composition such as a chemotherapeutic agent, an anti-viral agent or a pharmaceutically acceptable carrier. The pharmaceutically acceptable carrier may be formulated for injection or mucosal administration.

Further according to these and other aspects of the invention, in various embodiments the immunostimulatory ORN can optionally include at least one 5'-5' internucleotide linkage, at least one 3'-3' internucleotide linkage, at least one 5'-5' internucleotide linkage that includes a linker moiety, at least one 3'-3' internucleotide linkage that includes a linker moiety, or any combination thereof. The linker moiety in one embodiment is a non-nucleotidic linker moiety.

Further still according to these and other aspects of the invention, in various embodiments the immunostimulatory ORN can optionally include at least one 2'-2' internucleotide linkage, at least one 2'-3' internucleotide linkage, at least 2'-5' internucleotide linkage, or any combination thereof. In a preferred embodiment the at least one 2'-2' internucleotide linkage, at least one 2'-3' internucleotide linkage, or at least 2'-5' internucleotide linkage occurs outside of the immunostimulatory RNA motif.

Also according to these and other aspects of the invention, the immunostimulatory ORN in one embodiment includes at least one multiplier unit. Accordingly, in certain embodiments the immunostimulatory ORN of the invention can have a branched structure. Branched compositions can include 3'-5', 5'-5', 3'-3', 2'-2', 2'-3', or 2'-5' internucleotide linkages, in any combination. In one embodiment the immunostimulatory ORN includes at least two multiplier units, resulting in a so-called dendrimer. In addition, in certain embodiments the immunostimulatory ORN of the invention may include two or more immunostimulatory RNA motifs, arranged for example in tandem along a linear ORN, on different arms of a branched structure, or both in tandem along a linear ORN and on different arms of a branched structure. Branched structures, including dendrimers, can optionally include at least one immunostimulatory CpG nucleic acid, for example as a separate arm of a branched structure.

Further according to these and other aspects of the invention, in one embodiment the immunostimulatory ORN does not include a CG DNA or RNA dinucleotide.

In one aspect the invention provides a method for down-regulating immunosuppressive CD4+ regulatory (Treg) cells. The method according to this aspect of the invention includes the step of contacting a CD4+ Treg cell with a composition containing a TLR8-specific immunostimulatory ORN of the invention in an effective amount to reduce the inhibitory effect of the CD4+ Treg cell. In one embodiment the composition includes a TLR8-specific ORN and an immunostimulatory CpG nucleic acid, wherein the TLR8-specific ORN and the immunostimulatory CpG nucleic acid are not linked. In one embodiment the composition includes a TLR8-specific ORN and an immunostimulatory CpG nucleic acid, wherein the TLR8-specific ORN and the immunostimulatory CpG nucleic acid are present as a conjugate.

In another aspect the invention provides a method for modulating an immune response in a subject The method according to this aspect of the invention includes the step of administering to a subject an effective amount of a composition of the invention. In some embodiments the ORN may be delivered to the subject to treat autoimmune disease or airway remodeling in the subject. The ORN may be administered with or without an antigen to the subject. Optionally the ORN is delivered by a route such as oral, nasal, sublingual, intravenous, subcutaneous, mucosal, respiratory, direct injection, and dermally. The ORN may be delivered to the subject in an effective amount to induce cytokine expression, such as TNFα, IL-10, IL-6, IFN-γ, MCP1, and IL-12.

In one aspect the invention provides a method of vaccinating a subject. The method according to this aspect of the invention includes the step of administering to the subject an antigen and an immunostimulatory ORN of the invention.

In one aspect the invention provides a method for treating a subject having or at risk of having an infectious disease. The method according to this aspect of the invention includes the step of administering to the subject an effective amount of a composition of the invention. In one embodiment the method includes the step of administering to the subject an effective amount of an immunostimulatory ORN of the invention. In one embodiment the subject has a viral infection. The viral infection may be, for example, hepatitis B or hepatitis C. An anti-viral agent may be also administered to the subject. Optionally the anti-viral agent is linked to the ORN.

In one aspect the invention provides a method for treating a subject having or at risk of having a cancer. The method according to this aspect of the invention includes the step of administering to the subject an effective amount of a composition of the invention. In one embodiment the method includes the step of administering to the subject an effective amount of an immunostimulatory ORN of the invention. In one embodiment a chemotherapeutic or radiation is also administered to the subject.

In one aspect the invention provides a method for treating a subject having or at risk of having a cancer. The method according to this aspect of the invention includes the step of administering to the subject an effective amount of a composition containing a TLR8-specific immunostimulatory ORN of the invention to reduce the inhibitory effect of CD4+ Treg cells. In one embodiment the composition includes a TLR8-specific ORN and an immunostimulatory CpG nucleic acid, wherein the TLR8-specific ORN and the immunostimulatory CpG nucleic acid are not linked. In one embodiment the composition includes a TLR8-specific ORN and an immunostimulatory CpG nucleic acid, wherein the TLR8-specific ORN and the immunostimulatory CpG nucleic acid are present as a conjugate.

In one aspect the invention provides a method for treating a subject having or at risk of having an allergic condition. The method according to this aspect of the invention includes the step of administering to the subject an effective amount of a composition of the invention. In one embodiment the method includes the step of administering to the subject an effective amount of an immunostimulatory ORN of the invention. In one embodiment the subject has allergic rhinitis.

In one aspect the invention provides a method for treating a subject having or at risk of having asthma. The method according to this aspect of the invention includes the step of administering to the subject an effective amount of a composition of the invention. In one embodiment the method includes the step of administering to the subject an effective amount of an immunostimulatory ORN of the invention. In one embodiment the asthma is asthma exacerbated by viral infection. The ORN may be administered with or without an allergen.

In another aspect the invention provides a method for treating a subject having airway remodeling. The method according to this aspect of the invention includes the step of administering to the subject an effective amount of an immunostimulatory ORN of the invention.

In one aspect the invention provides a method for increasing antibody-dependent cellular cytotoxicity (ADCC). The method according to this aspect of the invention includes the step of administering to a subject in need of increased ADCC an effective amount of an immunostimulatory ORN of the invention and an antibody to increase ADCC. In one embodiment the antibody is an antibody specific for a cancer antigen or other antigen expressed by a cancer cell. In one embodiment the antibody is an IgG antibody.

The invention in one aspect provides a method for enhancing epitope spreading. The method according to this aspect of the invention includes the sequential steps of contacting a cell of the immune system with an antigen and subsequently contacting the cell with at least two doses of an immunostimulatory ORN of the invention. In one embodiment the method is performed in vivo. The method in one embodiment includes the steps of administering to a subject a vaccine that includes an antigen and an adjuvant and subsequently administering to the subject at least two doses of an immunostimulatory ORN of the invention, in an effective amount to induce multiple epitope-specific immune responses. The method in one embodiment involves applying a therapeutic protocol which results in immune system antigen exposure in a subject, followed by administering at least two doses of an immunostimulatory ORN of the invention, in an effective amount to induce multiple epitope-specific immune responses. In various embodiments the therapeutic protocol is surgery, radiation, chemotherapy, other cancer medicaments, a vaccine, or a cancer vaccine. In one embodiment the at least two doses of the immunostimulatory ORN are administered at least one day to one week apart from one another. In one embodiment the at least two doses of the immunostimulatory ORN are administered at least one week to one month apart from one another. In one embodiment the at least two doses of the immunostimulatory ORN are administered at least one month to six months apart from one another.

In one aspect the invention is a method for stimulating production of a pro-inflammatory cytokine, by contacting a TLR8 expressing cell with an RNA oligonucleotide (ORN) comprising: N-U-$R_1$-$R_2$, wherein N is a ribonucleotide and N does not include a U, U is Uracil or a derivative thereof, and R is a ribonucleotide wherein at least one of $R_1$ and $R_2$ is Adenosine (A) or Cytosine or derivatives thereof and wherein R is not U unless N-U-$R_1$-$R_2$ includes at least two A, wherein the ORN does not include a TLR7/8 motif and wherein the ORN is 4-100 in length, in an effective amount to stimulate pro-inflammatory cytokine production and wherein IFN-α production in response to the ORN is not induced significantly relative to background. In some embodiments the IFN-α production in response to the ORN is less than 300 pg/ml. In one embodiment the ORN is not ACCCAUCUAUUAUAUAACUC (SEQ ID NO:89). The ORN may or may not be complexed to N-[1-(2,3-Dioleoyloxy)propyl]-N,N,Nt-rimethylammoniummethyl-sulfate (DOTAP).

In some embodiments the TLR8 expressing cell is a monocyte or a mDC. In yet other embodiments the TLR8 expressing cell is in vitro or in vivo.

These and other features of the invention will be described in further detail in connection with the detailed description of the invention.

BRIEF DESCRIPTION OF THE DRAWINGS

In FIG. 1c human PBMC were stimulated with 0.2 μM of the indicated ORN complexed to DOTAP (2.2 μg/ml) or with R-848 (2 μM). After 16 h supernatants were harvested and IFN-alpha (left panel) and TNF-alpha (right panel) were measured by ELISA. Data shown are mean (±SEM) of 3 donors.

FIG. 6 is a set of graphs comparing titration curves for ORN with TLR8 (SEQ ID NO:13) or TLR7/8 (SEQ ID NO:21) for PBMC, isolated pDC or isolated monocytes of 3 Blood Donors. The cells were stimulated with ORN (4 concentrations, starting from 1 µM with 1/4 dilution) complexed to DOTAP (starting from 25 µg/ml with 1/4 dilutions). After 16 hours the supernatents were harvested and cytokine production measured by Luminex technologies. The graphs show the percent SEQ ID NO:21 (at 0.3 µM) cytokine production.

FIGS. 9a and 9b show fold induction of NFκB-luciferase after stimulus. FIG. 9c shows fold induction of NFκB-luciferase after stimulus in the presence of inhibitors. FIG. 9d shows stimulation of IP-10 after stimulus as measured by luciferase assay.

FIG. 10 is a series of graphs showing surface marker expression upon human pDC stimulation with AU-rich or GU-rich ORN. CD123+ purified pDC (FIGS. 10a and 10b) or isolated monocytes (FIG. 10c) were incubated with 1 µM ORN complexed to 25 µg/ml DOTAP or DOTAP alone (FIG. 10a) or indicated amounts of ORN complexed to DOTAP or DOTAP alone (FIGS. 10b-10c). After 16 h cells were harvested and stained with CD123, CD11c and HLA-DR antibodies (FIGS. 10a and 10b) or CD14 and CD19 (FIG. 10c). Cell surface marker activation was measured by CD86 (FIGS. 10a and 10b) or CD80 (FIG. 10c) expression. FIG. 10a shows FACS analysis demonstrating that AU-rich ORN (SEQ ID NO:13) and GU-rich ORN (SEQ ID NO:21) show differences in CD86 surface marker expression upon pDC stimulation. FIG. 10b is a graph illustrating that CD86 surface marker expression upon human pDC stimulation is dose-dependent. FIG. 10c is a graph showing that AU-rich ORN (SEQ ID NO:13) and GU-rich ORN (SEQ ID NO:21) show no difference in CD80 surface marker expression upon human PBMC (data not shown) and CD14-positive cell stimulation.

FIG. 11 is a set of bar graphs showing differences between TLR8 ORN (SEQ ID NO:13) and TLR7/8 ORN (SEQ ID NO:21). SEQ ID NO:5 ORN was used as a control. Bovine PBMC were incubated with either 10 µg/ml ORN (HD) or 2.5 µg/ml ORN (LD) for 48 hours. Supernatants were collected and analyzed by ELISA. FIGS. 11a-c show the level of IL-12, IFN-γ, and TNF-alpha, respectively.

DETAILED DESCRIPTION OF THE INVENTION

Figure 1:
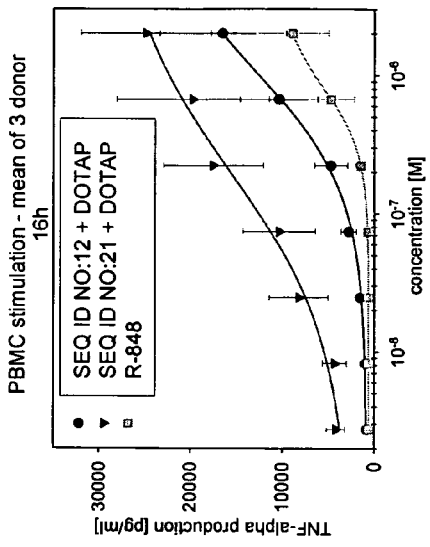
FIG. 1 is a set of graphs depicting ORN induced cytokine production upon PBMC stimulation. By measuring IFN-alpha and TNF-alpha cytokine production differences between TLR8 and TLR7/8 motifs were seen. Human PBMC were stimulated with the indicated ORN (2 μM with 1/3 dilution) complexed to DOTAP (25 μg/ml 1/3 dilution) or with R-848 (2 μM with 1/3 dilution) in a full titration curve. After 16 h supernatants were harvested and IFN-alpha (FIG. 1a) and TNF-alpha (FIG. 1b) were measured by ELISA. Data show the mean of three blood donors of a least three independent experiments. DOTAP alone did not show an effect. The ORN are complexed to DOTAP, R-848 is not complexed. DOTAP alone is a control.
Figure 1:
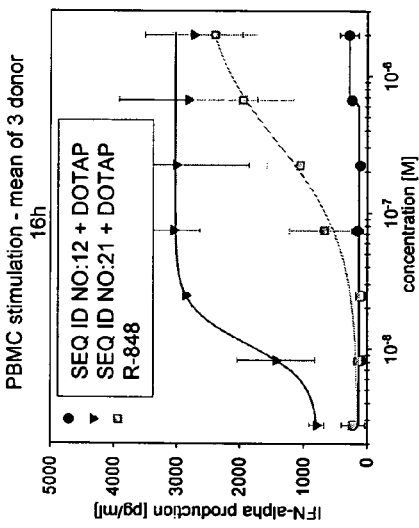
Figure 1:
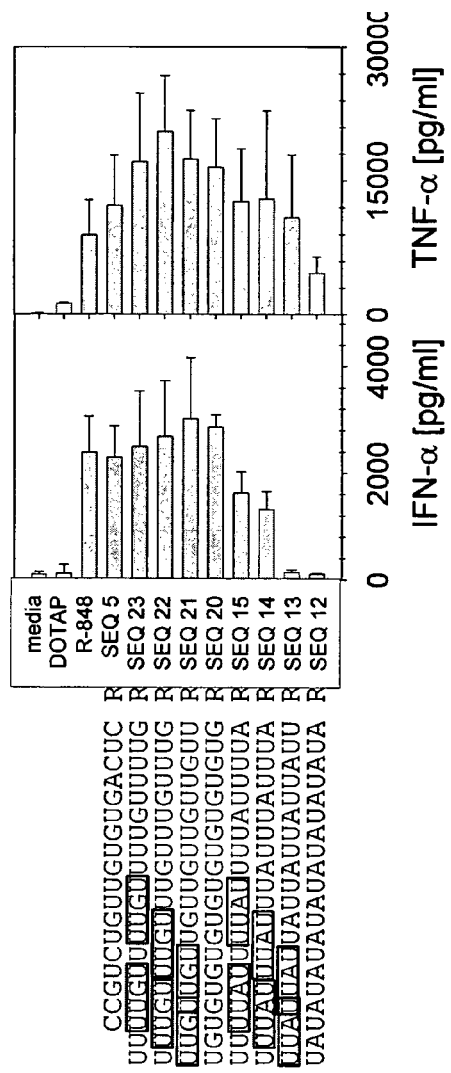

The invention relates in part to the discovery by the inventors of a number of sequence-specific immunostimulatory RNA motifs. It has now been discovered that molecules containing an immunostimulatory RNA motif are, alone or in combination with certain other components, important immunostimulatory compounds that find use in a number of methods for treating subjects having or at risk of having a condition in which it would be advantageous to induce, augment, or redirect an immune response. As used herein, in one embodiment an immunostimulatory composition of the invention is an immunostimulatory ORN of the invention.

It has been discovered that certain sequence-specific RNA motifs are immunostimulatory, acting through TLR8, as opposed to other motifs (GU rich and CU rich) that act on TLR 7 and TLR8. RNA Oligonucleotides (ORN), preferably containing AU-rich sequences, stimulate an immune response through TLR8. Differences between IFN-alpha, TNF-alpha, IFN-gamma and IL-12 production have been observed in these distinct classes of ORN, e.g. ORN containing AU- and GU-containing repetitions. Interestingly, the immunostimulatory ORN of the invention have been found to produce a strong pro-inflammatory cytokine response, with the exception of IFN-alpha and IFN-alpha related molecules. IFN-alpha production is diminished or lacking upon stimulation with these novel ORN.

The immunostimulatory RNA motif according to some aspects of the invention is N-U-$R_1$-$R_2$.

N is a ribonucleotide and N does not include a U. In some embodiments N is Adenosine or Cytosine (C) or derivatives thereof.

U is Uracil or a derivative thereof.

R is a ribonucleotide wherein at least one of $R_1$ and $R_2$ is Adenosine (A) or Cytosine or derivatives thereof. R is not U unless N-U-$R_1$-$R_2$ includes at least two A.

The ORN of the invention includes at least one and in some embodiments more than one (i.e., 2, 3, or 4) immunostimulatory motifs, N-U-$R_1$-$R_2$. The ORN does not include a TLR7/8 motif.

The ORN is an oligonucleotide. Optionally, the oligonucleotide is 4-100 in length. The ORN may also be, for instance, 8-40, 15-25 or 20-30 nucleotides in length. Optionally the ORN includes at least one backbone modification.

N-U-$R_1$-$R_2$ may in some embodiments include at least 3 As or at least 2 Cs. Optionally, N-U-$R_1$-$R_2$ includes at least one G or C.

In some embodiments the ORN is not ACCCAUCUAUUAUAUAACUC (SEQ ID NO:89).

The ORN may further comprise a pharmaceutically acceptable carrier which optionally is a lipid carrier such as N-[1-(2,3-Dioleoyloxy)propyl]-N,N,Ntrimethylammonium-methyl-sulfate (DOTAP). In other embodiments the ORN is not complexed to DOTAP. In other embodiments the pharmaceutically acceptable carrier may be a peptide such as a polycationic peptide. Polycationic peptides include, for instance, multiple poly-lysines, poly-arginines and poly-peptides containing more than 50% of basic amino acids, especially arginine or lysine residues, in a range of more than 5, especially more than 8 amino acid residues or mixtures thereof and may, for instance, include derivatives of a naturally occurring insect antimicrobial proteins.

In other embodiments the ORN includes at least one AU.

In addition to being sequence-specific, the immunostimulatory RNA motifs are effective as single-stranded RNA, partially double-stranded RNA, or wholly double-stranded RNA.

Clear differences between production of IFN-alpha and IFN-alpha related molecules and other pro-inflammatory cytokines such as TNF-alpha, IFN-gamma, IL-10, IL-6 and IL-12 were observed for ORN of the invention and ORN having a TLR7/8 motif, i.e. GU-containing repetitions. The ORN of the invention having a N-U-$R_1$-$R_2$ motif, for example those containing AU or AUU repetitions (SEQ ID NO:12, SEQ ID NO:13) revealed no IFN-alpha cytokine production upon PBMC and pDC stimulation. In contrast ORN having three and more U in a row (SEQ ID NO:14, SEQ ID NO:15) induced IFN-alpha production, despite the presence of As. Interestingly, using the same set of ORN but with G exchanged for A strong IFN-alpha production upon PBMC stimulation was observed. The data presented herein strongly suggest the existence of two different ORN classes: one acting on cells expressing TLR8 such as monocytes and mDCs (SEQ ID NO:12, SEQ ID NO:13, SEQ ID NO:16-SEQ ID NO:18), the ORN containing N-U-$R_1$-$R_2$ motifs of the invention and another one acting on cells expressing both TLR7/8 such as monocytes, mDCs and pDCs (SEQ ID NO:14, SEQ ID NO:15, SEQ ID NO:19-SEQ ID NO:23) containing CU, GU and GUU sequences.

Thus, the ORN of the invention have the ability to induce an immune response without inducing significant amounts of IFN-alpha or IFN-alpha related molecules relative to background. A significant amount of IFN-alpha or IFN-alpha related molecules relative to background is preferably less than 20% change in levels of IFN-alpha or IFN-alpha related molecules relative to background. In some embodiments it is less than 15%, 10%, 9%, 8%, 7%, 6%, 5%, 4%, 3%, 2%, or 1%. In other embodiments the amount of IFN-alpha or related molecules that is induced is equivalent to background or less than background levels. In yet other embodiments the amount of IFN-alpha induced by the ORN of the invention is less than or equal to 20% of the IFN-alpha induced by a TLR7/8 ORN. The amount of IFN-alpha induced by the ORN of the invention may optionally be less than 300 pg/ml in an in vitro assay or may have an EC50 of greater than 1.5 μM.

An IFN-alpha related molecule, as used herein, is a cytokine or factor that is related to the expression of IFN-alpha. These molecules include but are not limited to MIP1-beta, IP-10 and MIP1-alpha.

It was recently reported that CD4+ Treg cells express TLR8 and that TLR8 signaling in these cells reduces or reverses their immunoinhibitory function. Peng G et al. (2005) *Science* 309:1380-4. Increased populations of CD4+ Treg cells have been observed in patients with various types of cancers, where immunosuppression may contribute to the immune "escape" and unregulated growth of these cancers. Reversal of Treg-mediated suppression thus would be expected to be beneficial in treating cancer.

The ORN specifically exclude TLR7/8 motifs. It has been discovered that TLR7/8 motifs can produce dominant results that mask the unique immunostimulatory properties of the ORN of the invention. A TLR7/8 motif may include, for example, a ribonucleotide sequence such as 5'-C/U-U-G/U-U-3',5'-R-U-R-G-Y-3',5'-G-U-U-G-B-3', 5'-G-U-G-U-G/U-3', or 5'-G/C-U-A/C-G-G-C-A-C-3'. C/U is cytosine (C) or uracil (U), G/U is guanine (G) or U, R is purine, Y is pyrimidine, B is U, G, or C, G/C is G or C, and A/C is adenine (A) or C. The 5'-C/U-U-G/U-U-3' may be CUGU, CUUU, UUGU, or UUUU. In various embodiments 5'-R-U-R-G-Y-3' is GUAGU, GUAGC, GUGGU, GUGGC, AUAGU, AUAGC, AUGGU, or AUGGC. In one embodiment the base sequence is GUAGUGU. In various embodiments 5'-G-U-U-G-B-3' is GUUGU, GUUGG, or GUUGC. In various embodiments 5'-G-U-G-U-G/U-3' is GUGUG or GUGUU. In one embodiment the base sequence is GUGUUUAC. In various other embodiments 5'-G/C-U-A/C-G-G-C-A-C-3' is GUAGGCAC, GUCGGCAC, CUAGGCAC, or CUCGGCAC.

The invention relates generally to immunostimulatory oligoribonucleotides that include one or more immunostimulatory RNA motifs, immunostimulatory compositions containing one or more immunostimulatory ORN of the invention, and methods for use of the immunostimulatory ORN and immunostimulatory compositions of the invention.

As used herein, the terms "RNA" and equivalently "natural RNA" shall refer to two or more ribonucleotides (i.e., molecules each comprising a ribose sugar linked to a phosphate group and to a purine or pyrimidine nucleobase (e.g., guanine, adenine, cytosine, or uracil)) covalently linked together by 3'-5' phosphodiester linkage(s).

The immunostimulatory RNA motif can occur at an end of the immunostimulatory ORN (when the immunostimulatory ORN has free ends). For example, an immunostimulatory ORN with free ends and the immunostimulatory RNA motif positioned at an end of the immunostimulatory ORN can be represented as $X_aM$ or as $MX_b$, where M represents the immunostimulatory RNA motif and each of $X_a$ and $X_b$ independently represents one or more identical or nonidentical nucleotides of the immunostimulatory ORN exclusive of the immunostimulatory RNA motif.

Alternatively, the immunostimulatory RNA motif can be flanked on both of its ends by at least one additional nucleotide of the immunostimulatory ORN, whether the immunostimulatory ORN has free ends or not. For example, an immunostimulatory ORN with free ends and nucleotides flanking the immunostimulatory RNA motif can be represented as $X_a M X_b$, where M represents the immunostimulatory RNA motif and each of $X_a$ and $X_b$ independently represents one or more identical or nonidentical nucleotides of the immunostimulatory ORN exclusive of the immunostimulatory RNA motif.

In different embodiments the immunostimulatory ORN including the immunostimulatory RNA motif can include a single motif or more than one immunostimulatory RNA motif. It is believed that there may be an advantage to having two or more immunostimulatory RNA motifs in a single immunostimulatory ORN, for example if the motifs are spaced such that the immunostimulatory ORN can engage two or more TLRs. For example, the immunostimulatory ORN could engage two or more TLR8 receptors thereby amplifying or modifying the resulting immunostimulatory effect.

When the immunostimulatory ORN includes more than one immunostimulatory RNA motif, the immunostimulatory ORN can be represented in one embodiment as $M_1 X M_2$, wherein $M_1$ and $M_2$ each independently represent an immunostimulatory RNA motif and X represents one or more identical or nonidentical nucleotides of the immunostimulatory ORN exclusive of the immunostimulatory RNA motifs. In one embodiment X includes a non-nucleotidic linker as described herein. In one embodiment X includes a branching unit as described herein.

When there is more than one immunostimulatory RNA motif in the immunostimulatory ORN, the motifs generally can occur at any position along the immunostimulatory ORN. For example, when there are two motifs, they may each occur at an end of the immunostimulatory ORN. Alternatively, one motif can occur at an end and one motif can be flanked on both of its ends by at least one additional nucleotide of the immunostimulatory ORN. In yet another embodiment each motif can be flanked on both of its ends by at least one additional nucleotide of the immunostimulatory ORN.

Immunostimulatory ORN include, but are not limited to the following, shown 5' to 3' reading left to right:

In some embodiments the ORN is one of the active ORN shown in Tables 1 and 2 below, such as the following:

| Sequence | SEQ ID NO |
|---|---|
| U*U*A*G*G*C*A*C, | (SEQ ID NO: 2) |
| A*U*A*G*G*C*A*C, | (SEQ ID NO: 4) |
| G*C*C*A*C*C*G*A*G*C*C*G*A*A*U*A*U*A*C*C, | (SEQ ID NO: 11) |
| A*U*A*U*A*U*A*U*A*U*A*U*A*U*A*U*A*U*A*U*A, | (SEQ ID NO: 12) |
| U*U*A*U*U*A*U*U*A*U*U*A*U*U*A*U*U*A*U*U, | (SEQ ID NO: 13) |
| A*A*U*A*A*U*A*U*A*A*U*A*A*U*A*A*U*A*A, | (SEQ ID NO: 16) |
| A*A*A*U*A*A*A*U*A*A*A*U*A*A*A*U*A*A*A*U, | (SEQ ID NO: 17) |
| A*A*A*A*U*A*A*A*A*U*A*A*A*A*U*A*A*A*A*U, | (SEQ ID NO: 18) |
| C*U*A*C*U*A*C*U*A*C*U*A*C*U*A*C*U*A*C*U, | (SEQ ID NO: 24) |
| U*U*A*U*U*A*U, | (SEQ ID NO: 30) |
| U*A*U*A*U*A*U, | (SEQ ID NO: 33) |
| C*C*G*A*G*C*C*G*C*A*U*U*A*C*C, | (SEQ ID NO: 48) |
| C*C*G*A*G*C*C*G*A*U*U*G*A*A*C, | (SEQ ID NO: 76) |
| C*C*G*A*G*C*C*G*A*A*U*A*C*C*C, | (SEQ ID NO: 42) |
| C*C*G*A*G*C*C*A*U*A*U*A*U*A*U*C, | (SEQ ID NO: 39) |
| C*C*G*A*G*C*C*G*A*U*A*U*U*A*C, | (SEQ ID NO: 65) |
| C*C*G*A*G*C*C*G*A*A*U*C*C*C*C, | (SEQ ID NO: 44) |
| C*C*G*A*G*C*C*G*C*U*A*C*C*C, | (SEQ ID NO: 47) |
| C*C*G*A*G*C*C*A*U*A*U*A*U*C*C*C, | (SEQ ID NO: 38) |
| C*C*G*A*G*C*C*G*C*U*A*U*A*C*C*C, | (SEQ ID NO: 37) |
| C*C*G*A*G*C*C*G*A*A*U*A*A*C*C, | (SEQ ID NO: 40) |
| C*C*G*A*G*C*C*G*C*U*A*U*C*C*C, | (SEQ ID NO: 55) |
| C*C*G*A*G*C*C*G*A*A*G*G*U*A*C, | (SEQ ID NO: 82) |
| C*C*G*A*G*C*C*G*A*A*G*A*U*A*C, | (SEQ ID NO: 85) |
| C*C*G*A*G*C*C*G*A*A*U*G*U*A*C, | (SEQ ID NO: 63) |
| C*C*G*A*G*C*C*G*C*C*U*A*A*C*C, | (SEQ ID NO: 43) |
| C*C*G*A*G*C*C*G*C*A*U*A*U*C*C, | (SEQ ID NO: 36) |
| C*C*G*A*G*C*C*G*A*A*G*C*U*A*C, | (SEQ ID NO: 87) |
| C*C*G*A*G*C*C*G*C*A*U*A*C*C*C, | (SEQ ID NO: 45) |
| C*C*G*A*G*C*C*G*C*A*U*A*A*C*C, | (SEQ ID NO: 41) |
| C*C*G*A*G*C*C*G*A*A*G*G*U*G*C, | (SEQ ID NO: 83) |
| C*C*G*A*G*C*C*G*C*A*U*C*C*C*C, | (SEQ ID NO: 46) |
| C*C*G*A*G*C*C*G*A*A*G*C*U*G*C, | (SEQ ID NO: 88) |
| C*C*G*A*G*C*C*C*C*G*C*C*C*C, | (SEQ ID NO: 35) |
| C*C*G*A*G*C*C*G*A*A*G*C*U*C*C, | (SEQ ID NO: 84) | or

C*C*G*A*G*C*C*G*A*A*G*G*C*A*C. (SEQ ID NO: 56)

As mentioned above, RNA is a polymer of ribonucleotides joined through 3'-5' phosphodiester linkages. In certain embodiments the immunostimulatory ORN of the invention are RNA. However, the immunostimulatory ORN of the invention are not limited to RNA, as will be described below.

An immunostimulatory ORN of the invention can in one embodiment include one or more modified nucleobases i.e., derivatives of A, C, G, and U. Specific embodiments of these modified nucleobases include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynylcytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil), thymine derivatives (e.g. 2-thiothymine, 4-thiothymine, 6-substituted thymines), guanosine derivatives (7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 8-substituted guanine (e.g. 8-hydroxyguanine and 8-bromoguanine), and 6-thioguanine), or adenosine derivatives (5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine)). The base can also be substituted by a universal base (e.g. 4-methyl-indole, 5-nitro-indole, 3-nitropyrrole, P-base, and K-base), an aromatic ring system (e.g. benzimidazole or dichloro-benzimidazole, 1-methyl-1H-[1,2,4]triazole-3-carboxylic acid amide) an aromatic ring system (e.g. fluorobenzene or difluorobenzene) or a hydrogen atom (dSpacer). Preferred base modifications are uracil and 7-deaza-guanine. These modified U nucleobases and their corresponding ribonucleosides are available from commercial suppliers.

Specific embodiments of modified G nucleobases include $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, and 8-oxoguanine. In one embodiment the modified G nucleobase is 8-hydroxyguanine. These modified G nucleobases and their corresponding ribonucleosides are available from commercial suppliers.

In certain embodiments at least one β-ribose unit may be replaced by β-D-deoxyribose or a modified sugar unit, wherein the modified sugar unit is for example selected from β-D-ribose, α-D-ribose, β-L-ribose (as in 'Spiegelmers'), α-L-ribose, 2'-amino-2'-deoxyribose, 2'-fluoro-2'-deoxyribose, 2'-O—(C1-C6)alkyl-ribose, preferably 2'-O—(C1-C6) alkyl-ribose is 2'-O-methylribose, 2'-O—(C2-C6)alkenyl-ribose, 2'-[O—(C1-C6)alkyl-O—(C1-C6)alkyl]-ribose, LNA and α-LNA (Nielsen P et al. (2002) *Chemistry-A European Journal* 8:712-22), β-D-xylo-furanose, α-arabinofuranose, 2'-fluoro arabinofuranose, and carbocyclic and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481).

Individual ribonucleotides and ribonucleosides of the immunostimulatory ORN of the invention may alternatively be linked by non-nucleotidic linkers, in particular abasic linkers (dSpacers), triethylene glycol units, or hexaethylene glycol units. Additional linkers are alkylamino linkers, such as C3, C6, and C12 aminolinkers, and also alkylthiol linkers, such as C3 or C6 thiol linkers. Individual nucleotides and ribonucleosides of the immunostimulatory ORN of the invention may alternatively be linked by aromatic residues which may be further substituted by alkyl or substituted alkyl groups.

RNA is a polymer of ribonucleotides joined through 3'-5' phosphodiester linkages. Nucleotides of the immunostimulatory ORN of the invention can also be joined through 3'-5' phosphodiester linkages. However, the invention also encompasses immunostimulatory ORN having unusual internucleotide linkages, including specifically 5'-5', 3'-3', 2'-2', 2'-3', and 2'-5' internucleotide linkages. In one embodiment such unusual linkages are excluded from the immunostimulatory RNA motif, even though one or more of such linkages may occur elsewhere within the immunostimulatory ORN. For immunostimulatory ORN having free ends, inclusion of one 3'-3' internucleotide linkage can result in an immunostimulatory ORN having two free 5' ends. Conversely, for immunostimulatory ORN having free ends, inclusion of one 5'-5' internucleotide linkage can result in an immunostimulatory ORN having two free 3' ends.

An immunostimulatory composition of this invention can contain two or more immunostimulatory RNA motifs which can be linked through a branching unit. The internucleotide linkages can be 3'-5', 5'-5', 3'-3', 2'-2', 2'-3', or 2'-5' linkages. Thereby, the nomenclature 2'-5' is chosen according to the carbon atom of ribose. The unusual internucleotide linkage can be a phosphodiester linkage, but it can alternatively be modified as phosphorothioate or any other modified linkage as described herein. The formula below shows a general structure for branched immunostimulatory ORN of the invention via a nucleotidic branching unit. Thereby $Nu_1$, $Nu_2$, and $Nu_3$ can be linked through 3'-5', 5'-5', 3'-3', 2'-2', 2'-3', or 2'-5'-linkages. Branching of immunostimulatory ORN can also involve the use of non-nucleotidic linkers and abasic spacers. In one embodiment, $Nu_1$, $Nu_2$, and $Nu_3$ represent identical or different immunostimulatory RNA motifs. In another embodiment, $Nu_1$, $Nu_2$, and $Nu_3$ comprises at least one immunostimulatory RNA motif and at least one immunostimulatory CpG DNA motif.

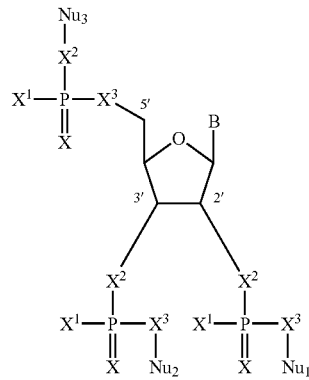

The immunostimulatory ORN may contain a doubler or trebler unit (Glen Research, Sterling, Va.), in particular those immunostimulatory ORN with a 3'-3' linkage. A doubler unit in one embodiment can be based on 1,3-bis-[5-(4,4'-dimethoxytrityloxy)pentylamido]propyl-2-[(2-cyanoethyl)-(N,N-diisopropyl)]-phosphoramidite. A trebler unit in one embodiment can be based on incorporation of Tris-2,2,2-[3-(4,4'-dimethoxytrityloxy)propyloxymethyl]ethyl-[(2-cyanoethyl)-(N,N-diisopropyl)]-phosphoramidite. Branching of the immunostimulatory ORN by multiple doubler, trebler, or other multiplier units leads to dendrimers which are a further embodiment of this invention. Branched immunostimulatory ORN may lead to crosslinking of receptors for immunostimulatory RNA such as TLR3, TLR7, and TLR8, with distinct immune effects compared to non-branched forms of the immunostimulatory ORN. In addition, the synthesis of branched or otherwise multimeric immunostimulatory ORN may stabilize RNA against degradation and may enable weak or partially effective RNA sequences to exert a therapeutically useful level of immune activity. The immunostimulatory ORN may also contain linker units resulting from peptide modifying reagents or oligonucleotide modifying reagents (Glen Research). Furthermore, the immunostimulatory ORN may contain one or more natural or unnatural amino acid residues which are connected to the polymer by peptide (amide) linkages.

The 3'-5', 5'-5', 3'-3', 2'-2', 2'-3', and 2'-5' internucleotide linkages can be direct or indirect. Direct linkages in this context refers to a phosphate or modified phosphate linkage as disclosed herein, without an intervening linker moiety. An intervening linker moiety is an organic moiety distinct from a phosphate or modified phosphate linkage as disclosed herein, which can include, for example, polyethylene glycol, triethylene glycol, hexaethylene glycol, dSpacer (i.e., an abasic deoxynucleotide), doubler unit, or trebler unit.

In certain embodiments the immunostimulatory ORN is conjugated to another entity to provide a conjugate. As used herein a conjugate refers to a combination of any two or more entities bound to one another by any physicochemical means, including hydrophobic interaction and covalent coupling.

In another embodiment, the immunostimulatory ORN may be conjugated to a small molecular weight ligand which is recognized by an immunomodulatory receptor. This receptor is preferably a member of the TLR family, such as TLR2, TLR3, TLR4, TLR7, TLR8, or TLR9. The small molecular weight ligands are mimics of the natural ligands for these receptors. Examples include but are not limited to R-848 (Resiquimod), R-837 (Imiquimod; ALDARA™, 3M Pharmaceuticals), 7-deaza-guanosine, 7-thia-8-oxo-guansosine, and 7-allyl-8-oxo-guanosine (Loxoribine) which stimulate either TLR7 or TLR8. D-Glucopyranose derivatives, such as 3D-MPL (TLR4 ligand), may also be conjugated to the immunostimulatory ORN. Pam3-Cys is an example of a TLR2 ligand which can be conjugated to immunostimulatory ORN. Oligodeoxynucleotides containing CpG motifs are TLR9 ligands, and these can also be conjugated to immunostimulatory ORN of the invention. In one embodiment, at least one oligodeoxynucleotide comprising a CpG motif effective for stimulating TLR9 signaling is conjugated to an immunostimulatory ORN of the invention. Conjugation of ligands for different TLRs into one molecule may lead to multimerisation of receptors which results in enhanced immune stimulation or a different immunostimulatory profile from that resulting from any single such ligand.

In one aspect the invention provides a conjugate of an immunostimulatory ORN of the invention and a lipophilic moiety. In certain embodiments the immunostimulatory ORN is covalently linked to a lipophilic moiety. The lipophilic moiety generally will occur at one or more ends of an immunostimulatory ORN having free ends, although in certain embodiments the lipophilic moiety can occur elsewhere along the immunostimulatory ORN and thus does not require the immunostimulatory ORN have a free end. In one embodiment the immunostimulatory ORN has a 3' end and the lipophilic moiety is covalently linked to the 3' end. The lipophilic group in general can be a cholesteryl, a modified cholesteryl, a cholesterol derivative, a reduced cholesterol, a substituted cholesterol, cholestan, C16 alkyl chain, a bile acid, cholic acid, taurocholic acid, deoxycholate, oleyl litocholic acid, oleoyl cholenic acid, a glycolipid, a phospholipid, a sphingolipid, an isoprenoid, such as steroids, vitamins, such as vitamin E, saturated fatty acids, unsaturated fatty acids, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. In certain embodiments the lipophilic moiety is chosen from cholesteryl, palmityl, and fatty acyl. In one embodiment the lipohilic moiety is cholesteryl. It is believed that inclusion of one or more of such lipophilic moieties in the immunostimulatory ORN of the invention confers upon them yet additional stability against degradation by nucleases. Where there are two or more lipophilic moieties in a single immunostimulatory ORN of the invention, each lipophilic moiety can be selected independently of any other.

In one embodiment the lipophilic group is attached to a 2'-position of a nucleotide of the immunostimulatory ORN. A lipophilic group can alternatively or in addition be linked to the heterocyclic nucleobase of a nucleotide of the immunostimulatory ORN. The lipophilic moiety can be covalently linked to the immunostimulatory ORN via any suitable direct or indirect linkage. In one embodiment the linkage is direct and is an ester or an amide. In one embodiment the linkage is indirect and includes a spacer moiety, for example one or more abasic nucleotide residues, oligoethyleneglycol, such as triethyleneglycol (spacer 9) or hexaethylenegylcol (spacer 18), or an alkane-diol, such as butanediol.

In one embodiment the immunostimulatory ORN of the invention is advantageously combined with a cationic lipid or a cationic peptide. Cationic lipids and cationic peptides are believed to assist in trafficking of the immunstimulatory ORN into the endosomal compartment, where TLR8 is found. In one embodiment the cationic lipid is DOTAP (N-[1-(2,3-dioleoyloxy)propy-1]-N,N,N-trimethylammonium methylsulfate). DOTAP is believed to transport RNA oligomer into cells and specifically traffic to the endosomal compartment, where it can release the RNA oligomer in a pH-dependent fashion. Once in the endosomal compartment, the RNA can interact with certain intracellular TLRs, triggering TLR-mediated signal transduction pathways involved in generating an immune response. Other agents with similar properties including trafficking to the endosomal compartment can be used in place of or in addition to DOTAP. Other lipid formulations include, for example, as EFFECTENE™ (a non-liposomal lipid with a special DNA condensing enhancer) and SUPERFEC™ (a novel acting dendrimeric technology). Liposomes are commercially available from Gibco BRL, for example, as LIPOFECTIN™ and LIPOFECTACE™, which are formed of cationic lipids such as N-[1-(2,3 dioleyloxy)-propyl]-N,N, N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) *Trends Biotechnol* 3:235-241.

In one embodiment the immunostimulatory ORN of the invention are in the form of covalently closed, dumbbell-shaped molecules with both primary and secondary structure. As described below, in one embodiment such cyclic oligoribonucleotides include two single-stranded loops connected by an intervening double-stranded segment. In one embodiment at least one single-stranded loop includes an immunostimulatory RNA motif of the invention. Other covalently closed, dumbbell-shaped molecules of the invention include chimeric DNA:RNA molecules in which, for example, the double-stranded segment is at least partially DNA (e.g., either homodimeric dsDNA or heterodimeric DNA:RNA) and at least one single-stranded loop includes an immunostimulatory RNA motif of the invention. Alternatively, the double stranded segment of the chimeric molecule is RNA.

In certain embodiments the immunostimulatory ORN is isolated. An isolated molecule is a molecule that is substantially pure and is free of other substances with which it is ordinarily found in nature or in in vivo systems to an extent practical and appropriate for its intended use. In particular, the immunostimulatory ORN are sufficiently pure and are sufficiently free from other biological constituents of cells so as to be useful in, for example, producing pharmaceutical preparations. Because an isolated immunostimulatory ORN of the invention may be admixed with a pharmaceutically acceptable carrier in a pharmaceutical preparation, the immunostimulatory ORN may comprise only a small percentage by weight of the preparation. The immunostimulatory ORN is nonetheless substantially pure in that it has been substantially separated from the substances with which it may be associated in living systems.

For use in the instant invention the immunostimulatory ORN of the invention can be synthesized de novo using or adapted from any of a number of procedures well known in the art. For example, the β-cyanoethyl phosphoramidite method (Beaucage S L et al. (1981) Tetrahedron Lett 22:1859); nucleoside H-phosphonate method (Garegg P et al. (1986) Tetrahedron Lett 27:4051-4; Froehler B C et al. (1986) Nucl Acid Res 14:5399-407; Garegg P et al. (1986) Tetrahedron Lett 27:4055-8; Gaffney B L et al. (1988) Tetrahedron Lett 29:2619-22). These chemistries can be performed by a variety of automated nucleic acid synthesizers available in the market. Additional synthesis methods useful according to the instant invention are disclosed in Uhlmann E et al. (1990) Chem Rev 90:544-84, and Goodchild J (1990) Bioconjugate Chem 1:165.

Oligoribonucleotide synthesis can be performed either in solution or on a solid-phase support. In solution, block coupling reactions (dimers, trimers, tetramers, etc.) are preferred, while solid-phase synthesis is preferably performed in a stepwise process using monomeric building blocks. Different chemistries, such as the phosphotriester method, H-phosphonate method, and phosphoramidite method, have been described (Eckstein F (1991) Oligonucleotides and Analogues, A Practical Approach, IRL Press, Oxford). While in the phosphotriester method the reactive phosphorus group is in the oxidation state +V, the more reactive Phosphor +III derivatives are used in the coupling reactions according to the phosphoramidite and H-phosphonate approaches. In the latter two approaches, phosphorus is oxidized after the coupling step to yield the stable P(V) derivatives. If the oxidizer is iodine/water/base, then phosphodiesters are obtained after deprotection. In contrast, if the oxidizer is a sulfurizing agent, such as Beaucage's Reagent, then phosphorothioates are obtained after deprotection.

An efficient method for oligoribonucleotide synthesis is the combination of solid-support synthesis using phosphoramidite chemistry as originally described for oligodeoxynucleotides by Matteucci and Caruthers. Matteucci M D et al. (1981) J Am Chem Soc 103:3185.

Synthesis of oligoribonucleotides is similar to oligodeoxynucleotides, with the difference that the 2'-hydroxy group present in oligoribonucleotides must be protected by a suitable hydroxy protecting group. The monomers can be protected e.g. by 2'-O-t-butyldimethylsilyl (TBDMS) group in the RNA monomeric building blocks. However, RNA synthesis using monomers containing the 2'-O-TriisopropylsilylOxyMethyl (TOM) group (TOM-Protecting-Group™) has been reported to yield higher coupling efficiency, because the TOM-Protecting-Group exhibits lower steric hindrance than the TBDMS group. While the TBDMS protecting group is removed using fluoride, fast deprotection is achieved for the TOM group using methylamine in ethanol/water at room temperature. In oligo(ribo)nucleotide synthesis, chain elongation from 3'- to 5'-end is preferred, which is achieved by coupling of a ribonucleotide unit having a 3'-phosphor (III) group or its activated derivative to a free 5'-hydroxy group of another nucleotide unit.

Synthesis can be conveniently performed using an automated DNA/RNA synthesizer. Thereby, synthesis cycles as recommended by the suppliers of the synthesizers can be used. For ribonucleoside phosphoramidite monomers, coupling times are longer (e.g., 400 sec) as compared to deoxynucleoside monomers. As solid support, 500 to 1000 Å controlled pore glass (CPG) support or organic polymer support, such as primer support PS200 (Amersham), can be used. The solid support usually contains the first nucleoside, such as 5'-O-Dimethoxytrityl-N-6-benzoyladenosine, attached via its 3'-end. After cleavage of the 5'-O-Dimethoxytrityl-group with trichloroacetic acid, chain elongation is achieved using e.g. 5'-O-Dimethoxytrityl-N-protected-2'-O-tert butyldimethylsilyl-nucleoside-3'-O-phosphoramidites. After successive repetitive cycles, the completed oligoribonucleotide is cleaved from the support and deprotected by treatment with concentrated ammonia/ethanol (3:1, v:v) for 24 hours at 30° C. The TBDMS blocking group is finally cleaved off using triethylamine/HF. The crude oligoribonucleotides can be purified by ion exchange high pressure liquid chromatography (HPLC), ion-pair reverse phase HPLC, or polyacrylamide gel electrophoresis (PAGE) and characterized by mass spectrometry.

Synthesis of 5'-conjugates is straightforward by coupling a phosphoramidite of the molecule to be ligated to the 5'-hydroxy group of the terminal nucleotide in solid-phase synthesis. A variety of phosphoramidite derivatives of such ligands, such as cholesterol, acridine, biotin, psoralene, ethyleneglycol, or aminoalkyl residues are commercially available. Alternatively, aminoalkyl functions can be introduced during solid-phase synthesis which allow post-synthesis derivatization by activated conjugate molecules, such as active esters, isothiocynates, or iodo-acetamides.

Synthesis of 3'-end conjugates is usually achieved by using the correspondingly modified solid supports, such as e.g. commercially available cholesterol-derivatized solid supports. Conjugation can however also be done at internucleotide linkages, nucleobases or at the ribose residues, such as at the 2'-position of ribose.

For cyclic oligoribonucleotides, the elongation of the oligonucleotide chain can be carried out on Nucleotide PS solid support (Glen Research) using standard phosphoramidite chemistry. The cyclization reaction is then carried out on the solid support using a phosphotriester coupling procedure (Alazzouzi et al. (1997) Nucleosides Nucleotides 16:1513-14). On final deprotection with ammonium hydroxide, virtually the only product which comes into solution is the desired cyclic oligonucleotide.

Cyclic oligoribonucleotides of the invention include closed circular forms of RNA and can include single-stranded RNA with or without double-stranded RNA. For example, in one embodiment the cyclic oligoribouncleotide includes double-stranded RNA and takes on a dumbbell conformation with two single-stranded loops connected by an intervening double-stranded segment. Covalently closed, dumbbell-shaped CpG oligodeoxynucleotides have been described in U.S. Pat. No. 6,849,725. In another embodiment the cyclic oligoribonucleotide includes double-stranded RNA and takes on a conformation with three or more single-stranded loops connected by intervening double-stranded segments. In one embodiment an immunostimulatory RNA motif is located in one or more single-stranded segments.

The immunostimulatory ORN of the invention are useful, alone or in combination with other agents, as adjuvants. An adjuvant as used herein refers to a substance other than an antigen that enhances immune cell activation in response to an antigen, e.g., a humoral and/or cellular immune response. Adjuvants promote the accumulation and/or activation of accessory cells to enhance antigen-specific immune responses. Adjuvants are used to enhance the efficacy of vaccines, i.e., antigen-containing compositions used to induce protective immunity against the antigen.

Adjuvants in general include adjuvants that create a depot effect, immune-stimulating adjuvants, and adjuvants that create a depot effect and stimulate the immune system. An adjuvant that creates a depot effect as used herein is an adjuvant that causes the antigen to be slowly released in the body, thus prolonging the exposure of immune cells to the antigen. This class of adjuvants includes but is not limited to alum (e.g., aluminum hydroxide, aluminum phosphate); emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720; AirLiquide, Paris, France); MF-59 (a squalene-in-water emulsion stabilized with Span 85 and Tween 80; Chiron Corporation, Emeryville, Calif.); and PROVAX (an oil-in-water emulsion containing a stabilizing detergent and a micelle-forming agent; IDEC Pharmaceuticals Corporation, San Diego, Calif.).

An immune-stimulating adjuvant is an adjuvant that causes activation of a cell of the immune system. It may, for instance, cause an immune cell to produce and secrete cytokines. This class of adjuvants includes but is not limited to saponins purified from the bark of the *Q. saponaria* tree, such as QS21 (a glycolipid that elutes in the 21st peak with HPLC fractionation; Aquila Biopharmaceuticals, Inc., Worcester, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). This class of adjuvants also includes CpG DNA.

Adjuvants that create a depot effect and stimulate the immune system are those compounds which have both of the above-identified functions. This class of adjuvants includes but is not limited to ISCOMS (immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

The invention in one aspect provides an adjuvant that includes an immunostimulatory ORN of the invention, by itself. In another embodiment the invention provides an adjuvant that includes an immunostimulatory ORN of the invention and at least one other adjuvant (a combination adjuvant). The other adjuvant can include an adjuvant that creates a depot effect, an immune-stimulating adjuvant, an adjuvant that creates a depot effect and stimulates the immune system, and any combination thereof. In one embodiment the immunostimulatory ORN of the invention and at least one other adjuvant are covalently linked to one another. A combination adjuvant according to the invention may exhibit a synergistic immunostimulatory effect compared to the sum of effects of the immunostimulatory ORN alone and the at least one other adjuvant alone. Additionally or alternatively, a combination adjuvant according to the invention may exhibit an altered immunostimulatory profile compared to that of either the immunostimulatory ORN alone or the at least one other adjuvant alone. For example, the combination adjuvant may provide a more balanced form of Th1/Th2 immunostimulation in one embodiment, or it may provide a more skewed form of Th1/Th2 immunostimulation in another embodiment. Those skilled in the art will recognize how to select individual components to promote a desired type of immunostimulation, e.g., more balanced or more skewed with respect to Th1 and Th2 character. Th1 and Th2 are described further below.

Also provided is a composition that includes an immunostimulatory ORN of the invention plus another adjuvant, wherein the other adjuvant is a cytokine. In one embodiment the composition is a conjugate of the immunostimulatory ORN of the invention and the cytokine.

Cytokines are soluble proteins and glycoproteins produced by many types of cells that mediate inflammatory and immune reactions. Cytokines mediate communication between cells of the immune system, acting locally as well as systemically to recruit cells and to regulate their function and proliferation. Categories of cytokines include mediators and regulators of innate immunity, mediators and regulators of adaptive immunity, and stimulators of hematopoiesis. Included among cytokines are interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, and interleukins 19-32 (IL-19-IL-32), among others), chemokines (e.g., IP-10, RANTES, MIP-1α, MIP-1β, MIP-3α, MCP-1, MCP-2, MCP-3, MCP-4, eotaxin, I-TAC, and BCA-1, among others), as well as other cytokines including type 1 interferons (e.g., IFN-α and IFN-β), type 2 interferon (e.g., IFN-γ), tumor necrosis factor-alpha (TNF-α), transforming growth factor-beta (TGF-β), and various colony stimulating factors (CSFs), including GM-CSF, G-CSF, and M-CSF.

Also provided is a composition that includes an immunostimulatory ORN of the invention plus an immunostimulatory CpG nucleic acid. In one embodiment the composition is a conjugate of the immunostimulatory ORN of the invention and the CpG nucleic acid, e.g. a RNA:DNA conjugate. In one embodiment the composition is a mixture of the immunostimulatory ORN of the invention and the CpG nucleic acid, i.e., not a RNA:DNA conjugate.

An immunostimulatory CpG nucleic acid as used herein refers to a natural or synthetic DNA sequence that includes a CpG motif and that stimulates activation or proliferation of cells of the immune system. Immunostimulatory CpG nucleic acids have been described in a number of issued patents, published patent applications, and other publications, including U.S. Pat. Nos. 6,194,388; 6,207,646; 6,214,806; 6,218,371; 6,239,116; and 6,339,068. In one embodiment the immunostimulatory CpG nucleic acid is a CpG oligodeoxynucleotide (CpG ODN) 6-100 nucleotides long. In one embodiment the immunostimulatory CpG nucleic acid is a CpG oligodeoxynucleotide (CpG ODN) 8-40 nucleotides long.

Immunostimulatory CpG nucleic acids include different classes of CpG nucleic acids. One class is potent for activating B cells but is relatively weak in inducing IFN-α and NK cell activation; this class has been termed the B class. The B class CpG nucleic acids typically are fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class is potent for inducing IFN-α and NK cell activation but is relatively weak at stimulating B cells; this class has been termed the A class. The A class CpG nucleic acids typically have a palindromic phosphodiester CpG dinucleotide-containing sequence of at least 6 nucleotides and a stabilized poly-G sequences at either or both the 5' and 3' ends. See, for example, published international patent application WO 01/22990. Yet another class of CpG nucleic acids activates B cells and NK cells and induces IFN-α; this class has been termed the C class. The C class CpG nucleic acids, as first characterized, typically are fully stabilized, include a B class-type sequence and a GC-rich palindrome or near-palindrome. This class has been described in published U.S. patent application 2003/0148976, the entire contents of which are incorporated herein by reference.

Immunostimulatory CpG nucleic acids also include so-called soft and semi-soft CpG nucleic acids, as disclosed in published U.S. patent application 2003/0148976, the entire contents of which is incorporated herein by reference. Such soft and semi-soft immunostimulatory CpG nucleic acids incorporate a combination of nuclease-resistant and nuclease-sensitive internucleotide linkages, wherein the different types of linkages are positioned according to certain rules.

Also provided is a composition that includes an immunostimulatory ORN of the invention plus another adjuvant, wherein the other adjuvant is a lipopeptide such as Pam3Cys, a cationic polysaccharide such as chitosan, or a cationic peptide such as protamine. In one embodiment the composition is a conjugate of the immunostimulatory ORN of the invention and the other adjuvant.

The invention in one aspect provides a vaccine that includes an immunostimulatory ORN of the invention and an antigen. An "antigen" as used herein refers to any molecule capable of being recognized by a T-cell antigen receptor or B-cell antigen receptor. The term broadly includes any type of molecule which is recognized by a host immune system as being foreign. Antigens generally include but are not limited to cells, cell extracts, proteins, polypeptides, peptides, polysaccharides, polysaccharide conjugates, peptide and non-peptide mimics of polysaccharides and other molecules, small molecules, lipids, glycolipids, polysaccharides, carbohydrates, viruses and viral extracts, and multicellular organisms such as parasites, and allergens. With respect to antigens that are proteins, polypeptides, or peptides, such antigens can include nucleic acid molecules encoding such antigens. Antigens more specifically include, but are not limited to, cancer antigens, which include cancer cells and molecules expressed in or on cancer cells; microbial antigens, which include microbes and molecules expressed in or on microbes; and allergens. Accordingly, the invention in certain embodiments provides vaccines for cancers, infectious agents, and allergens.

The invention in one aspect provides a use of an immunostimulatory ORN of the invention for the preparation of a medicament for vaccinating a subject.

The invention in one aspect provides a method for preparing a vaccine. The method includes the step of placing an immunostimulatory ORN of the invention in intimate association with an antigen and, optionally, a pharmaceutically acceptable carrier.

In various embodiments the antigen is a microbial antigen, a cancer antigen, or an allergen. A "microbial antigen" as used herein is an antigen of a microorganism and includes but is not limited to viruses, bacteria, parasites, and fungi. Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

Viruses are small infectious agents which generally contain a nucleic acid core and a protein coat, but are not independently living organisms. Viruses can also take the form of infectious nucleic acids lacking a protein. A virus cannot survive in the absence of a living cell within which it can replicate. Viruses enter specific living cells either by endocytosis or direct injection of DNA (phage) and multiply, causing disease. The multiplied virus can then be released and infect additional cells. Some viruses are DNA-containing viruses and others are RNA-containing viruses. In some aspects, the invention also intends to treat diseases in which prions are implicated in disease progression such as for example bovine spongiform encephalopathy (i.e., mad cow disease, BSE) or scrapie infection in animals, or Creutzfeldt-Jakob disease in humans.

Viruses include, but are not limited to, enteroviruses (including, but not limited to, viruses that the family picornaviridae, such as polio virus, coxsackie virus, echo virus), rotaviruses, adenovirus, hepatitis virus. Specific examples of viruses that have been found in humans include but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arenaviridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papillomaviruses, polyoma viruses); Adenoviridae (most adenoviruses); Herpesviridae (herpes simplex virus (HSV) 1 and 2, varicella zoster virus, cytomegalovirus (CMV)); Poxyiridae (variola viruses, vaccinia viruses, pox viruses); Iridoviridae (e.g., African swine fever virus); and unclassified viruses (e.g., the etiological agents of spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Bacteria are unicellular organisms which multiply asexually by binary fission. They are classified and named based on their morphology, staining reactions, nutrition and metabolic requirements, antigenic structure, chemical composition, and genetic homology. Bacteria can be classified into three groups based on their morphological forms, spherical (coccus), straight-rod (*bacillus*) and curved or spiral rod (*vibrio*, campylobacter, spirillum, and spirochaete). Bacteria are also more commonly characterized based on their staining reactions into two classes of organisms, gram-positive and gram-negative. Gram refers to the method of staining which is commonly performed in microbiology labs. Gram-positive organisms retain the stain following the staining procedure and appear a deep violet color. Gram-negative organisms do not retain the stain but take up the counter-stain and thus appear pink.

Infectious bacteria include, but are not limited to, gram negative and gram positive bacteria. Gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris, Borrelia burgdorferi, Legionella pneumophilia, Mycobacteria* sps (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic species), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira, Rickettsia*, and *Actinomyces israelii*.

Parasites are organisms which depend upon other organisms in order to survive and thus must enter, or infect, another organism to continue their life cycle. The infected organism, i.e., the host, provides both nutrition and habitat to the parasite. Although in its broadest sense the term parasite can include all infectious agents (i.e., bacteria, viruses, fungi, protozoa and helminths), generally speaking, the term is used to refer solely to protozoa, helminths, and ectoparasitic arthropods (e.g., ticks, mites, etc.). Protozoa are single-celled organisms which can replicate both intracellularly and extracellularly, particularly in the blood, intestinal tract or the extracellular matrix of tissues. Helminths are multicellular organisms which almost always are extracellular (an exception being *Trichinella* spp.). Helminths normally require exit from a primary host and transmission into a secondary host in order to replicate. In contrast to these aforementioned classes, ectoparasitic arthropods form a parasitic relationship with the external surface of the host body.

Parasites include intracellular parasites and obligate intracellular parasites. Examples of parasites include but are not limited to *Plasmodium falciparum, Plasmodium ovale, Plasmodium malariae, Plasmdodium vivax, Plasmodium knowlesi, Babesia microti, Babesia divergens, Trypanosoma cruzi, Toxoplasma gondii, Trichinella spiralis, Leishmania major, Leishmania donovani, Leishmania braziliensis, Leishmania tropica, Trypanosoma gambiense, Trypanosoma rhodesiense* and *Schistosoma mansoni*.

Fungi are eukaryotic organisms, only a few of which cause infection in vertebrate mammals. Because fungi are eukaryotic organisms, they differ significantly from prokaryotic bacteria in size, structural organization, life cycle and mechanism of multiplication. Fungi are classified generally based on morphological features, modes of reproduction and culture characteristics. Although fungi can cause different types of disease in subjects, such as respiratory allergies following inhalation of fungal antigens, fungal intoxication due to ingestion of toxic substances, such as *Amanita phalloides* toxin and phallotoxin produced by poisonous mushrooms and aflatoxins, produced by *aspergillus* species, not all fungi cause infectious disease.

Infectious fungi can cause systemic or superficial infections. Primary systemic infection can occur in normal healthy subjects, and opportunistic infections are most frequently found in immunocompromised subjects. The most common fungal agents causing primary systemic infection include *Blastomyces, Coccidioides*, and *Histoplasma*. Common fungi causing opportunistic infection in immunocompromised or immunosuppressed subjects include, but are not limited to, *Candida albicans, Cryptococcus neoformans*, and various *Aspergillus* species. Systemic fungal infections are invasive infections of the internal organs. The organism usually enters the body through the lungs, gastrointestinal tract, or intravenous catheters. These types of infections can be caused by primary pathogenic fungi or opportunistic fungi.

Superficial fungal infections involve growth of fungi on an external surface without invasion of internal tissues. Typical superficial fungal infections include cutaneous fungal infections involving skin, hair, or nails.

Diseases associated with fungal infection include aspergillosis, blastomycosis, candidiasis, chromoblastomycosis, coccidioidomycosis, cryptococcosis, fungal eye infections, fungal hair, nail, and skin infections, histoplasmosis, lobomycosis, mycetoma, otomycosis, paracoccidioidomycosis, disseminated *Penicillium marneffei*, phaeohyphomycosis, rhinosporidioisis, sporotrichosis, and zygomycosis.

Other medically relevant microorganisms have been described extensively in the literature, e.g., see C. G. A Thomas, *Medical Microbiology*, Bailliere Tindall, Great Britain 1983, the entire contents of which is hereby incorporated by reference. Each of the foregoing lists is illustrative and is not intended to be limiting.

As used herein, the terms "cancer antigen" and "tumor antigen" are used interchangeably to refer to a compound, such as a peptide, protein, or glycoprotein, which is associated with a tumor or cancer cell and which is capable of provoking an immune response when expressed on the surface of an antigen-presenting cell in the context of a major histocompatibility complex (MHC) molecule. Cancer antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation, and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses.

Cancer antigens can be prepared from cancer cells either by preparing crude extracts of cancer cells, for example, as described in Cohen P A et al. (1994) *Cancer Res* 54:1055-8, by partially purifying the antigens, by recombinant technology, or by de novo synthesis of known antigens. Cancer antigens include but are not limited to antigens that are recombinantly expressed, an immunogenic portion of, or a whole tumor or cancer or cell thereof. Such antigens can be isolated or prepared recombinantly or by any other means known in the art.

Examples of tumor antigens include MAGE, MART-1/Melan-A, gp100, dipeptidyl peptidase IV (DPPIV), adenosine deaminase-binding protein (ADAbp), cyclophilin b, colorectal associated antigen (CRC)-C017-1A/GA733, carcinoembryonic antigen (CEA) and its immunogenic epitopes CAP-1 and CAP-2, etv6, aml1, prostate specific antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, cdc27, adenomatous polyposis coli protein (APC), fodrin, Connexin 37, Ig-idiotype, p15, gp75, GM2 and GD2 gangliosides, viral products such as human papillomavirus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2. This list is not meant to be limiting.

An "allergen" as used herein is a molecule capable of provoking an immune response characterized by production of IgE. An allergen is also a substance that can induce an allergic or asthmatic response in a susceptible subject. Thus, in the context of this invention, the term allergen means a specific type of antigen which can trigger an allergic response which is mediated by IgE antibody.

The list of allergens is enormous and can include pollens, insect venoms, animal dander dust, fungal spores and drugs (e.g., penicillin). Examples of natural animal and plant allergens include proteins specific to the following genuses: *Canis* (*Canis familiaris*); *Dermatophagoides* (e.g., *Dermatophagoides farinae*); *Felis* (*Felis domesticus*); *Ambrosia* (*Ambrosia artemisiifolia*); *Lolium* (e.g., *Lolium perenne* and *Lolium multiflorum*); *Cryptomeria* (*Cryptomeria japonica*); *Alternaria* (*Alternaria alternata*); Alder; *Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g., *Plantago lanceolata*); *Parietaria* (e.g., *Parietaria officinalis* and *Parietaria judaica*); *Blattella* (e.g., *Blattella germanica*); *Apis* (e.g., *Apis multiflorum*); *Cupressus* (e.g., *Cupressus sempervirens, Cupressus arizonica* and *Cupressus macrocarpa*); *Juniperus* (e.g., *Juniperus sabinoides, Juniperus virginiana, Juniperus communis,* and *Juniperus ashei*); *Thuya* (e.g., *Thuya orientalis*); *Chamaecyparis* (e.g., *Chamaecyparis obtusa*); *Periplaneta* (e.g., *Periplaneta americana*); *Agropyron* (e.g., *Agropyron repens*); *Secale* (e.g., *Secale cereale*); *Triticum* (e.g., *Triticum aestivum*); *Dactylis* (e.g., *Dactylis glomerata*); *Festuca* (e.g., *Festuca elatior*); *Poa* (e.g., *Poa pratensis* and *Poa compressa*); *Avena* (e.g., *Avena sativa*); *Holcus* (e.g., *Holcus lanatus*); *Anthoxanthum* (e.g., *Anthoxanthum odoratum*); *Arrhenatherum* (e.g., *Arrhenatherum elatius*); *Agrostis* (e.g., *Agrostis alba*); *Phleum* (e.g., *Phleum pratense*); *Phalaris* (e.g., *Phalaris arundinacea*); *Paspalum* (e.g., *Paspalum notatum*); *Sorghum* (e.g., *Sorghum halepensis*); and *Bromus* (e.g., *Bromus inermis*).

The invention in one aspect provides a conjugate of an immunostimulatory ORN of the invention and an antigen. In one embodiment the immunostimulatory ORN of the invention is covalently linked to the antigen. The covalent linkage between the immunostimulatory ORN and the antigen can be any suitable type of covalent linkage, provided the immunostimulatory ORN and the antigen when so joined retain measurable functional activity of each individual component. In one embodiment the covalent linkage is direct. In another embodiment the covalent linkage is indirect, e.g., through a linker moiety. The covalently linked immunostimulatory ORN and antigen may be processed within a cell to release one from the other. In this way delivery to a cell of either component may be enhanced compared to its delivery if administered as a separate preparation or separate component. In one embodiment the antigen is an antigen per se, i.e., it is a preformed antigen.

In one aspect the invention provides a pharmaceutical composition which includes a composition of the invention, in association with a delivery vehicle. In various embodiments the delivery vehicle can be chosen from a cationic lipid, a liposome, a cochleate, a virosome, an immune-stimulating complex (ISCOM), a microparticle, a microsphere, a nanosphere, a unilamellar vesicle (LUV), a multilamellar vesicle, an oil-in-water emulsion, a water-in-oil emulsion, an emulsome, and a polycationic peptide, and, optionally, a pharmaceutically acceptable carrier. Pharmaceutically acceptable carriers are discussed below. The pharmaceutical composition of the invention optionally can further include an antigen. The composition of the invention, along with the antigen when present, is brought into physical association with the delivery vehicle using any suitable method. The immunostimulatory composition can be contained within the delivery vehicle, or it can be present on or in association with a solvent-exposed surface of the delivery vehicle. In one embodiment the immunostimulatory ORN is present on or in association with a solvent-exposed surface of the delivery vehicle, and the antigen, if present, is contained within the delivery vehicle. In another embodiment both the immunostimulatory ORN and the antigen are present on or in association with a solvent-exposed surface of the delivery vehicle. In yet another embodiment the antigen is present on or in association with a solvent-exposed surface of the delivery vehicle, and the immunostimulatory ORN is contained within the delivery vehicle. In yet another embodiment both the immunostimulatory ORN and the antigen, if antigen is included, are contained within the delivery vehicle.

The invention also provides methods for use of the immunostimulatory compositions of the invention. In one aspect the invention provides a method of activating an immune cell. The method according to this aspect of the invention includes the step of contacting an immune cell, in vitro or in vivo, with an effective amount of a composition of the invention, to activate the immune cell. The composition of the invention can optionally include an antigen. An "immune cell" as used herein refers to any bone marrow-derived cell that can participate in an innate or adaptive immune response. Cells of the immune system include, without limitation, dendritic cells (DC), natural killer (NK) cells, monocytes, macrophages, granulocytes, B lymphocytes, plasma cells, T lymphocytes, and precursor cells thereof.

As used herein, the term "effective amount" refers to that amount of a substance that is necessary or sufficient to bring about a desired biological effect. An effective amount can but need not be limited to an amount administered in a single administration.

As used herein, the term "activate an immune cell" refers to inducing an immune cell to enter an activated state that is associated with an immune response. The term "activate an immune cell" refers both to inducing and augmenting an immune response. As used herein, the term "immune response" refers to any aspect of an innate or adaptive immune response that reflects activation of an immune cell to proliferate, to perform an effector immune function, or to produce a gene product involved in an immune response. Gene products involved in an immune response can include secreted products (e.g., antibodies, cytokines, and chemokines) as well as intracellular and cell surface molecules characteristic of immune function (e.g., certain cluster of differentiation (CD) antigens, transcription factors, and gene transcripts). The term "immune response" can be applied to a single cell or to a population of cells.

Production of cytokines can be assessed by any of several methods well known in the art, including biological response assays, enzyme-linked immunosorbent assay (ELISA), intracellular fluorescence-activated cell sorting (FACS) analysis, and reverse transcriptase/polymerase chain reaction (RT-PCR).

In one embodiment the immune response involves production of a pro-inflammatory cytokine immune response. A pro-inflammatory cytokine immune response can include expression of any of certain cytokines and chemokines, including IFN-γ, TNF-α, IL-12, IL-10, IL-6, and any combination thereof. It specifically excludes IFN-α for purposes of the invention.

In one embodiment the immune response involves upregulation of cell surface markers of immune cell activation, such as CD25, CD80, CD86, and CD154. Methods for measuring cell surface expression of such markers are well known in the art and include FACS analysis.

For measurement of immune response in a cell or population of cells, in one embodiment the cell or population of cells expresses TLR8. The cell can express the TLR naturally, or it can be manipulated to express the TLR though introduction into the cell of a suitable expression vector for the TLR. In one embodiment the cell or population of cells is obtained as peripheral blood mononuclear cells (PBMC). In one embodiment the cell or population of cells is obtained as a cell line expressing the TLR. In one embodiment the cell or population of cells is obtained as a transient transfectant expressing the TLR. In one embodiment the cell or population of cells is obtained as a stable transfectant expressing the TLR.

Also for use in measuring an immune response in a cell or population of cells, it may be convenient to introduce into the cell or population of cells a reporter construct that is responsive to intracellular signaling by a TLR. In one embodiment such a reporter is a gene placed under the control of an NF-κB promoter. In one embodiment the gene placed under control of the promoter is luciferase. Under suitable conditions of activation, the luciferase reporter construct is expressed and emits a detectable light signal that may be measured quantitatively using a luminometer. Such reporter constructs and other suitable reporter constructs are commercially available.

The invention also contemplates the use of cell-free methods of detecting TLR activation.

The invention in certain aspects relates to compositions and methods for use in therapy. The immunostimulatory compositions of the invention can be used alone or combined with other therapeutic agents. The immunostimulatory composition and other therapeutic agent may be administered simultaneously or sequentially. When the immunostimulatory composition of the invention and the other therapeutic agent are administered simultaneously, they can be administered in the same or separate formulations, but they are administered at the same time. In addition, when the immunostimulatory composition of the invention and the other therapeutic agent are administered simultaneously, they can be administered via the same or separate routes of administration, but they are administered at the same time. The immunostimulatory composition of the invention and another therapeutic agent are administered sequentially when administration of the immunostimulatory composition of the invention is temporally separated from administration of the other therapeutic agent. The separation in time between the administration of these compounds may be a matter of minutes or it may be longer. In one embodiment the immunostimulatory composition of the invention is administered before administration of the other therapeutic agent. In one embodiment the immunostimulatory composition of the invention is administered after administration of the other therapeutic agent. In addition, when the immunostimulatory composition of the invention and the other therapeutic agent are administered sequentially, they can be administered via the same or separate routes of administration. Other therapeutic agents include but are not limited to adjuvants, antigens, vaccines, and medicaments useful for the treatment of infection, cancer, allergy, and asthma.

In one aspect the invention provides a method of vaccinating a subject. The method according to this aspect of the invention includes the step of administering to the subject an antigen and a composition of the invention. In one embodiment the administering the antigen includes administering a nucleic acid encoding the antigen.

A "subject" as used herein refers to a vertebrate animal. In various embodiments the subject is a human, a non-human primate, or other mammal. In certain embodiments the subject is a mouse, rat, guinea pig, rabbit, cat, dog, pig, sheep, goat, cow, or horse.

For use in the method of vaccinating a subject, the composition of the invention in one embodiment includes an antigen. The antigen can be separate from or covalently linked to a ORN of the invention. In one embodiment the composition of the invention does not itself include the antigen. In this embodiment the antigen can be administered to the subject either separately from the composition of the invention, or together with the composition of the invention. Administration that is separate includes separate in time, separate in location or route of administration, or separate both in time and in location or route of administration. When the composition of the invention and the antigen are administered separate in time, the antigen can be administered before or after the composition of the invention. In one embodiment the antigen is administered 48 hours to 4 weeks after administration of the composition of the invention. The method also contemplates the administration of one or more booster doses of antigen alone, composition alone, or antigen and composition, following an initial administration of antigen and composition.

It is also contemplated by the invention that a subject can be prepared for a future encounter with an unknown antigen by administering to the subject a composition of the invention, wherein the composition does not include an antigen. According to this embodiment the immune system of the subject is prepared to mount a more vigorous response to an antigen that is later encountered by the subject, for example through environmental or occupational exposure. Such method can be used, for example, for travelers, medical workers, and soldiers likely to be exposed to microbial agents.

In one aspect the invention provides a method of treating a subject having an immune system deficiency. The method according to this aspect of the invention includes the step of administering to the subject an effective amount of a composition of the invention to treat the subject. An "immune system deficiency" as used herein refers to an abnormally depressed ability of an immune system to mount an immune response to an antigen. In one embodiment an immune system deficiency is a disease or disorder in which the subject's immune system is not functioning in normal capacity or in which it would be useful to boost the subject's immune response, for example to eliminate a tumor or cancer or an infection in the subject. A "subject having an immune deficiency" as used herein refers to a subject in which there is a depressed ability of the subject's immune system to mount an immune response to an antigen. Subjects having an immune deficiency include subjects having an acquired immune deficiency as well as subjects having a congenital immune system deficiency. Subjects having acquired immune deficiency include, without limitation, subjects having a chronic inflammatory condition, subjects having chronic renal insufficiency or renal failure, subjects having infection, subjects having cancer, subjects receiving immunosuppressive drugs, subjects receiving other immunosuppressive treatment, and subjects with malnutrition. In one embodiment the subject has a suppressed CD4+ T-cell population. In one embodiment the subject has an infection with human immunodeficiency virus (HIV) or has acquired immunodeficiency syndrome (AIDS). The method according to this aspect of the invention thus provides a method for boosting an immune response or boosting the ability to mount an immune response in a subject in need of a more vigorous immune response.

The compositions and methods of the invention can be used alone or in conjunction with other agents and methods useful for the treatment of infection. In one aspect the invention provides a method of treating a subject having an infection. The method according to this aspect of the invention includes the step of administering to a subject having an infection an effective amount of the composition of the invention to treat the subject.

In one aspect the invention provides a method of treating a subject having an infection. The method according to this aspect of the invention includes the step of administering to a subject having an infection an effective amount of the composition of the invention and an infection medicament to treat the subject.

In one aspect the invention provides a use of an immunostimulatory ORN of the invention for the preparation of a medicament for treating an infection in a subject.

In one aspect the invention provides a composition useful for the treatment of infection. The composition according to this aspect includes an immunostimulatory ORN of the invention and an infection medicament.

As used herein, the term "treat" as used in reference to a subject having a disease or condition shall mean to prevent, ameliorate, or eliminate at least one sign or symptom of the disease or condition in the subject.

A "subject having an infection" is a subject that has a disorder arising from the invasion of the subject, superficially, locally, or systemically, by an infectious microorganism. The infectious microorganism can be a virus, bacterium, fungus, or parasite, as described above.

Infection medicaments include but are not limited to anti-bacterial agents, anti-viral agents, anti-fungal agents and anti-parasitic agents. Phrases such as "anti-infective agent", "anti-biotic", "anti-bacterial agent", "anti-viral agent", "anti-fungal agent", "anti-parasitic agent" and "parasiticide" have well-established meanings to those of ordinary skill in the art and are defined in standard medical texts. Briefly, anti-bacterial agents kill or inhibit bacteria, and include antibiotics as well as other synthetic or natural compounds having similar functions. Anti-viral agents can be isolated from natural sources or synthesized and are useful for killing or inhibiting viruses. Anti-fungal agents are used to treat superficial fungal infections as well as opportunistic and primary systemic fungal infections. Anti-parasite agents kill or inhibit parasites. Many antibiotics are low molecular weight molecules which are produced as secondary metabolites by cells, such as microorganisms. In general, antibiotics interfere with one or more functions or structures which are specific for the microorganism and which are not present in host cells.

One of the problems with anti-infective therapies is the side effects occurring in the host that is treated with the anti-infective agent. For instance, many anti-infectious agents can kill or inhibit a broad spectrum of microorganisms and are not specific for a particular type of species. Treatment with these types of anti-infectious agents results in the killing of the normal microbial flora living in the host, as well as the infectious microorganism. The loss of the microbial flora can lead to disease complications and predispose the host to infection by other pathogens, since the microbial flora compete with and function as barriers to infectious pathogens. Other side effects may arise as a result of specific or non-specific effects of these chemical entities on non-microbial cells or tissues of the host.

Another problem with widespread use of anti-infectants is the development of antibiotic-resistant strains of microorganisms. Already, vancomycin-resistant enterococci, penicillin-resistant pneumococci, multi-resistant *S. aureus*, and multi-resistant tuberculosis strains have developed and are becoming major clinical problems. Widespread use of anti-infectants will likely produce many antibiotic-resistant strains of bacteria. As a result, new anti-infective strategies will be required to combat these microorganisms.

Antibacterial antibiotics which are effective for killing or inhibiting a wide range of bacteria are referred to as broad-spectrum antibiotics. Other types of antibacterial antibiotics are predominantly effective against the bacteria of the class gram-positive or gram-negative. These types of antibiotics are referred to as narrow-spectrum antibiotics. Other antibiotics which are effective against a single organism or disease and not against other types of bacteria, are referred to as limited-spectrum antibiotics.

Anti-bacterial agents are sometimes classified based on their primary mode of action. In general, anti-bacterial agents are cell wall synthesis inhibitors, cell membrane inhibitors, protein synthesis inhibitors, nucleic acid synthesis or functional inhibitors, and competitive inhibitors. Cell wall synthesis inhibitors inhibit a step in the process of cell wall synthesis, and in general in the synthesis of bacterial peptidoglycan. Cell wall synthesis inhibitors include β-lactam antibiotics, natural penicillins, semi-synthetic penicillins, ampicillin, clavulanic acid, cephalolsporins, and bacitracin.

The β-lactams are antibiotics containing a four-membered β-lactam ring which inhibits the last step of peptidoglycan synthesis. β-lactam antibiotics can be synthesized or natural. The β-lactam antibiotics produced by *penicillium* are the natural penicillins, such as penicillin G or penicillin V. These are produced by fermentation of *Penicillium chrysogenum*. The natural penicillins have a narrow spectrum of activity and are generally effective against *Streptococcus, Gonococcus,* and *Staphylococcus*. Other types of natural penicillins, which are also effective against gram-positive bacteria, include penicillins F, X, K, and O.

Semi-synthetic penicillins are generally modifications of the molecule 6-aminopenicillanic acid produced by a mold. The 6-aminopenicillanic acid can be modified by addition of side chains which produce penicillins having broader spectrums of activity than natural penicillins or various other advantageous properties. Some types of semi-synthetic penicillins have broad spectrums against gram-positive and gram-negative bacteria, but are inactivated by penicillinase. These semi-synthetic penicillins include ampicillin, carbenicillin, oxacillin, azlocillin, mezlocillin, and piperacillin. Other types of semi-synthetic penicillins have narrower activities against gram-positive bacteria, but have developed properties such that they are not inactivated by penicillinase. These include, for instance, methicillin, dicloxacillin, and nafcillin. Some of the broad spectrum semi-synthetic penicillins can be used in combination with β-lactamase inhibitors, such as clavulanic acids and sulbactam. The β-lactamase inhibitors do not have anti-microbial action but they function to inhibit penicillinase, thus protecting the semi-synthetic penicillin from degradation.

Another type of β-lactam antibiotic is the cephalolsporins. They are sensitive to degradation by bacterial β-lactamases, and thus, are not always effective alone. Cephalolsporins, however, are resistant to penicillinase. They are effective against a variety of gram-positive and gram-negative bacteria. Cephalolsporins include, but are not limited to, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, and moxalactam.

Bacitracin is another class of antibiotics which inhibit cell wall synthesis, by inhibiting the release of muropeptide subunits or peptidoglycan from the molecule that delivers the subunit to the outside of the membrane. Although bacitracin is effective against gram-positive bacteria, its use is limited in general to topical administration because of its high toxicity.

Carbapenems are another broad-spectrum β-lactam antibiotic, which is capable of inhibiting cell wall synthesis. Examples of carbapenems include, but are not limited to, imipenems. Monobactams are also broad-spectrum β-lactam antibiotics, and include, euztreonam. An antibiotic produced by *Streptomyces*, vancomycin, is also effective against gram-positive bacteria by inhibiting cell membrane synthesis.

Another class of anti-bacterial agents is the anti-bacterial agents that are cell membrane inhibitors. These compounds disorganize the structure or inhibit the function of bacterial membranes. One problem with anti-bacterial agents that are cell membrane inhibitors is that they can produce effects in eukaryotic cells as well as bacteria because of the similarities in phospholipids in bacterial and eukaryotic membranes. Thus these compounds are rarely specific enough to permit these compounds to be used systemically and prevent the use of high doses for local administration.

One clinically useful cell membrane inhibitor is Polymyxin. Polymyxins interfere with membrane function by binding to membrane phospholipids. Polymyxin is effective mainly against Gram-negative bacteria and is generally used in severe *Pseudomonas* infections or *Pseudomonas* infections that are resistant to less toxic antibiotics. The severe side effects associated with systemic administration of this compound include damage to the kidney and other organs.

Other cell membrane inhibitors include Amphotericin B and Nystatin which are anti-fungal agents used predominantly in the treatment of systemic fungal infections and *Candida* yeast infections. Imidazoles are another class of antibiotic that is a cell membrane inhibitor. Imidazoles are used as anti-bacterial agents as well as anti-fungal agents, e.g., used for treatment of yeast infections, dermatophytic infections, and systemic fungal infections. Imidazoles include but are not limited to clotrimazole, miconazole, ketoconazole, itraconazole, and fluconazole.

Many anti-bacterial agents are protein synthesis inhibitors. These compounds prevent bacteria from synthesizing structural proteins and enzymes and thus cause inhibition of bacterial cell growth or function or cell death. In general these compounds interfere with the processes of transcription or translation. Anti-bacterial agents that block transcription include but are not limited to Rifampins and Ethambutol. Rifampins, which inhibit the enzyme RNA polymerase, have a broad spectrum activity and are effective against gram-positive and gram-negative bacteria as well as *Mycobacterium tuberculosis*. Ethambutol is effective against *Mycobacterium tuberculosis*.

Anti-bacterial agents which block translation interfere with bacterial ribosomes to prevent mRNA from being translated into proteins. In general this class of compounds includes but is not limited to tetracyclines, chloramphenicol, the macrolides (e.g., erythromycin) and the aminoglycosides (e.g., streptomycin).

The aminoglycosides are a class of antibiotics which are produced by the bacterium *Streptomyces*, such as, for instance streptomycin, kanamycin, tobramycin, amikacin, and gentamicin. Aminoglycosides have been used against a wide variety of bacterial infections caused by Gram-positive and Gram-negative bacteria. Streptomycin has been used extensively as a primary drug in the treatment of *tuberculosis*. Gentamicin is used against many strains of Gram-positive and Gram-negative bacteria, including *Pseudomonas* infections, especially in combination with Tobramycin. Kanamycin is used against many Gram-positive bacteria, including penicillin-resistant Staphylococci. One side effect of aminoglycosides that has limited their use clinically is that at dosages which are essential for efficacy, prolonged use has been shown to impair kidney function and cause damage to the auditory nerves leading to deafness.

Another type of translation inhibitor anti-bacterial agent is the tetracyclines. The tetracyclines are a class of antibiotics that are broad-spectrum and are effective against a variety of gram-positive and gram-negative bacteria. Examples of tetracyclines include tetracycline, minocycline, doxycycline, and chlortetracycline. They are important for the treatment of many types of bacteria but are particularly important in the treatment of Lyme disease. As a result of their low toxicity and minimal direct side effects, the tetracyclines have been overused and misused by the medical community, leading to problems. For instance, their overuse has led to widespread development of resistance.

Anti-bacterial agents such as the macrolides bind reversibly to the 50 S ribosomal subunit and inhibit elongation of the protein by peptidyl transferase or prevent the release of uncharged tRNA from the bacterial ribosome or both. These compounds include erythromycin, roxithromycin, clarithromycin, oleandomycin, and azithromycin. Erythromycin is active against most Gram-positive bacteria, *Neisseria, Legionella* and *Haemophilus*, but not against the Enterobacteriaceae. Lincomycin and clindamycin, which block peptide bond formation during protein synthesis, are used against gram-positive bacteria.

Another type of translation inhibitor is chloramphenicol. Chloramphenicol binds the 70 S ribosome inhibiting the bacterial enzyme peptidyl transferase thereby preventing the growth of the polypeptide chain during protein synthesis. One serious side effect associated with chloramphenicol is aplastic anemia. Aplastic anemia develops at doses of chloramphenicol which are effective for treating bacteria in a small proportion (1/50,000) of patients. Chloramphenicol which was once a highly prescribed antibiotic is now seldom uses as a result of the deaths from anemia. Because of its effectiveness it is still used in life-threatening situations (e.g., typhoid fever).

Some anti-bacterial agents disrupt nucleic acid synthesis or function, e.g., bind to DNA or RNA so that their messages cannot be read. These include but are not limited to quinolones and co-trimoxazole, both synthetic chemicals and rifamycins, a natural or semi-synthetic chemical. The quinolones block bacterial DNA replication by inhibiting the DNA gyrase, the enzyme needed by bacteria to produce their circular DNA. They are broad spectrum and examples include norfloxacin, ciprofloxacin, enoxacin, nalidixic acid and temafloxacin. Nalidixic acid is a bactericidal agent that binds to the DNA gyrase enzyme (topoisomerase) which is essential for DNA replication and allows supercoils to be relaxed and reformed, inhibiting DNA gyrase activity. The main use of nalidixic acid is in treatment of lower urinary tract infections (UTI) because it is effective against several types of Gram-negative bacteria such as $E.$ $coli,$ $Enterobacter$ $aerogenes,$ $K.$ $pneumoniae$ and $Proteus$ species which are common causes of UTI. Co-trimoxazole is a combination of sulfamethoxazole and trimethoprim, which blocks the bacterial synthesis of folic acid needed to make DNA nucleotides. Rifampicin is a derivative of rifamycin that is active against Gram-positive bacteria (including $Mycobacterium$ $tuberculosis$ and meningitis caused by $Neisseria$ $meningitidis$) and some Gram-negative bacteria. Rifampicin binds to the beta subunit of the polymerase and blocks the addition of the first nucleotide which is necessary to activate the polymerase, thereby blocking mRNA synthesis.

Another class of anti-bacterial agents is compounds that function as competitive inhibitors of bacterial enzymes. The competitive inhibitors are mostly all structurally similar to a bacterial growth factor and compete for binding but do not perform the metabolic function in the cell. These compounds include sulfonamides and chemically modified forms of sulfanilamide which have even higher and broader antibacterial activity. The sulfonamides (e.g., gantrisin and trimethoprim) are useful for the treatment of $Streptococcus$ $pneumoniae$, beta-hemolytic streptococci and $E.$ $coli$, and have been used in the treatment of uncomplicated UTI caused by $E.$ $coli$, and in the treatment of meningococcal meningitis.

Anti-viral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleoside analogues), maturation of new virus proteins (e.g. protease inhibitors), and budding and release of the virus.

Another category of anti-viral agents are nucleoside analogues. Nucleoside analogues are synthetic compounds which are similar to nucleosides, but which have an incomplete or abnormal deoxyribose or ribose group. Once the nucleoside analogues are in the cell, they are phosphorylated, producing the triphosphate form which competes with normal nucleotides for incorporation into the viral DNA or RNA. Once the triphosphate form of the nucleoside analogue is incorporated into the growing nucleic acid chain, it causes irreversible association with the viral polymerase and thus chain termination. Nucleoside analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, and zidovudine (azidothymidine).

Another class of anti-viral agents includes cytokines such as interferons. The interferons are cytokines which are secreted by virus-infected cells as well as immune cells. The interferons function by binding to specific receptors on cells adjacent to the infected cells, causing the change in the cell which protects it from infection by the virus. α and β-interferon also induce the expression of Class I and Class II MHC molecules on the surface of infected cells, resulting in increased antigen presentation for host immune cell recognition. α and β-interferons are available as recombinant forms and have been used for the treatment of chronic hepatitis B and C infection. At the dosages which are effective for antiviral therapy, interferons have severe side effects such as fever, malaise and weight loss.

Immunoglobulin therapy is used for the prevention of viral infection. Immunoglobulin therapy for viral infections is different from bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immune globulin therapy and hyper-immune globulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Examples of hyper-immune globulins include zoster immune globulin (useful for the prevention of varicella in immuno-compromised children and neonates), human rabies immune globulin (useful in the post-exposure prophylaxis of a subject bitten by a rabid animal), hepatitis B immune globulin (useful in the prevention of hepatitis B virus, especially in a subject exposed to the virus), and RSV immune globulin (useful in the treatment of respiratory syncitial virus infections).

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, imidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g., chitinase) or immunosuppression (501 cream).

Parasiticides are agents that kill parasites directly. Such compounds are known in the art and are generally commercially available. Examples of parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide.

The ORNs are also useful for treating and preventing autoimmune disease. Autoimmune disease is a class of diseases in which an subject's own antibodies react with host tissue or in which immune effector T cells are autoreactive to endogenous self peptides and cause destruction of tissue. Thus an immune response is mounted against a subject's own antigens, referred to as self antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to the destruction of the tumor or cancer. Thus, in some aspects of the invention aimed at treating autoimmune disorders it is not recommended that the ORN be administered with self antigens, particularly those that are the targets of the autoimmune disorder.

In other instances, the ORN may be delivered with low doses of self-antigens. A number of animal studies have demonstrated that mucosal administration of low doses of antigen can result in a state of immune hyporesponsiveness or "tolerance." The active mechanism appears to be a cytokine-mediated immune deviation away from a Th1 towards a predominantly Th2 and Th3 (i.e., TGF-β dominated) response. The active suppression with low dose antigen delivery can also suppress an unrelated immune response (bystander suppression) which is of considerable interest in the therapy of autoimmune diseases, for example, rheumatoid arthritis and SLE. Bystander suppression involves the secretion of Th1-counter-regulatory, suppressor cytokines in the local environment where proinflammatory and Th1 cytokines are released in either an antigen-specific or antigen-nonspecific manner. "Tolerance" as used herein is used to refer to this phenomenon. Indeed, oral tolerance has been effective in the treatment of a number of autoimmune diseases in animals including: experimental autoimmune encephalomyelitis (EAE), experimental autoimmune myasthenia gravis, collagen-induced arthritis (CIA), and insulin-dependent diabetes mellitus. In these models, the prevention and suppression of autoimmune disease is associated with a shift in antigen-specific humoral and cellular responses from a Th1 to Th2/Th3 response.

The compositions and methods of the invention can be used alone or in conjunction with other agents and methods useful for the treatment of cancer. In one aspect the invention provides a method of treating a subject having a cancer. The method according to this aspect of the invention includes the step of administering to a subject having a cancer an effective amount of a composition of the invention to treat the subject.

In one aspect the invention provides a method of treating a subject having a cancer. The method according to this aspect of the invention includes the step of administering to a subject having a cancer an effective amount of the composition of the invention and an anti-cancer therapy to treat the subject.

In one aspect the invention provides a use of an immunostimulatory ORN of the invention for the preparation of a medicament for treating cancer in a subject.

In one aspect the invention provides a composition useful for the treatment of cancer. The composition according to this aspect includes an immunostimulatory ORN of the invention and a cancer medicament.

A subject having a cancer is a subject that has detectable cancerous cells. The cancer may be a malignant or non-malignant cancer. "Cancer" as used herein refers to an uncontrolled growth of cells which interferes with the normal functioning of the bodily organs and systems. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

A metastasis is a region of cancer cells, distinct from the primary tumor location, resulting from the dissemination of cancer cells from the primary tumor to other parts of the body. At the time of diagnosis of the primary tumor mass, the subject may be monitored for the presence of metastases. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Cancers include, but are not limited to, basal cell carcinoma, biliary tract cancer; bladder cancer; bone cancer; brain and central nervous system (CNS) cancer; breast cancer; cervical cancer; choriocarcinoma; colon and rectum cancer; connective tissue cancer; cancer of the digestive system; endometrial cancer; esophageal cancer; eye cancer; cancer of the head and neck; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas, adenocarcinomas, and sarcomas.

The immunostimulatory composition of the invention may also be administered in conjunction with an anti-cancer therapy. Anti-cancer therapies include cancer medicaments, radiation, and surgical procedures. As used herein, a "cancer medicament" refers to an agent which is administered to a subject for the purpose of treating a cancer. As used herein, "treating cancer" includes preventing the development of a cancer, reducing the symptoms of cancer, and/or inhibiting the growth of an established cancer. In other aspects, the cancer medicament is administered to a subject at risk of developing a cancer for the purpose of reducing the risk of developing the cancer. Various types of medicaments for the treatment of cancer are described herein. For the purpose of this specification, cancer medicaments are classified as chemotherapeutic agents, immunotherapeutic agents, cancer vaccines, hormone therapy, and biological response modifiers.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate, but it is not so limited.

The immunotherapeutic agent may be selected from the group consisting of 3622W94, 4B5, ANA Ab, anti-FLK-2, anti-VEGF, ATRAGEN, AVASTIN (bevacizumab; Genentech), BABS, BEC2, BEXXAR (tositumomab; GlaxoSmithKline), C225, CAMPATH (alemtuzumab; Genzyme Corp.), CEACIDE, CMA 676, EMD-72000, ERBITUX (cetuximab; ImClone Systems, Inc.), Gliomab-H, GNI-250, HERCEPTIN (trastuzumab; Genentech), IDEC-Y2B8, ImmuRAIT-CEA, ior c5, ior egf.r3, ior t6, LDP-03, LymphoCide, MDX-11, MDX-22, MDX-210, MDX-220, MDX-260, MDX-447, MELIMMUNE-1, MELIMMUNE-2, Monopharm-C, NovoMAb-G2, Oncolym, OV103, Ovarex, Panorex, Pretarget, Quadramet, Ributaxin, RITUXAN (rituximab; Genentech), SMART 1D10 Ab, SMART ABL 364 Ab, SMART M195, TNT, and ZENAPAX (daclizumab; Roche), but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vacine, TA-HPV, TA-CIN, DISC-virus and ImmuCyst/TheraCys, but it is not so limited.

The compositions and methods of the invention can be used alone or in conjunction with other agents and methods useful for the treatment of allergy. In one aspect the invention provides a method of treating a subject having an allergic condition. The method according to this aspect of the invention includes the step of administering to a subject having an allergic condition an effective amount of a composition of the invention to treat the subject.

In one aspect the invention provides a method of treating a subject having an allergic condition. The method according to this aspect of the invention includes the step of administering to a subject having an allergic condition an effective amount of the composition of the invention and an anti-allergy therapy to treat the subject.

In one aspect the invention provides a use of an immunostimulatory ORN of the invention for the preparation of a medicament for treating an allergic condition in a subject.

In one aspect the invention provides a composition useful for the treatment of an allergic condition. The composition according to this aspect includes an immunostimulatory ORN of the invention and an allergy medicament.

A "subject having an allergic condition" shall refer to a subject that is currently experiencing or has previously experienced an allergic reaction in response to an allergen.

An "allergic condition" or "allergy" refers to acquired hypersensitivity to a substance (allergen). Allergic conditions include but are not limited to eczema, allergic rhinitis or coryza, hay fever, allergic conjunctivitis, bronchial asthma, urticaria (hives) and food allergies, other atopic conditions including atopic dermatitis; anaphylaxis; drug allergy; and angioedema.

Allergy is typically an episodic condition associated with the production of antibodies from a particular class of immunoglobulin, IgE, against allergens. The development of an IgE-mediated response to common aeroallergens is also a factor which indicates predisposition towards the development of asthma. If an allergen encounters a specific IgE which is bound to an IgE Fc receptor (FcεR) on the surface of a basophil (circulating in the blood) or mast cell (dispersed throughout solid tissue), the cell becomes activated, resulting in the production and release of mediators such as histamine, serotonin, and lipid mediators.

An allergic reaction occurs when tissue-sensitizing immunoglobulin of the IgE type reacts with foreign allergen. The IgE antibody is bound to mast cells and/or basophils, and these specialized cells release chemical mediators (vasoactive amines) of the allergic reaction when stimulated to do so by allergens bridging the ends of the antibody molecule. Histamine, platelet activating factor, arachidonic acid metabolites, and serotonin are among the best known mediators of allergic reactions in man. Histamine and the other vasoactive amines are normally stored in mast cells and basophil leukocytes. The mast cells are dispersed throughout animal tissue and the basophils circulate within the vascular system. These cells manufacture and store histamine within the cell unless the specialized sequence of events involving IgE binding occurs to trigger its release.

Symptoms of an allergic reaction vary, depending on the location within the body where the IgE reacts with the antigen. If the reaction occurs along the respiratory epithelium, the symptoms generally are sneezing, coughing and asthmatic reactions. If the interaction occurs in the digestive tract, as in the case of food allergies, abdominal pain and diarrhea are common. Systemic allergic reactions, for example following a bee sting or administration of penicillin to an allergic subject, can be severe and often life-threatening.

Allergy is associated with a Th2-type of immune response, which is characterized at least in part by Th2 cytokines IL-4 and IL-5, as well as antibody isotype switching to IgE. Th1 and Th2 immune responses are mutually counter-regulatory, so that skewing of the immune response toward a Th1-type of immune response can prevent or ameliorate a Th2-type of immune response, including allergy. The immunostimulatory ORN of the invention are therefore useful by themselves to treat a subject having an allergic condition because the immunostimulatory ORN can skew the immune response toward a Th1-type of immune response. Alternatively or in addition, the immunostimulatory ORN of the invention can be used in combination with an allergen to treat a subject having an allergic condition.

The immunostimulatory composition of the invention may also be administered in conjunction with an anti-allergy therapy. Conventional methods for treating or preventing allergy have involved the use of allergy medicaments or desensitization therapies. Some evolving therapies for treating or preventing allergy include the use of neutralizing anti-IgE antibodies. Anti-histamines and other drugs which block the effects of chemical mediators of the allergic reaction help to regulate the severity of the allergic symptoms but do not prevent the allergic reaction and have no effect on subsequent allergic responses. Desensitization therapies are performed by giving small doses of an allergen, usually by injection under the skin, in order to induce an IgG-type response against the allergen. The presence of IgG antibody helps to neutralize the production of mediators resulting from the induction of IgE antibodies, it is believed. Initially, the subject is treated with a very low dose of the allergen to avoid inducing a severe reaction and the dose is slowly increased. This type of therapy is dangerous because the subject is actually administered the compounds which cause the allergic response and severe allergic reactions can result.

Allergy medicaments include, but are not limited to, anti-histamines, corticosteroids, and prostaglandin inducers. Anti-histamines are compounds which counteract histamine released by mast cells or basophils. These compounds are well known in the art and commonly used for the treatment of allergy. Anti-histamines include, but are not limited to, acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast.

Corticosteroids include, but are not limited to, methylprednisolone, prednisolone, prednisone, beclomethasone, budesonide, dexamethasone, flunisolide, fluticasone propionate, and triamcinolone. Although dexamethasone is a corticosteroid having anti-inflammatory action, it is not regularly used for the treatment of allergy or asthma in an inhaled form because it is highly absorbed and it has long-term suppressive side effects at an effective dose. Dexamethasone, however, can be used according to the invention for treating allergy or asthma because when administered in combination with a composition of the invention it can be administered at a low dose to reduce the side effects. Some of the side effects associated with corticosteroid use include cough, dysphonia, oral thrush (candidiasis), and in higher doses, systemic effects, such as adrenal suppression, glucose intolerance, osteoporosis, aseptic necrosis of bone, cataract formation, growth suppression, hypertension, muscle weakness, skin thinning, and easy bruising. Barnes & Peterson (1993) *Am Rev Respir Dis* 148:S1-S26; and Kamada A K et al. (1996) *Am J Respir Crit Care Med* 153:1739-48.

The compositions and methods of the invention can be used alone or in conjunction with other agents and methods useful for the treatment of asthma. In one aspect the invention provides a method of treating a subject having asthma. The method according to this aspect of the invention includes the step of administering to a subject having asthma an effective amount of a composition of the invention to treat the subject.

In one aspect the invention provides a method of treating a subject having asthma. The method according to this aspect of the invention includes the step of administering to a subject having asthma an effective amount of the composition of the invention and an anti-asthma therapy to treat the subject.

In one aspect the invention provides a use of an immunostimulatory ORN of the invention for the preparation of a medicament for treating asthma in a subject.

In one aspect the invention provides a composition useful for the treatment of asthma. The composition according to this aspect includes an immunostimulatory ORN of the invention and an asthma medicament.

"Asthma" as used herein refers to a disorder of the respiratory system characterized by inflammation and narrowing of the airways, and increased reactivity of the airways to inhaled agents. Asthma is frequently, although not exclusively, associated with an atopic or allergic condition. Symptoms of asthma include recurrent episodes of wheezing, breathlessness, chest tightness, and coughing, resulting from airflow obstruction. Airway inflammation associated with asthma can be detected through observation of a number of physiological changes, such as, denudation of airway epithelium, collagen deposition beneath basement membrane, edema, mast cell activation, inflammatory cell infiltration, including neutrophils, eosinophils, and lymphocytes. As a result of the airway inflammation, asthma patients often experience airway hyper-responsiveness, airflow limitation, respiratory symptoms, and disease chronicity. Airflow limitations include acute bronchoconstriction, airway edema, mucous plug formation, and airway remodeling, features which often lead to bronchial obstruction. In some cases of asthma, sub-basement membrane fibrosis may occur, leading to persistent abnormalities in lung function.

Research over the past several years has revealed that asthma likely results from complex interactions among inflammatory cells, mediators, and other cells and tissues resident in the airways. Mast cells, eosinophils, epithelial cells, macrophage, and activated T cells all play an important role in the inflammatory process associated with asthma. Djukanovic R et al. (1990) *Am Rev Respir Dis* 142:434-457. It is believed that these cells can influence airway function through secretion of preformed and newly synthesized mediators which can act directly or indirectly on the local tissue. It has also been recognized that subpopulations of T lymphocytes (Th2) play an important role in regulating allergic inflammation in the airway by releasing selective cytokines and establishing disease chronicity. Robinson D S et al. (1992) *N Engl J Med* 326:298-304.

Asthma is a complex disorder which arises at different stages in development and can be classified based on the degree of symptoms as acute, subacute, or chronic. An acute inflammatory response is associated with an early recruitment of cells into the airway. The subacute inflammatory response involves the recruitment of cells as well as the activation of resident cells causing a more persistent pattern of inflammation. Chronic inflammatory response is characterized by a persistent level of cell damage and an ongoing repair process, which may result in permanent abnormalities in the airway.

A "subject having asthma" is a subject that has a disorder of the respiratory system characterized by inflammation and narrowing of the airways and increased reactivity of the airways to inhaled agents. Factors associated with initiation of asthma include, but are not limited to, allergens, cold temperature, exercise, viral infections, and $SO_2$.

As mentioned above, asthma may be associated with a Th2-type of immune response, which is characterized at least in part by Th2 cytokines IL-4 and IL-5, as well as antibody isotype switching to IgE. Th1 and Th2 immune responses are mutually counter-regulatory, so that skewing of the immune response toward a Th1-type of immune response can prevent or ameliorate a Th2-type of immune response, including allergy. The modified oligoribonucleotide analogs of the invention are therefore useful by themselves to treat a subject having asthma because the analogs can skew the immune response toward a Th1-type of immune response. Alternatively or in addition, the modified oligoribonucleotide analogs of the invention can be used in combination with an allergen to treat a subject having asthma.

The immunostimulatory composition of the invention may also be administered in conjunction with an asthma therapy. Conventional methods for treating or preventing asthma have involved the use of anti-allergy therapies (described above) and a number of other agents, including inhaled agents.

Medications for the treatment of asthma are generally separated into two categories, quick-relief medications and long-term control medications. Asthma patients take the long-term control medications on a daily basis to achieve and maintain control of persistent asthma. Long-term control medications include anti-inflammatory agents such as corticosteroids, chromolyn sodium and nedocromil; long-acting bronchodilators, such as long-acting $\beta_2$-agonists and methylxanthines; and leukotriene modifiers. The quick-relief medications include short-acting $\beta_2$ agonists, anti-cholinergics, and systemic corticosteroids. There are many side effects associated with each of these drugs and none of the drugs alone or in combination is capable of preventing or completely treating asthma.

Asthma medicaments include, but are not limited, PDE-4 inhibitors, bronchodilator/beta-2 agonists, K+ channel openers, VLA-4 antagonists, neurokin antagonists, thromboxane A2 (TXA2) synthesis inhibitors, xanthines, arachidonic acid antagonists, 5 lipoxygenase inhibitors, TXA2 receptor antagonists, TXA2 antagonists, inhibitor of 5-lipox activation proteins, and protease inhibitors.

Bronchodilator/$\beta_2$ agonists are a class of compounds which cause bronchodilation or smooth muscle relaxation. Bronchodilator/$\beta_2$ agonists include, but are not limited to, salmeterol, salbutamol, albuterol, terbutaline, D2522/formoterol, fenoterol, bitolterol, pirbuerol methylxanthines and orciprenaline. Long-acting $\beta_2$ agonists and bronchodilators are compounds which are used for long-term prevention of symptoms in addition to the anti-inflammatory therapies. Long-acting $\beta_2$ agonists include, but are not limited to, salmeterol and albuterol. These compounds are usually used in combination with corticosteroids and generally are not used without any inflammatory therapy. They have been associated with side effects such as tachycardia, skeletal muscle tremor, hypokalemia, and prolongation of QTc interval in overdose.

Methylxanthines, including for instance theophylline, have been used for long-term control and prevention of symptoms. These compounds cause bronchodilation resulting from phosphodiesterase inhibition and likely adenosine antagonism. Dose-related acute toxicities are a particular problem with these types of compounds. As a result, routine serum concentration must be monitored in order to account for the toxicity and narrow therapeutic range arising from individual differences in metabolic clearance. Side effects include tachycardia, tachyarrhythmias, nausea and vomiting, central nervous system stimulation, headache, seizures, hematemesis, hyperglycemia and hypokalemia. Short-acting $\beta_2$ agonists include, but are not limited to, albuterol, bitolterol, pirbuterol, and terbutaline. Some of the adverse effects associated with the administration of short-acting $\beta_2$ agonists include tachycardia, skeletal muscle tremor, hypokalemia, increased lactic acid, headache, and hyperglycemia.

Chromolyn sodium and nedocromil are used as long-term control medications for preventing primarily asthma symptoms arising from exercise or allergic symptoms arising from allergens. These compounds are believed to block early and late reactions to allergens by interfering with chloride channel function. They also stabilize mast cell membranes and inhibit activation and release of mediators from inosineophils and epithelial cells. A four to six week period of administration is generally required to achieve a maximum benefit.

Anticholinergics are generally used for the relief of acute bronchospasm. These compounds are believed to function by competitive inhibition of muscarinic cholinergic receptors. Anticholinergics include, but are not limited to, ipratropium bromide. These compounds reverse only cholinerigically-mediated bronchospasm and do not modify any reaction to antigen. Side effects include drying of the mouth and respiratory secretions, increased wheezing in some individuals, and blurred vision if sprayed in the eyes.

The immunostimulatory ORN of the invention may also be useful for treating airway remodeling. Airway remodeling results from smooth muscle cell proliferation and/or submucosal thickening in the airways, and ultimately causes narrowing of the airways leading to restricted airflow. The immunostimulatory ORN of the invention may prevent further remodeling and possibly even reduce tissue build-up resulting from the remodeling process.

The immunostimulatory ORN of the invention are also useful for improving survival, differentiation, activation and maturation of dendritic cells. The immunostimulatory oligoribonucleotides have the unique capability to promote cell survival, differentiation, activation and maturation of dendritic cells.

Immunostimulatory ORN of the invention also increase natural killer cell lytic activity and antibody-dependent cellular cytotoxicity (ADCC). ADCC can be performed using an immunostimulatory ORN in combination with an antibody specific for a cellular target, such as a cancer cell. When the immunostimulatory ORN is administered to a subject in conjunction with the antibody, the subject's immune system is induced to kill the tumor cell. The antibodies useful in the ADCC procedure include antibodies which interact with a cell in the body. Many such antibodies specific for cellular targets have been described in the art and many are commercially available. In one embodiment the antibody is an IgG antibody.

In certain aspects the invention provides a method for enhancing epitope spreading. "Epitope spreading" as used herein refers to the diversification of epitope specificity from an initial focused, dominant epitope-specific immune response, directed against a self or foreign protein, to subdominant and/or cryptic epitopes on that protein (intramolecular spreading) or other proteins (intermolecular spreading). Epitope spreading results in multiple epitope-specific immune responses.

The immune response consists of an initial magnification phase, which can either be deleterious, as in autoimmune disease, or beneficial, as in vaccinations, and a later down-regulatory phase to return the immune system to homeostasis and generate memory. Epitope spreading may be an important component of both phases. The enhancement of epitope spreading in the setting of a tumor allows the subject's immune system to determine additional target epitopes, not initially recognized by the immune system in response to an original therapeutic protocol, while reducing the possibility of escape variants in the tumor population and thus affect progression of disease.

The oligoribonucleotides of the invention may be useful for promoting epitope spreading in therapeutically beneficial indications such as cancer, viral and bacterial infections, and allergy. The method in one embodiment includes the steps of administering a vaccine that includes an antigen and an adjuvant to a subject and subsequently administering to the subject at least two doses of immunostimulatory ORN of the invention in an amount effective to induce multiple epitope-specific immune responses. The method in one embodiment includes the steps of administering a vaccine that includes a tumor antigen and an adjuvant to a subject and subsequently administering to the subject at least two doses of immunostimulatory ORN of the invention in an amount effective to induce multiple epitope-specific immune responses. The method in one embodiment involves applying a therapeutic protocol which results in immune system antigen exposure in a subject, followed by at least two administrations of an immunostimulatory oligoribonucleotide of the invention, to induce multiple epitope-specific immune responses, i.e., to promote epitope spreading. In various embodiments the therapeutic protocol is surgery, radiation, chemotherapy, other cancer medicaments, a vaccine, or a cancer vaccine.

The therapeutic protocol may be implemented in conjunction with an immunostimulant, in addition to the subsequent immunostimulant therapy. For instance, when the therapeutic protocol is a vaccine, it may be administered in conjunction with an adjuvant. The combination of the vaccine and the adjuvant may be a mixture or separate administrations, i.e., injections (i.e., same drainage field). Administration is not necessarily simultaneous. If non-simultaneous injection is used, the timing may involve pre-injection of the adjuvant followed by the vaccine formulation.

After the therapeutic protocol is implemented, immunostimulant monotherapy begins. The optimized frequency, duration, and site of administration will depend on the target and other factors, but may for example be a monthly to bimonthly administration for a period of six months to two years. Alternatively the administration may be on a daily, weekly, or biweekly basis, or the administration may be multiple times during a day, week or month. In some instances, the duration of administration may depend on the length of therapy, e.g., it may end after one week, one month, after one year, or after multiple years. In other instances the monotherapy may be continuous as with an intravenous drip. The immunostimulant may be administered to a drainage field common to the target.

For use in therapy, different doses may be necessary for treatment of a subject, depending on activity of the compound, manner of administration, purpose of the immunization (i.e., prophylactic or therapeutic), nature and severity of the disorder, age and body weight of the subject. The administration of a given dose can be carried out both by single administration in the form of an individual dose unit or else several smaller dose units. Multiple administration of doses at specific intervals of weeks or months apart is usual for boosting antigen-specific immune responses.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject. The effective amount for any particular application can vary depending on such factors as the disease or condition being treated, the particular therapeutic agent being administered, the size of the subject, or the severity of the disease or condition. One of ordinary skill in the art can empirically determine the effective amount of a particular nucleic acid and/or other therapeutic agent without necessitating undue experimentation.

Subject doses of the compounds described herein typically range from about 0.1 µg to 10,000 mg, more typically from about 1 µg/day to 8000 mg, and most typically from about 10 µg to 100 µg. Stated in terms of subject body weight, typical dosages range from about 0.1 µg to 20 mg/kg/day, more typically from about 1 to 10 mg/kg/day, and most typically from about 1 to 5 mg/kg/day.

The pharmaceutical compositions containing nucleic acids and/or other compounds can be administered by any suitable route for administering medications. A variety of administration routes are available. The particular mode selected will depend, of course, upon the particular agent or agents selected, the particular condition being treated, and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed herein. For use in therapy, an effective amount of the nucleic acid and/or other therapeutic agent can be administered to a subject by any mode that delivers the agent to the desired surface, e.g., mucosal, systemic.

Administering the pharmaceutical composition of the present invention may be accomplished by any means known to the skilled artisan. Routes of administration include but are not limited to oral, parenteral, intravenous, intramuscular, intraperitoneal, intranasal, sublingual, intratracheal, inhalation, subcutaneous, ocular, vaginal, and rectal. For the treatment or prevention of asthma or allergy, such compounds are preferably inhaled, ingested or administered by systemic routes. Systemic routes include oral and parenteral. Inhaled medications are preferred in some embodiments because of the direct delivery to the lung, the site of inflammation, primarily in asthmatic patients. Several types of devices are regularly used for administration by inhalation. These types of devices include metered dose inhalers (MDI), breath-actuated MDI, dry powder inhaler (DPI), spacer/holding chambers in combination with MDI, and nebulizers.

The therapeutic agents of the invention may be delivered to a particular tissue, cell type, or to the immune system, or both, with the aid of a vector. In its broadest sense, a "vector" is any vehicle capable of facilitating the transfer of the compositions to the target cells. The vector generally transports the immunostimulatory nucleic acid, antibody, antigen, and/or disorder-specific medicament to the target cells with reduced degradation relative to the extent of degradation that would result in the absence of the vector.

In general, the vectors useful in the invention are divided into two classes: biological vectors and chemical/physical vectors. Biological vectors and chemical/physical vectors are useful in the delivery and/or uptake of therapeutic agents of the invention.

Most biological vectors are used for delivery of nucleic acids and this would be most appropriate in the delivery of therapeutic agents that are or that include immunostimulatory nucleic acids.

In addition to the biological vectors discussed herein, chemical/physical vectors may be used to deliver therapeutic agents including immunostimulatory nucleic acids, antibodies, antigens, and disorder-specific medicaments. As used herein, a "chemical/physical vector" refers to a natural or synthetic molecule, other than those derived from bacteriological or viral sources, capable of delivering the nucleic acid and/or other medicament.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vesicles (LUVs), which range in size from 0.2-4.0 µm can encapsulate large macromolecules. RNA, DNA and intact virions can be encapsulated within the aqueous interior and be delivered to cells in a biologically active form. Fraley et al. (1981) *Trends Biochem Sci* 6:77.

Liposomes may be targeted to a particular tissue by coupling the liposome to a specific ligand such as a monoclonal antibody, sugar, glycolipid, or protein. Ligands which may be useful for targeting a liposome to an immune cell include, but are not limited to: intact or fragments of molecules which interact with immune cell specific receptors and molecules, such as antibodies, which interact with the cell surface markers of immune cells. Such ligands may easily be identified by binding assays well known to those of skill in the art. In still other embodiments, the liposome may be targeted to the cancer by coupling it to a one of the immunotherapeutic antibodies discussed earlier. Additionally, the vector may be coupled to a nuclear targeting peptide, which will direct the vector to the nucleus of the host cell.

Lipid formulations for transfection are commercially available from QIAGEN, for example, as EFFECTENE™ (a non-liposomal lipid with a special DNA condensing enhancer) and SUPERFEC™ (a novel acting dendrimeric technology).

Liposomes are commercially available from Gibco BRL, for example, as LIPOFECTIN™ and LIPOFECTACE™, which are formed of cationic lipids such as N-[1-(2,3 dioleyloxy)-propyl]-N,N, N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) *Trends Biotechnol* 3:235-241.

Certain cationic lipids, including in particular N-[1-(2,3 dioleoyloxy)-propyl]-N,N,N-trimethylammonium methylsulfate (DOTAP), appear to be especially advantageous when combined with the modified oligoribonucleotide analogs of the invention.

In one embodiment, the vehicle is a biocompatible microparticle or implant that is suitable for implantation or administration to the mammalian recipient. Exemplary bioerodible implants that are useful in accordance with this method are described in PCT International application no. PCT/US/03307 (Publication No. WO95/24929, entitled "Polymeric Gene Delivery System". PCT/US/0307 describes a biocompatible, preferably biodegradable polymeric matrix for containing an exogenous gene under the control of an appropriate promoter. The polymeric matrix can be used to achieve sustained release of the therapeutic agent in the subject.

The polymeric matrix preferably is in the form of a microparticle such as a microsphere (wherein the nucleic acid and/or the other therapeutic agent is dispersed throughout a solid polymeric matrix) or a microcapsule (wherein the nucleic acid and/or the other therapeutic agent is stored in the core of a polymeric shell). Other forms of the polymeric matrix for containing the therapeutic agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and the nucleic acid and/or the other therapeutic agent are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time. In some preferred embodiments, the nucleic acid are administered to the subject via an implant while the other therapeutic agent is administered acutely. Biocompatible microspheres that are suitable for delivery, such as oral or mucosal delivery, are disclosed in Chickering et al. (1996) *Biotech Bioeng* 52:96-101 and Mathiowitz E et al. (1997) *Nature* 386:410-414 and PCT Pat. Application WO97/03702.

Both non-biodegradable and biodegradable polymeric matrices can be used to deliver the nucleic acid and/or the other therapeutic agent to the subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable, particularly for the nucleic acid agents. The polymer optionally is in the form of a hydrogel that can absorb up to about 90% of its weight in water and further, optionally is cross-linked with multi-valent ions or other polymers.

Bioadhesive polymers of particular interest include bio-erodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

If the therapeutic agent is a nucleic acid, the use of compaction agents may also be desirable. Compaction agents also can be used alone, or in combination with, a biological or chemical/physical vector. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver a nucleic acid in a form that is more efficiently taken up by the cell or, more preferably, in combination with one or more of the above-described vectors.

Other exemplary compositions that can be used to facilitate uptake of a nucleic acid include calcium phosphate and other chemical mediators of intracellular transport, microinjection compositions, electroporation and homologous recombination compositions (e.g., for integrating a nucleic acid into a preselected location within the target cell chromosome).

The compounds may be administered alone (e.g., in saline or buffer) or using any delivery vehicle known in the art. For instance the following delivery vehicles have been described: cochleates (Gould-Fogerite et al., 1994, 1996); Emulsomes (Vancott et al., 1998, Lowell et al., 1997); ISCOMs (Mowat et al., 1993, Carlsson et al., 1991, Hu et., 1998, Morein et al., 1999); liposomes (Childers et al., 1999, Michalek et al., 1989, 1992, de Haan 1995a, 1995b); live bacterial vectors (e.g., *Salmonella, Escherichia coli, Bacillus Calmette-Guérin, Shigella, Lactobacillus*) (Hone et al., 1996, Pouwels et al., 1998, Chatfield et al., 1993, Stover et al., 1991, Nugent et al., 1998); live viral vectors (e.g., Vaccinia, adenovirus, Herpes Simplex) (Gallichan et al., 1993, 1995, Moss et al., 1996, Nugent et al., 1998, Flexner et al., 1988, Morrow et al., 1999); microspheres (Gupta et al., 1998, Jones et al., 1996, Maloy et al., 1994, Moore et al., 1995, O'Hagan et al., 1994, Eldridge et al., 1989); nucleic acid vaccines (Fynan et al., 1993, Kuklin et al., 1997, Sasaki et al., 1998, Okada et al., 1997, Ishii et al., 1997); polymers (e.g. carboxymethylcellulose, chitosan) (Hamajima et al., 1998, Jabbal-Gill et al., 1998); polymer rings (Wyatt et al., 1998); proteosomes (Vancott et al., 1998, Lowell et al., 1988, 1996, 1997); sodium fluoride (Hashi et al., 1998); transgenic plants (Tacket et al., 1998, Mason et al., 1998, Haq et al., 1995); virosomes (Gluck et al., 1992, Mengiardi et al., 1995, Cryz et al., 1998); and, virus-like particles (Jiang et al., 1999, Leibl et al., 1998).

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

For oral administration, the compounds (i.e., nucleic acids, antigens, antibodies, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) *Science* 249:1527-1533, which is incorporated herein by reference.

The nucleic acids and optionally other therapeutics and/or antigens may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Other delivery systems can include time-release, delayed release or sustained release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

The present invention is further illustrated by the following Examples, which in no way should be construed as further limiting.

EXAMPLES

Example 1

Responsiveness of Human PBMC to $N$-$U$-$R_1$-$R_2$,-Containing Oligoribonucleotides Methods: Luminex Technology Luminex color-codes tiny beads, called microspheres, into 100 distinct sets. Each bead set can be coated with a reagent specific to a particular bioassay, allowing the capture and detection of specific analytes from a sample. Within the Luminex compact analyzer, lasers excite the internal dyes that identify each microsphere particle, and also any reporter dye captured during the assay. Many readings are made on each bead set, further validating the results. In this way, Luminex technology allows multiplexing of up to 100 unique assays within a single sample, both rapidly and precisely.

Figure 3:
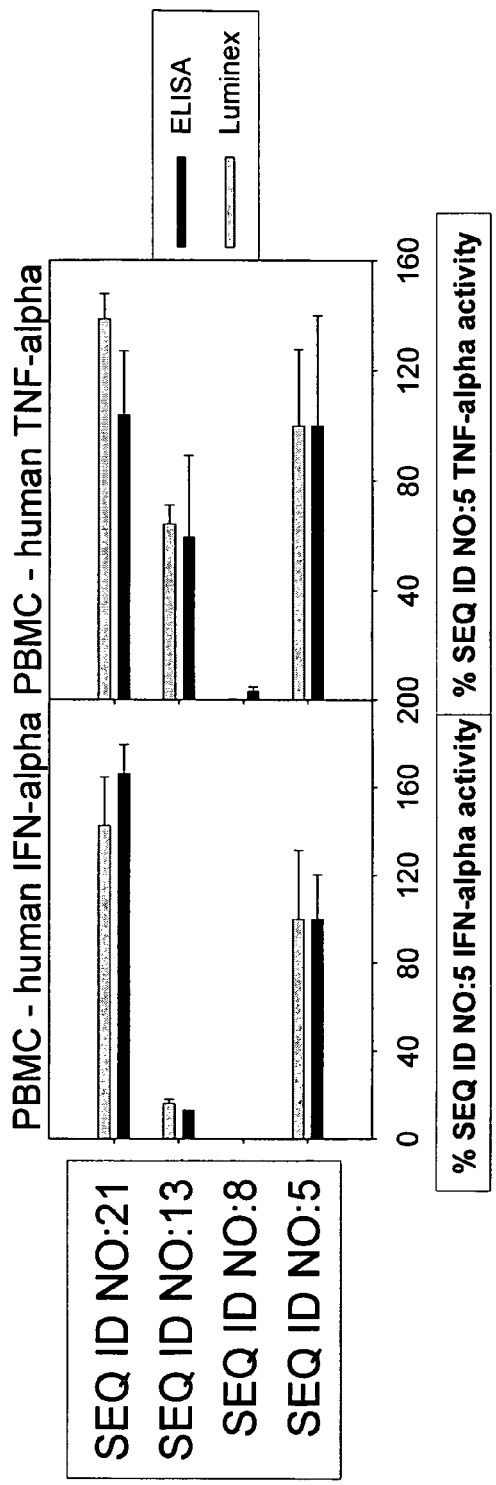
FIG. 3 is a set of bar graphs depicting ORN induced cytokine production upon PBMC stimulation. Human PBMC were stimulated with the indicated ORN (0.5 µM ORN) complexed to 10 µg/ml DOTAP and IFN-alpha (FIG. 3A) and TNF-alpha (FIG. 3B) were measured and cytokine production was measured by the ELISA technique and Luminex technique compared.

Human peripheral blood mononuclear cells (PBMCs) were isolated from healthy donors, plated, and stimulated in vitro with various test and control immunostimulatory agents for 16 hours. After 16 hours, the supernatants were collected and then analyzed by ELISA assay. N-U-$R_1$-$R_2$,-Containing Oligoribonucleotides were tested complexed to DOTAP and with full titration curves (7 concentrations), starting from 2 µM ORN complexed to 25 µg/ml DOTAP and with 1/3 dilution steps. Also included were certain negative controls, including medium alone and DOTAP (25 µg/ml culture well; "Liposomes") alone. The control immunostimulatory agents included the imidazoquinoline R-848 (2 µM with 1/3 dilution steps and 7 concentrations) the reported ligand for TLR7, ORN having TLR8 motifs such as AU and AUU sequences (SEQ ID NO:13-SEQ ID NO:15) ORN having TLR7/8 motifs such as CU, GU and GUU sequences (SEQ ID NO:19-SEQ ID NO:23). The results are shown in FIGS. 1 and 3.

A similar assay testing different ORN sequences was performed using isolated pDC, monocytes and mDC stimulation. Cells were stimulated with 0.5 µM ORN complexed to 10 µg/ml DOTAP, 0.5 µM CpG ODN or DOTAP or media alone. After 16 h the supernatants were harvested and IFN-alpha, TNF-alpha and IL-12p40 levels were measured by ELISA. The results are shown in FIG. 2.

FIG. 1 shows a clear difference between TNF-alpha and IFN-alpha production upon PBMC stimulation for SEQ ID NO:12 containing an AU sequence and SEQ ID NO:21 containing a GU sequence. Further sequence analysis revealed that a CUA repetition (SEQ ID NO:24) is an additional TNF-alpha inducing ORN with no IFN-alpha production. Shorter ORN containing AU and GU repetitions (SEQ ID NO:29-SEQ ID NO:34) showed similar results compared to longer ones (SEQ ID NO:12-SEQ ID NO:23) but with a drop in efficacy and potency.

Figure 2:
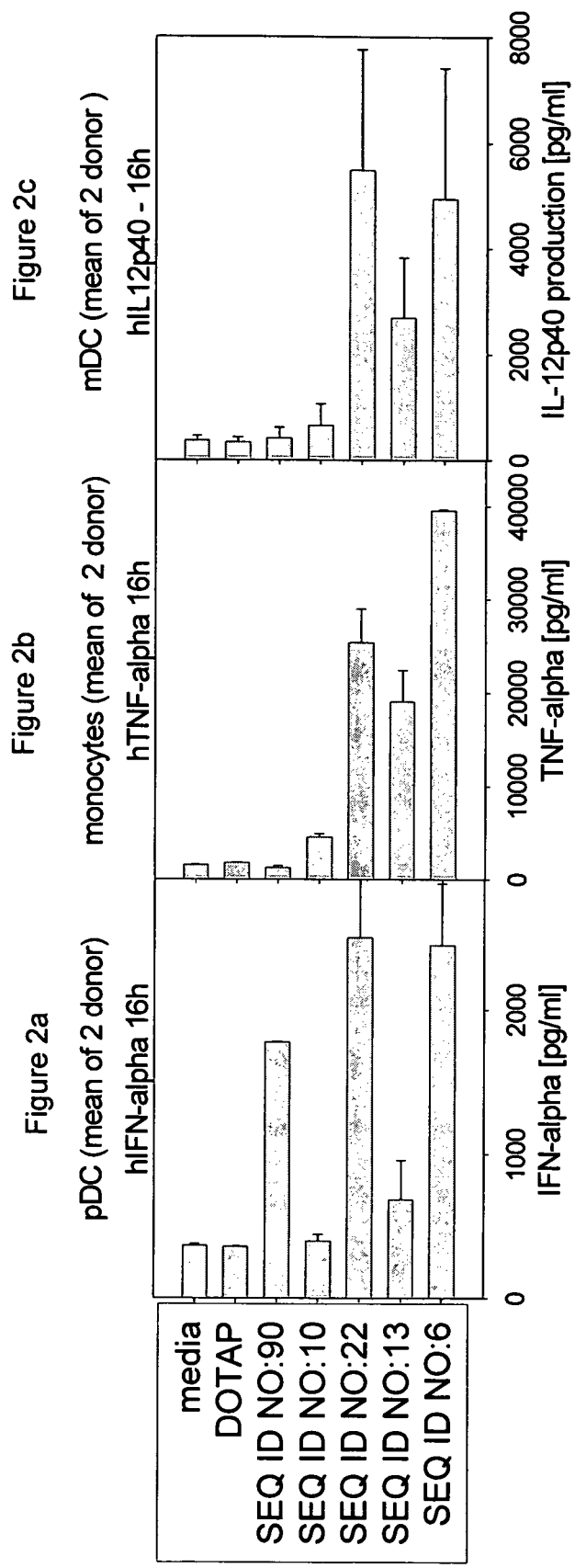
FIG. 2 is a set of bar graphs depicting ORN induced cytokine production upon isolated pDC (FIG. 2a), monocytes (FIG. 2b) and mDC (FIG. 2c) stimulation. Cells were stimulated with 0.5 µM ORN complexed to 10 µg/ml DOTAP, 0.5 µM CpG ODN or DOTAP or media alone and IFN-alpha (FIG. 2a), TNF-alpha (FIG. 2c) and IL-12p40 (FIG. 2c) were measured.

FIGS. 2 and 6 show analysis of AU-ORN (SEQ ID NO:13) and GU-ORN (SEQ ID NO:21) on isolated monocytes, pDCs and mDCs reflecting strongly reduced IFN-alpha production for AU-ORN (SEQ ID NO:13) and clear TNF-alpha and IL-12p40 production for both ORN. IFN-alpha production upon ORN stimulation from pDC appears to be TLR7 mediated while TNF-alpha and IL-12p40 production from isolated monocytes and mDC appears to be TLR8 mediated.

Figure 8:
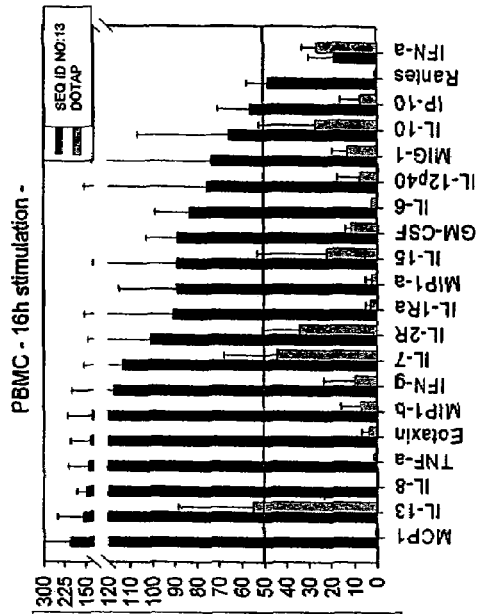
FIG. 8 is a set of bar graphs showing differences between TLR8 (SEQ ID NO:13) and TLR7/8 (SEQ ID NO:21) ORN. The cells were stimulated with ORN (4 concentrations, starting from 1 µM with 1/4 dilution) complexed to DOTAP (starting from 25 µg/ml with 1/4 dilutions). After 16 hours the supernatents were harvested and cytokine production measured by Luminex technology. The graphic showed the measured mean max at any concentration cytokine production as percent of the TLR8 ORN (SEQ ID NO:13) to the TLR7/8 ORN (SEQ ID NO:21). This is shown for isolated pDC, PBMC, isolated monocytes and CD123-CD14− PBMC.
Figure 8:
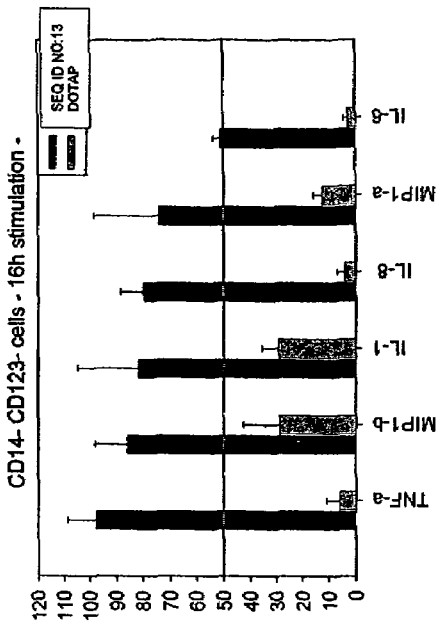
Figure 8:
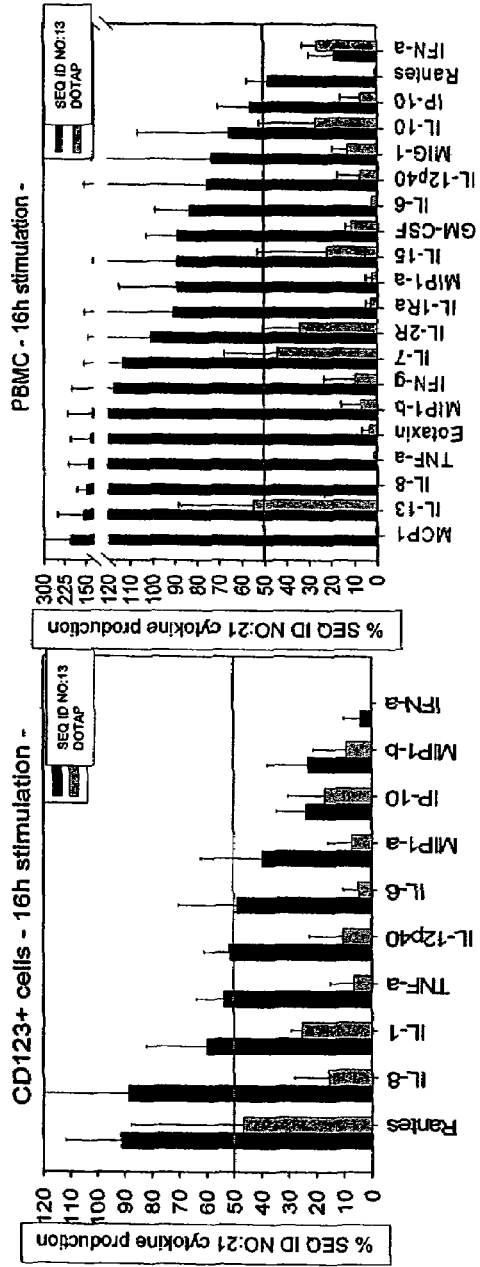
Figure 8:
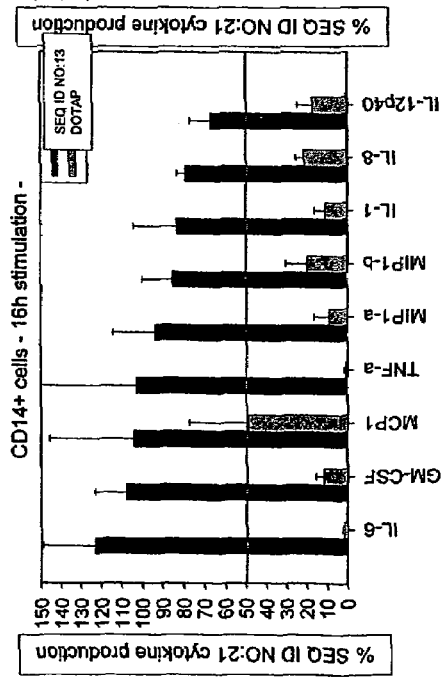

Luminex results reflected comparable results to ELISA data and proved that the major difference between GU-ORN and AU-ORN is due to IFN-alpha production and IFN-alpha related genes/cytokines (FIGS. 3 and 8a). In addition, further Luminex data showed that in contrast to IFN-alpha and IFN-alpha related genes/cytokines the other cytokines/chemokines are unaffected (FIGS. 7 and 8a-d) with one outlier IL-6 from CD123-CD14- cells. This IL-6 production might be due to TLR7 mediated B-cell activation.

Example 2

Comparison of IFN-Alpha and TNF-Alpha Max Activities of Oligoribonucleotides

Figure 4:
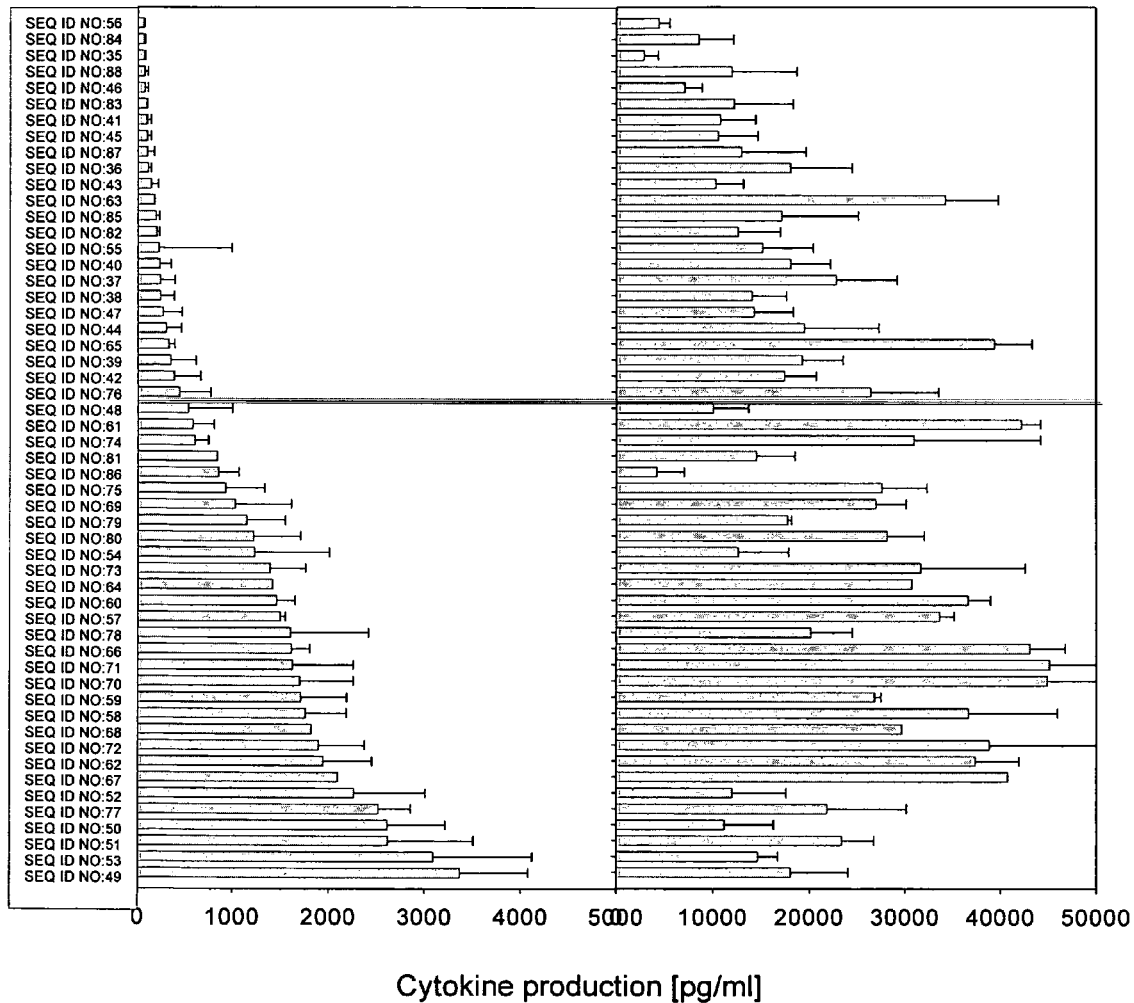
FIG. 4 is a bar graph demonstrating a comparison of IFN-alpha (FIG. 4a) and TNF-alpha (FIG. 4b) max activities of the indicated ORN. Human PBMC were stimulated with ORN (7 concentrations, starting from 2 µM with 1/3 dilution) complexed to DOTAP (starting from 25 µg/ml with 1/3 dilutions) and Mean Max activities at 0.6 µM of 3-6 Blood Donors in two individual experiments were assessed.

Human PBMC were stimulated with ORN complexed to DOTAP. After 16 hours supernatants were harvested and TNF-alpha and IFN-alpha levels were measured. Mean/Max activities at 0.6 µM of 3-6 blood donors and two individual experiments were determined. The results are shown in FIG. 4. These data clearly differentiate between the TLR8 and TLR7/8 motifs: ORN with the motif N-U-$R_1$-$R_2$ showed IFN-alpha production under 300 pg/ml while TLR7/8 ORN showed higher IFN-alpha production upon PBMC stimulation (FIG. 4a). TLR8 and TLR7/8 ORN are divided by a red line. In contrast, measurements of TNF-alpha levels indicated that both ORN with the TLR8 and ORN with the TLR7/8 motif stimulate TNF-alpha production.

Example 3

Comparison of IFN-Alpha Max Activity to IFN-Alpha EC50 of Oligoribonucleotides

Figure 5:
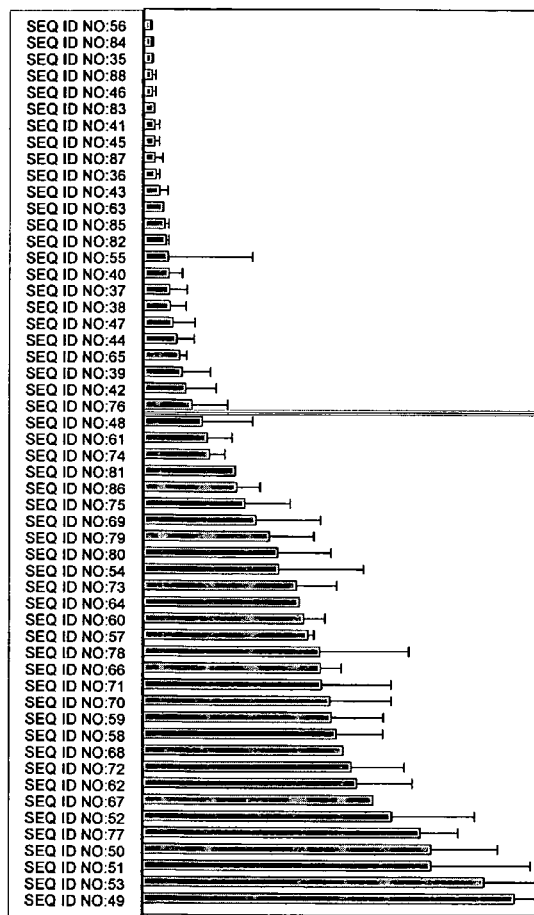
FIG. 5 is a bar graph demonstrating a comparison of IFN-alpha max activity (FIG. 5a) to IFN-alpha EC50 (FIG. 5b). Human PBMC were stimulated with ORN complexed to DOTAP and IFN-alpha was measured.
Figure 5:
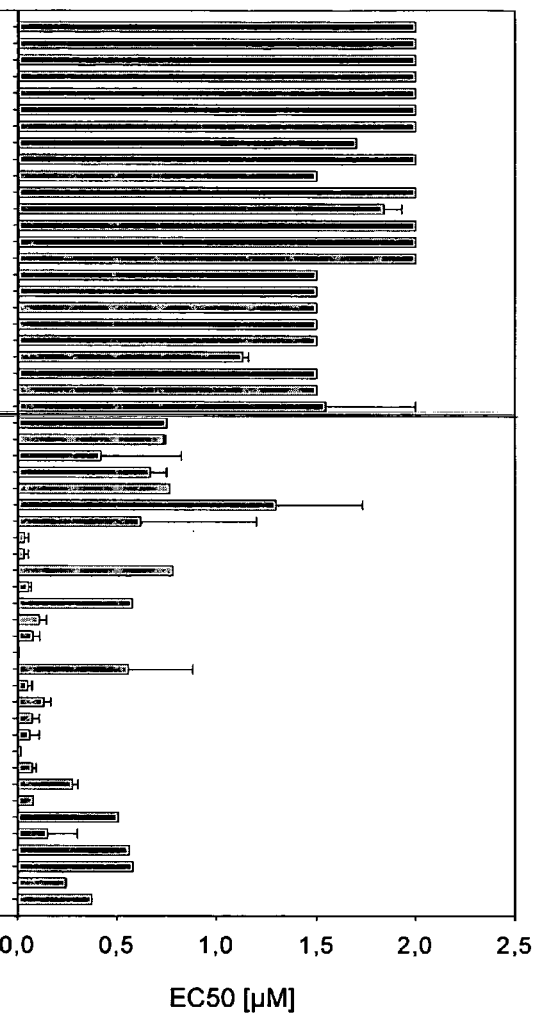
Figure 7:
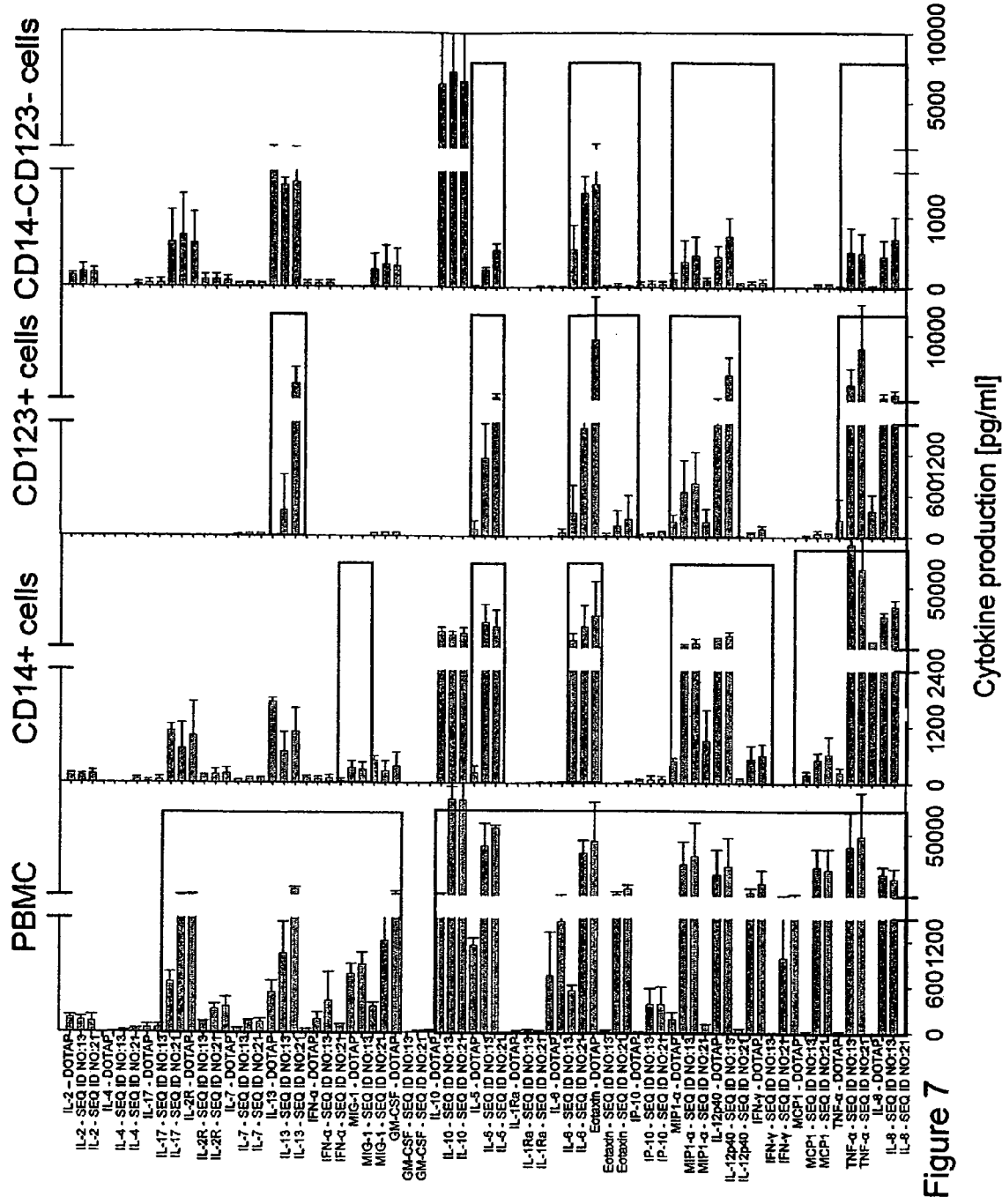
FIG. 7 shows a set of bar graphs demonstrating the mean max activities at any concentration of 3 Blood Donors for PBMC, isolated monocytes, isolated pDC and CD14-CD123− PBMC. The cells were stimulated with ORN (4 concentrations, starting from 1 µM with 1/4 dilution) complexed to DOTAP (starting from 25 µg/ml with 1/4 dilutions). After 16 hours the supernatents were harvested and cytokine production measured by Luminex technology. Red squared indicated positive reactions over background of DOTAP and media.

Human PBMC were stimulated with ORN complexed to DOTAP. After 16 hours supernatants were harvested and IFN-alpha levels were measured. Mean/Max activities at 0.6 µM and EC50 of full titration curves (range: 2 µM to 0.9 nM) of 3-6 blood donors and two individual experiments were determined. The results are shown in FIG. 5. EC50 and Max activities showed comparable results concerning the TLR8 and TLR7/8 motifs. Low EC50/high Max activity represents TLR7/8 ORN (FIG. 5a) whereas high EC50 and low Max activity represents TLR8 ORN (FIG. 5b).

The ORN sequences listed in Table 1 were tested for IFN-alpha and TNF-alpha production upon human PBMC stimulation. Human PBMC were stimulated for 16 h with the indicated ORN, and supernatants were harvested and cytokine production measured by ELISA. Table 2 summarizes the min/max activity and EC50 of ORN for IFN-alpha and TNF-alpha production.

TABLE 1

| | | IFN-alpha | TNF-alpha |
|---|---|---|---|
| SEQ ID NO: 1 | G*U*A*G*G*C*A*C | − | + |
| SEQ ID NO: 2 | U*U*A*G*G*C*A*C | − | + |
| SEQ ID NO: 3 | C*U*A*G*G*C*A*C | − | + |
| SEQ ID NO: 4 | A*U*A*G*G*C*A*C | − | + |
| SEQ ID NO: 7 | dN*dN*dN*dN*dN*N*A*U*A*U*N*N*dN*dN*dN*dN*dN*dN | − | + |
| SEQ ID NO: 9 | dN*dN*dN*dN*dN*A*U*A*U*A*U*A*U*dN*dN*dN*dN*dN*dN | − | + |
| SEQ ID NO: 11 | G*C*C*A*C*C*G*A*G*C*C*G*A*A*U*A*U*A*C*C | − | + |
| SEQ ID NO: 12 | A*U*A*U*A*U*A*U*A*U*A*U*A*U*A*U*A*U*A*U | − | + |
| SEQ ID NO: 13 | U*U*A*U*U*A*U*U*A*U*U*A*U*U*A*U*U*A*U*U | − | + |
| SEQ ID NO: 14 | U*U*U*A*U*U*U*A*U*U*U*A*U*U*U*A*U*U*U*A | + | + |
| SEQ ID NO: 15 | U*U*U*U*A*U*U*U*U*A*U*U*U*U*A*U*U*U*U*A | + | + |
| SEQ ID NO: 16 | A*A*U*A*A*U*A*A*U*A*A*U*A*A*U*A*A*U*A*A | − | + |
| SEQ ID NO: 17 | A*A*A*U*A*A*A*U*A*A*A*U*A*A*A*U*A*A*A*U | − | + |

TABLE 1-continued

| | IFN-alpha | TNF-alpha |
|---|---|---|
| SEQ ID NO: 18 A*A*A*U*A*A*A*A*U*A*A*A*A*U*A*A*A*U | − | + |
| SEQ ID NO: 19 C*U*C*U*C*U*C*U*C*U*C*U*C*U*C*U*C*U | + | + |
| SEQ ID NO: 20 G*U*G*U*G*U*G*U*G*U*G*U*G*U*G*U*G*U | + | + |
| SEQ ID NO: 21 U*G*U*U*G*U*U*G*U*U*G*U*U*G*U*U*G*U | + | + |
| SEQ ID NO: 22 U*U*U*G*U*U*U*G*U*U*U*G*U*U*U*G*U*U*G | + | + |
| SEQ ID NO: 23 U*U*U*U*G*U*U*U*U*G*U*U*U*U*G*U*U*U*U*G | + | + |
| SEQ ID NO: 24 C*U*A*C*U*A*C*U*A*C*U*A*C*U*A*C*U | − | + |
| SEQ ID NO: 25 G*U*A*G*U*A*G*U*A*G*U*A*G*U*A*G*U | + | + |
| SEQ ID NO: 26 G*U*C*G*U*C*G*U*C*G*U*C*G*U*C*G*U*C*G*U | + | + |
| SEQ ID NO: 27 I*U*A*I*U*A*I*U*A*I*U*A*I*U*A*I*U | + | + |
| SEQ ID NO: 28 U*U*I*U*U*I*U*U*I*U*U*I*U*U*I*U*U | + | + |
| SEQ ID NO: 29 U*G*U*U*G*U | + | + |
| SEQ ID NO: 30 U*A*U*A*U | − | + |
| SEQ ID NO: 31 U*G*U*G*U*G*U | + | + |
| SEQ ID NO: 32 U*C*U*C*U*C*U | + | + |
| SEQ ID NO: 33 U*A*U*A*U*A*U | − | + |
| SEQ ID NO: 34 G*U*A*G*U*A*G | + | + |

+: cytokine production
−: no cytokine production.

TABLE 2

| ORN | IFN-alpha max activity [pg/ml] | | TNF-alpha max activity [pg/ml] | | IFN-alpha EC50 [µM] | | TNF-alpha EC50 [µM] | |
|---|---|---|---|---|---|---|---|---|
| SEQ ID NO: 49 C*C*G*A*G*C*C*G*C*U*U*A*A*C*C*C | 3367 | 710.4 | 18039 | 5982 | 0.375 | 0 | 0.35 | 0 |
| SEQ ID NO: 53 C*C*G*A*G*C*C*G*C*U*U*A*C*C*C | 3091 | 1028 | 14623 | 2088 | 0.244 | 0 | 0.952 | 0 |
| SEQ ID NO: 51 C*C*G*A*G*C*C*G*C*U*A*U*U*C*C*C | 2615 | 893.9 | 23325 | 3378 | 0.582 | 0 | 0.125 | 0 |
| SEQ ID NO: 50 C*C*G*A*G*C*C*G*C*A*A*U*U*C*C*C | 2614 | 599.2 | 11141 | 5133 | 0.562 | 0 | 0.564 | 0 |
| SEQ ID NO: 77 C*C*G*A*G*C*C*G*A*G*U*U*C*A*C*C | 2519 | 336.9 | 21820 | 8316 | 0.151 | 0.15 | 0.257 | 0.095 |
| SEQ ID NO: 52 C*C*G*A*G*C*C*G*C*A*A*U*U*C*C*C | 2263 | 744.8 | 11920 | 5654 | 0.508 | 0 | 0.895 | 0 |
| SEQ ID NO: 67 C*C*G*A*G*C*C*G*A*G*U*U*C*A*C*C | 2094 | 0 | 40729 | 0 | 0.081 | 0 | 0.079 | 0 |
| SEQ ID NO: 62 C*C*G*A*G*C*C*G*A*T*U*G*U*A*C*C | 1945 | 503.8 | 37334 | 4597 | 0.276 | 0.029 | 0.343 | 0.004 |
| SEQ ID NO: 72 C*C*G*A*G*C*C*G*A*U*U*U*T*A*C*C | 1896 | 476.1 | 38811 | 11366 | 0.075 | 0.019 | 0.146 | 0.037 |
| SEQ ID NO: 68 C*C*G*A*G*C*C*G*A*T*U*U*C*A*C*C | 1821 | 0 | 29647 | 0 | 0.018 | 0 | 0.217 | 0 |
| SEQ ID NO: 58 C*C*G*A*G*C*C*G*A*G*U*U*U*A*C*C | 1760 | 423.3 | 36627 | 9350 | 0.063 | 0.047 | 0.203 | 0.08 |
| SEQ ID NO: 59 C*C*G*A*G*C*C*G*A*T*U*U*U*A*C*C | 1714 | 473.8 | 26762 | 691.6 | 0.074 | 0.036 | 0.224 | 0.106 |
| SEQ ID NO: 70 C*C*G*A*G*C*C*G*A*U*T*U*T*A*C*C | 1702 | 554.3 | 44904 | 10972 | 0.132 | 0.035 | 0.15 | 0.029 |
| SEQ ID NO: 71 C*C*G*A*G*C*C*G*A*U*U*U*C*A*C*C | 1626 | 629.7 | 45164 | 13344 | 0.051 | 0.023 | 0.16 | 0.011 |

TABLE 2-continued

| ORN | IFN-alpha max activity [pg/ml] | | TNF-alpha max activity [pg/ml] | | IFN-alpha EC50 [µM] | | TNF-alpha EC50 [µM] | |
|---|---|---|---|---|---|---|---|---|
| SEQ ID NO: 66 C*C*G*A*G*C*C*G*A*U*G*U*U*A*C*C | 1616 | 188.4 | 43098 | 3722 | 0.558 | 0.326 | 0.051 | 0.033 |
| SEQ ID NO: 78 C*C*G*A*G*C*C*G*A*T*U*U*C*A*C*C | 1609 | 805.1 | 20126 | 4342 | 0.006 | 0.002 | 0.241 | 0.139 |
| SEQ ID NO: 57 C*C*G*A*G*C*C*G*A*C*U*U*U*A*C*C | 1499 | 54.8 | 33624 | 1507 | 0.077 | 0.034 | 0.213 | 0.072 |
| SEQ ID NO: 60 C*C*G*A*G*C*C*G*A*A*U*U*U*A*C*C | 1463 | 192.9 | 36562 | 2374 | 0.109 | 0.036 | 0.187 | 0.06 |
| SEQ ID NO: 64 C*C*G*A*G*C*C*G*A*U*C*U*U*A*C*C | 1421 | 0 | 30712 | 0 | 0.577 | 0 | 0.289 | 0 |
| SEQ ID NO: 73 C*C*G*A*G*C*C*G*A*U*U*U*A*A*C*C | 1395 | 367.9 | 31619 | 10958 | 0.055 | 0.013 | 0.163 | 0.024 |
| SEQ ID NO: 54 C*C*G*A*G*C*C*G*C*A*U*U*C*C*C*C | 1233 | 772.4 | 12595 | 5272 | 0.78 | 0 | 0.339 | 0 |
| SEQ ID NO: 80 C*C*G*A*G*C*C*G*A*A*U*U*C*A*C*C | 1225 | 486.6 | 28108 | 3911 | 0.033 | 0.02 | 0.217 | 0.022 |
| SEQ ID NO: 79 C*C*G*A*G*C*C*G*A*T*U*U*C*A*C*C | 1152 | 402.7 | 17728 | 415.8 | 0.035 | 0.02 | 0.334 | 0.138 |
| SEQ ID NO: 69 C*C*G*A*G*C*C*G*A*U*C*U*C*A*C*C | 1031 | 584.8 | 26915 | 3185 | 0.619 | 0.582 | 0.313 | 0.174 |
| SEQ ID NO: 75 C*C*G*A*G*C*C*G*A*U*U*C*T*A*C*C | 929.9 | 408.7 | 27576 | 4712 | 1.297 | 0.433 | 0.129 | 0.071 |
| SEQ ID NO: 86 C*C*G*A*G*C*C*G*A*A*G*G*U*C*C*C | 856.5 | 212.6 | 4178 | 2818 | 0.767 | 0 | 0.85 | 0 |
| SEQ ID NO: 81 C*C*G*A*G*C*C*G*A*G*C*U*C*A*C*C | 842.9 | 0 | 14519 | 3965 | 0.667 | 0.083 | 0.802 | 0.093 |
| SEQ ID NO: 74 C*C*G*A*G*C*C*G*A*U*U*G*C*A*C*C | 609.1 | 141.6 | 30958 | 13275 | 0.419 | 0.408 | 0.329 | 0.067 |
| SEQ ID NO: 61 C*C*G*A*G*C*C*G*A*C*U*G*U*A*C*C | 587.7 | 223.7 | 42180 | 2040 | 0.736 | 0.009 | 0.141 | 0.077 |
| SEQ ID NO: 48 C*C*G*A*G*C*C*G*C*A*U*U*A*C*C*C | 543.4 | 457.8 | 9988 | 3681 | 0.75 | 0 | 0.801 | 0 |
| SEQ ID NO: 76 C*C*G*A*G*C*C*G*A*U*U*G*A*A*C*C | 448.6 | 323.9 | 26371 | 7157 | 1.543 | 0.457 | 0.109 | 0.017 |
| SEQ ID NO: 42 C*C*G*A*G*C*C*G*A*A*U*A*C*C*C*C | 392.4 | 277.9 | 17418 | 3300 | 1.5 | 0 | 0.395 | 0 |
| SEQ ID NO: 39 C*C*G*A*G*C*C*A*U*A*U*A*U*A*U*C | 356.7 | 262.3 | 19253 | 4261 | 1.5 | 0 | 0.324 | 0 |
| SEQ ID NO: 65 C*C*G*A*G*C*C*G*A*U*A*U*U*A*C*C | 335.2 | 63.87 | 39377 | 3971 | 1.131 | 0.03 | 0.077 | 0.002 |
| SEQ ID NO: 44 C*C*G*A*G*C*C*G*A*A*U*C*C*C*C*C | 305.6 | 163.3 | 19473 | 7758 | 1.5 | 0 | 0.321 | 0 |
| SEQ ID NO: 47 C*C*G*A*G*C*C*G*C*C*U*A*C*C*C*C | 271.9 | 204 | 14265 | 4080 | 1.5 | 0 | 0.566 | 0 |
| SEQ ID NO: 38 C*C*G*A*G*C*C*A*U*A*U*A*U*C*C*C | 245 | 148.3 | 14064 | 3564 | 1.5 | 0 | 0.89 | 0 |
| SEQ ID NO: 37 C*C*G*A*G*C*C*G*C*U*A*U*A*C*C*C | 240.5 | 161.2 | 22800 | 6376 | 1.5 | 0 | 0.75 | 0 |

TABLE 2-continued

| ORN | IFN-alpha max activity [pg/ml] | TNF-alpha max activity [pg/ml] | IFN-alpha EC50 [µM] | | TNF-alpha EC50 [µM] | |
|---|---|---|---|---|---|---|
| SEQ ID NO: 40 C*C*G*A*G*C*C*G*A*A*U*A*A*C*C*C | 235.3 | 124.3 | 18083 | 4101 | 1.5 | 0 | 0.352 | 0 |
| SEQ ID NO: 55 C*C*G*A*G*C*C*G*C*U*A*U*C*C*C*C | 224.4 | 772.4 | 15154 | 5272 | 2 | 0 | 0.337 | 0 |
| SEQ ID NO: 82 C*C*G*A*G*C*C*G*A*A*G*U*A*C*C | 204 | 28.62 | 12595 | 4373 | 2 | 0 | 0.219 | 0 |
| SEQ ID NO: 85 C*C*G*A*G*C*C*G*A*A*G*A*U*A*C*C | 193.7 | 37.15 | 17146 | 7964 | 2 | 0 | 0.215 | 0 |
| SEQ ID NO: 63 C*C*G*A*G*C*C*G*A*A*U*G*U*A*C*C | 177.3 | 6.443 | 34219 | 5563 | 1.836 | 0.094 | 0.309 | 0.151 |
| SEQ ID NO: 43 C*C*G*A*G*C*C*G*C*C*U*A*A*C*C*C | 144.3 | 74.51 | 10261 | 2883 | 2 | 0 | 0.954 | 0 |
| SEQ ID NO: 36 C*C*G*A*G*C*C*G*C*A*U*A*U*C*C*C | 110.4 | 32.54 | 18063 | 6409 | 1.5 | 0 | 0.85 | 0 |
| SEQ ID NO: 87 C*C*G*A*G*C*C*G*A*A*G*C*U*A*C*C | 100.5 | 73.84 | 12979 | 6676 | 2 | 0 | 0.346 | 0 |
| SEQ ID NO: 45 C*C*G*A*G*C*C*G*C*A*U*A*C*C*C*C | 98.44 | 42.34 | 10491 | 4195 | 1.7 | 0 | 0.754 | 0 |
| SEQ ID NO: 41 C*C*G*A*G*C*C*G*C*A*U*A*A*C*C*C | 97.97 | 42.23 | 10756 | 3679 | 2 | 0 | 0.897 | 0 |
| SEQ ID NO: 83 C*C*G*A*G*C*C*G*A*A*G*G*U*G*C*C | 96.22 | 2.398 | 12207 | 6121 | 2 | 0 | 0.215 | 0 |
| SEQ ID NO: 46 C*C*G*A*G*C*C*G*C*A*U*C*C*C*C*C | 74.76 | 32.92 | 7096 | 1767 | 2 | 0 | 0.765 | 0 |
| SEQ ID NO: 88 C*C*G*A*G*C*C*G*A*A*G*C*U*G*C*C | 73.19 | 34.21 | 11996 | 6696 | 2 | 0 | 2 | 0 |
| SEQ ID NO: 35 C*C*G*A*G*C*C*G*C*C*G*C*C*C*C*C | 70.6 | 11.78 | 2854 | 1505 | 2 | 0 | 2 | 0 |
| SEQ ID NO: 84 C*C*G*A*G*C*C*G*A*A*G*C*U*C*C*C | 67.76 | 15.71 | 8545 | 3592 | 2 | 0 | 0.377 | 0 |
| SEQ ID NO: 56 C*C*G*A*G*C*C*G*A*A*G*G*C*A*C*C | 59.84 | 8.006 | 4430 | 1124 | 2 | 0 | 2 | 0 |

Example 4

Synthetic ORN Differentiate Between IFN-Alpha and TNF-Alpha Release Upon Human PBMC Stimulation CD123+ purified pDC (FIGS. 10a and 10b) or isolated monocytes (FIG. 10c) were incubated with 1 µM ORN complexed to 25 µg/ml DOTAP or DOTAP alone (FIG. 10a) or indicated amounts of ORN complexed to DOTAP or DOTAP alone (FIGS. 10b-10c). After 16 h cells were harvested and stained with CD123, CD11c and HLA-DR antibodies (FIGS. 10a and 10b) or CD14 and CD19 (FIG. 10c). FACS analysis for CD86 shows that AU-rich ORN (SEQ ID NO:13) and GU-rich ORN (SEQ ID NO:21) show differences in CD86 surface marker expression upon pDC stimulation (FIG. 10a). Stimulation with AU-rich ORN SEQ ID NO:13 resulted in very little CD86 activation, whereas stimulation with GU-rich ORN SEQ ID NO:21 resulted in significant CD86 activation. This activation was determined to be dose-dependent (FIG. 10b). AU-rich ORN (SEQ ID NO:13) and GU-rich ORN (SEQ ID NO:21) showed no difference in CD80 surface marker expression upon human PBMC (data not shown) and CD14-positive cell stimulation (FIG. 10c).

Example 5

Figure 9:
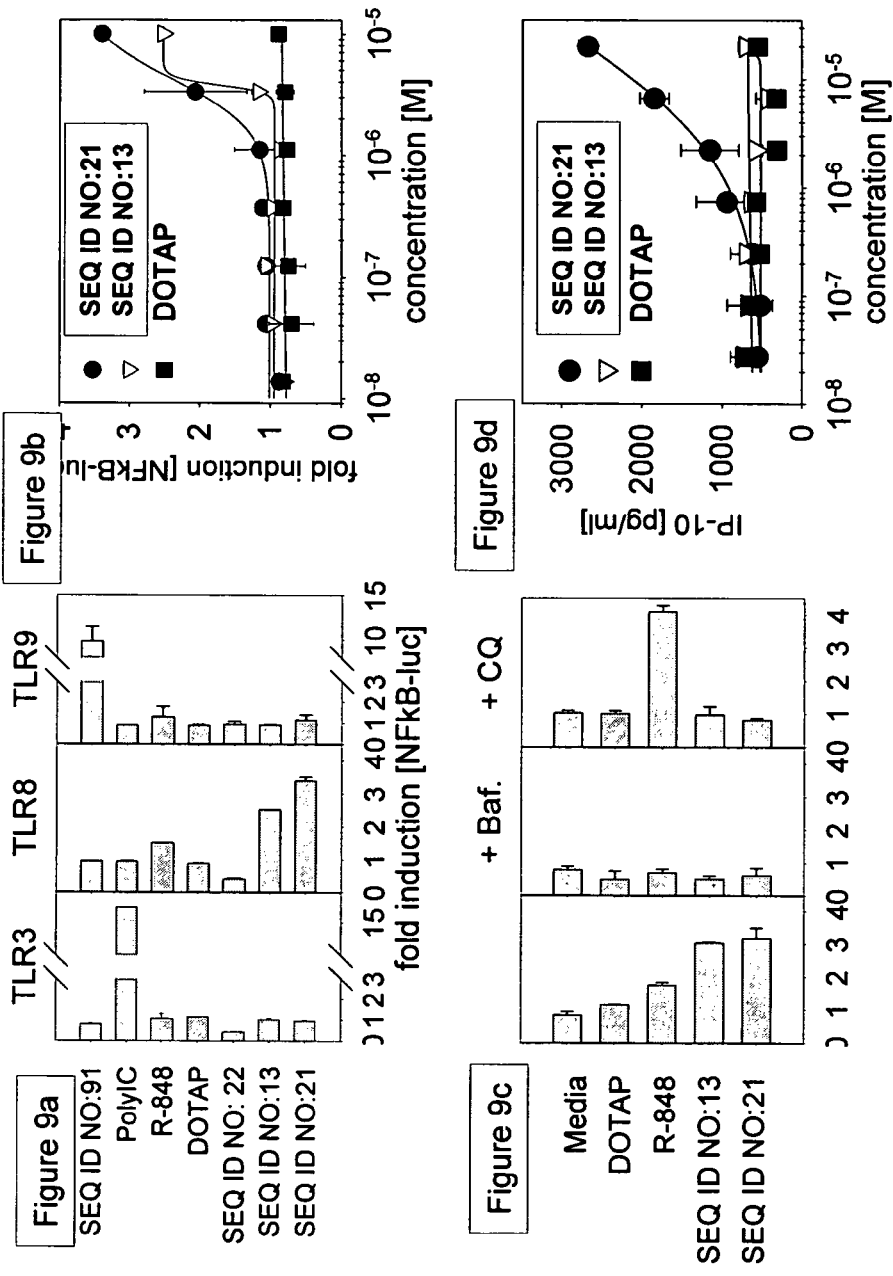
FIG. 9 is a set of bar graphs and curves that shows reaction of TLR8 ORN (SEQ ID NO:13) and TLR7/8 ORN (SEQ ID NO:21) acting via TLR8 within stable-transfected HEK-293 cells. Stable-transfected HEK-293 cells with NFκB-luciferase read out reporter and human TLR8 were stimulated for 16 hours with indicated ORN. After 16 hours the supernatants were removed, the cells lysed and the luciferase activity or cytokine level was measured.

A U-Rich ORN (SEQ ID NO:13) and GU-Rich ORN (SEQ ID NO:21) Stimulate Specific Human TLR8 Signaling in a Dose Dependent Manner Unresponsive HEK-293 cells were stably transfected with human TLR3 or TLR8 expression plasmid and NFκB-luciferase reporter gene construct. Cells were incubated with the indicated ORN sequences (10 µM complexed to 50 µg/ml DOTAP) or control stimuli (10 µM R-848, 50 µg/ml polyIC, 3.3 µM ODN 10103 or 50 µg/ml DOTAP) for 16 hours. NFκB-activation was measured by assaying luciferase activity. Results are given as fold induction above background (medium). One representative experiment of 6 independent repetitions is presented (FIG. 9a).

Stable-transfected HEK-293 cells expressing human TLR8 were stimulated with indicated concentrations of ORN complexed to DOTAP (50 µg/ml->1/3 dilution) or DOTAP alone (50 µg/ml->1/3 dilution) for 16 hours. NFκB activation was measured by assaying luciferase activity. Results are given as fold induction above background (medium). One representative experiment of 3 independent repetitions is presented (FIG. 9b).

Unresponsive HEK-293 cells were stably transfected with human TLR8 expression plasmid and NFκB-luciferase reporter gene construct. Cells were incubated with the indicated ORN sequences (15 µM complexed to 75 µg/ml DOTAP) or control stimuli (15 µM R-848 or 75 µg/ml DOTAP) and with media (left), 200 nM Bafilomycin (Baf., middle) or 1 mM Chloroquine (CQ, right) for 16 h. NFκB-activation was measured by assaying luciferase activity. Results are given as fold induction above background (medium). One representative experiment of 4 independent repetitions is presented (FIG. 9c).

RPMI 8226 cells were pre-incubated with 1000 U/ml Intron A for 3 hours, washed twice with media and then stimulated for 16 hours with the indicated concentrations of ORN complexed to DOTAP (50 µg/ml->1/3 dilution). Cytokine release of IP-10 was measured by ELISA. Results are given as pg/ml. One representative experiment of 3 independent repetitions is presented (FIG. 9d).

These data demonstrate the specificity of SEQ ID NO:13 and SEQ ID NO:21 for TLR8

The assay was repeated with a TLR8 ORN (SEQ ID NO:13), a TLR 7/8 ORN (SEQ ID NO:21) and a control ORN (SEQ ID NO:5) (Table 3) at both a high dose (H.D., 10 µg/ml) and a low dose (L.D., 2.5 µg/ml). Only SEQ ID NO:21 treatment resulted in significant production of IL-12 and TNF-alpha (FIGS. 11a and 11b, respectively). All ORN stimulated production of IFN-γ (FIG. 11c).

| SEQ ID NO | ORN |
|---|---|
| SEQ ID NO: 5 | C*C*G*U*C*U*G*U*U*G*U*G*U*G*A*C*U*C |
| SEQ ID NO: 13 | U*U*A*U*U*A*U*U*A*U*U*A*U*U*A*U*U*A*U*U |
| SEQ ID NO: 21 | U*U*G*U*U*G*U*U*G*U*U*G*U*U*G*U*U*G*U*U |

Example 6

Figure 12:
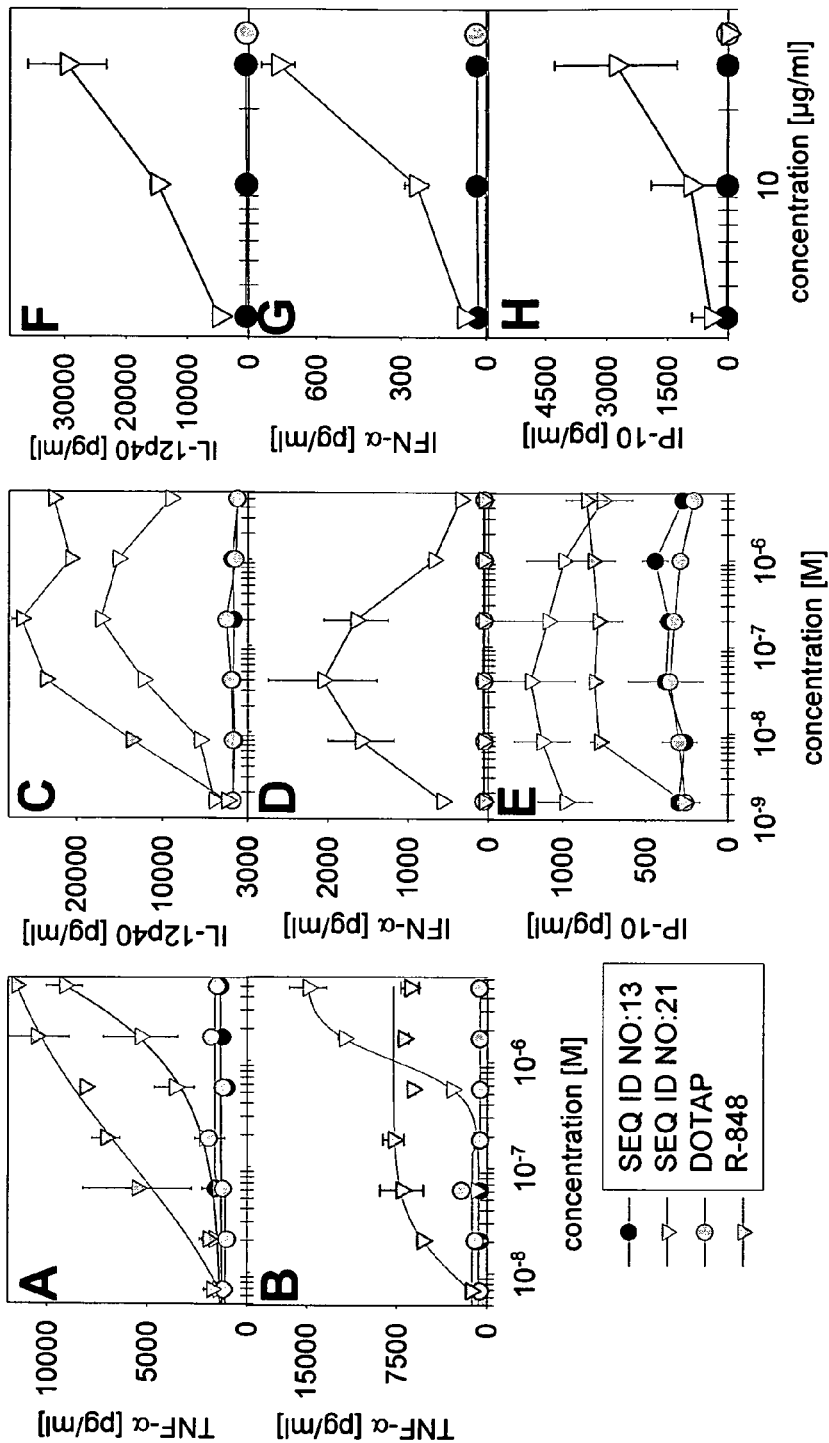
FIG. 12 is a series of graphs demonstrating that murine cells do not respond to AU-rich ORN SEQ ID NO:13 in vivo or in vitro. Cells used were mouse macrophage cell line Raw264.7 cells (FIG. 12a), J774 cells (FIG. 12b), purified mouse CD11c+ cells (sv129 mice) (FIGS. 12c-12h) and mouse cells in vivo. Cytokine concentration was evaluated by ELISA.

Mouse Macrophages do not Respond to AU-Rich ORN (SEQ ID NO:13) In Vitro or In Vivo Raw264.7 cells (FIG. 12a), J774 cells (FIG. 12b) and purified CD11c+ cells (Milteny, magnetic bead labeling) were isolated from sv129 mice splenocytes (FIGS. 12c-12e) and were stimulated with indicated concentrations of ORN complexed to DOTAP (50 µg/ml and diluted with ORN), R-848 or DOTAP alone (50 µg/ml). After 16 hours (FIGS. 12a and 12b) or 20 hours (FIGS. 12c-12e) supernatants were harvested and used for TNF-alpha (FIGS. 12a and 12b), IL-12p40 (FIG. 12c), IFN-alpha (FIG. 12d) and IP-10 (FIG. 12e) ELISA. Data represent one individual from at least three experiments (FIGS. 12a and 12b) and mean of 3 mice (FIGS. 12c-12e). To measure the ability of AU-rich ORN to stimulate mouse cells in vivo, sv129 mice (n=5/group) were injected with the indicated amounts of ORN formulated with DOTAP (60, 20 or 6 µg/ml), and bled after 3 hours. IL-12p40 (FIG. 12f), IFN-alpha (FIG. 12g) and IP-10 (FIG. 12h) production was measured within whole blood by ELISA.

Example 7

Purified Rat Splenocytes do not Respond to AU-Rich ORN SEQ ID NO:13

Figure 13:
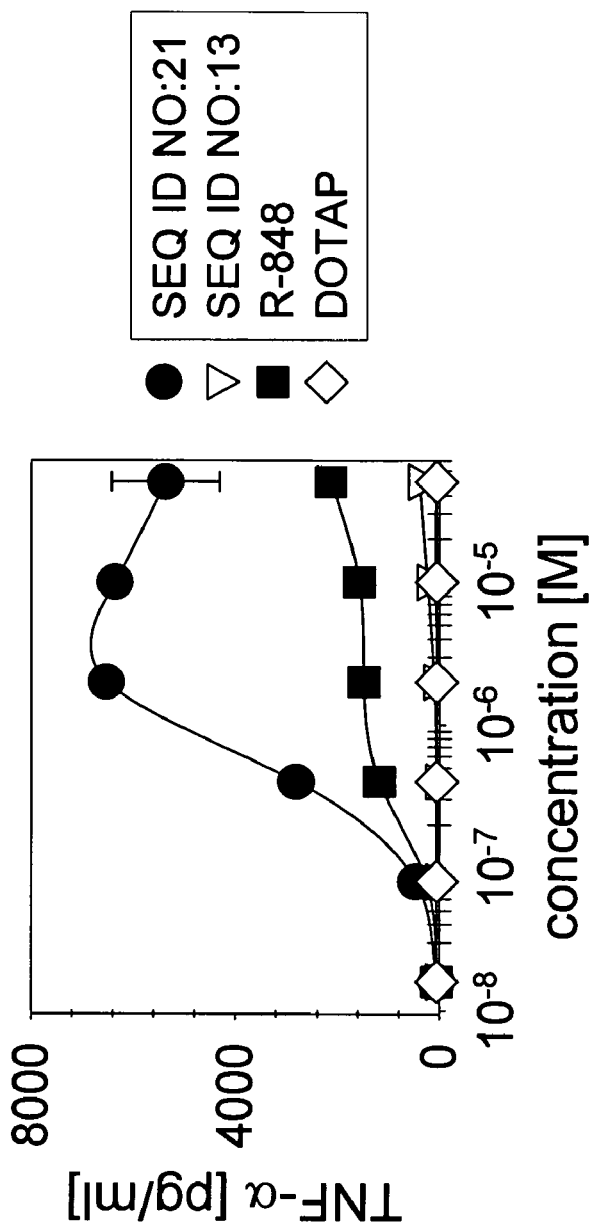
FIG. 13 is a graph demonstrating that rat splenocytes do not respond to AU-rich ORN SEQ ID NO:13. Splenocytes from 3 Sprague-Dawley rats were pooled and stimulated with indicated concentrations of SEQ ID NO:21, SEQ ID NO:13 (both complexed to 62.5 µg/ml DOTAP with 1/5 dilution), R-848 or DOTAP alone (62.5 µg/ml->1/5 dilution). Supernatants were harvested after 20 hours and TNF-alpha levels were measured by ELISA.

Splenocytes from 3 Sprague-Dawley rats were pooled and stimulated with indicated concentrations of SEQ ID NO:21, SEQ ID NO:13 (both complexed to 62.5 µg/ml DOTAP with 1/5 dilution), R-848 or DOTAP alone (62.5 µg/ml->1/5 dilution). Supernatants were harvested after 20 hours and TNF-alpha levels were measured by ELISA. As shown in FIG. 13, stimulation with GU-rich ORN SEQ ID NO:21 resulted in TNF-alpha production, whereas stimulation with AU-rich ORN SEQ ID NO:13 resulted in no TNF-alpha production.

Example 8

Failure of Rodent Cells to Respond to Au-Rich ORN SEQ ID NO:13 may Result from TLR8 Polymorphism Among Species Stimulation of human and bovine cells with AU-rich ORN resulted in cytokine production, whereas stimulation of mouse and rat cells did not. A TLR8 sequence alignment and analysis was performed. Protein sequence comparison of TLR8 among different vertebrates (human, monkey, chimpanzee, dog, cow, pig, mouse and rat) showed strong differences within leucine rich repeat (LRR) 3 of domain 1. While human, chimpanzee and monkey are highly conserved, rat, mouse and pig demonstrated deletions of 4 AA at position 106 (mouse), 103 (rat) or 102 (pig), and cow demonstrated an insertion of 2AA (105-106) compared to humans. Interestingly, pig and cattle revealed another deletion of 2 AA within the same region (position 97). It is possible that the deletion in the leucine rich repeat region of domain 1 may interfere with AU-rich ORN binding.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages of the invention are not necessarily encompassed by each embodiment of the invention.

All references, patents and patent publications that are recited in this application are incorporated in their entirety herein by reference.

We claim:

1. An oligoribonucleotide consisting of UUAUUAUUA-UUAUUAUUAUU (SEQ ID NO: 13), wherein the oligoribonucleotide includes at least one backbone modification.

2. The oligoribonucleotide of claim 1, wherein the oligoribonucleotide is complexed to N-[1-(2,3-Dioleoyioxy)propyl],N,N,N-trimethylammonium methyl sulfate to form a conjugate.

3. The oligoribonucleotide of claim 1, wherein the backbone comprises internucleoside phosphorothioate linkages between each nucleotide.

4. The oligoribonucleotide of claim 1, wherein the oligoribonucleotide is separated from 5' ribonucleotide by a non-nucleotide linker.

5. The oligoribonucleotide of claim 1, wherein the oligoribonucleotide is separated from a 3' ribonucleotide by a non-nucleotide linker.

6. The oligoribonucleotide of claim 1, wherein the oligoribonucleotide is separated from a 5' arid 3' ribonucleotide by a non-nucleotide linker.

7. A composition comprising an oligoribonucleotide consisting of UUAUUAUUAUUAUUAUUAUU (SEQ ID NO: 13) in a delivery vehicle, wherein said oligoribonucleotide includes at least one backbone modification; and optionally non-nucleotidic linkers; and optionally a) a lipophilic moiety, b) a CpG motif, c) an antigen, d) an adjuvant, and e) a pharmaceutically acceptable carrier.

8. The composition of claim 7 wherein the delivery vehicle is N-[1-(2,3-Dioleoyloxy)propyl 1-N,N,N-trimethylammonium methyl-sulfate.

9. The composition of claim 7 further comprising a lipophilic moiety.

10. The composition of claim 8 wherein the lipohilic moiety and the oligoribonucleotide are conjugated.

11. The composition of claim 7 further comprising a CpG motif.

12. The composition of claim 7 further comprising an antigen.

13. The composition of claim 7 further comprising an adjuvant.

14. The composition of claim 7 further comprising a pharmaceutically acceptable carrier.

* * * * *

UNITED STATES PATENT AND TRADEMARK OFFICE
CERTIFICATE OF CORRECTION

PATENT NO. : 7,662,949 B2 Page 1 of 1
APPLICATION NO. : 11/603978
DATED : February 16, 2010
INVENTOR(S) : Forsbach et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 512 days.

Signed and Sealed this

Thirtieth Day of November, 2010

David J. Kappos
*Director of the United States Patent and Trademark Office*